(12) United States Patent
Cooper et al.

(10) Patent No.: US 11,051,934 B2
(45) Date of Patent: Jul. 6, 2021

(54) PROSTHETIC MITRAL VALVE WITH IMPROVED ANCHORS AND SEAL

(71) Applicant: Edwards Lifesciences Corporation, Irvine, CA (US)

(72) Inventors: Alexander H. Cooper, Costa Mesa, CA (US); Juliet Laura Schwartz, Yorba Linda, CA (US); Wendy Vo Pham, Garden Grove, CA (US); Hieu Minh Luong, Westminster, CA (US); Julio Cesar Sanchez, Garden Grove, CA (US); Matthew A. Peterson, Costa Mesa, CA (US); J. Brent Ratz, Winchester, MA (US); Lisong Ai, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 31 days.

(21) Appl. No.: 16/286,436

(22) Filed: Feb. 26, 2019

(65) Prior Publication Data

US 2019/0262129 A1    Aug. 29, 2019

Related U.S. Application Data

(60) Provisional application No. 62/781,817, filed on Dec. 19, 2018, provisional application No. 62/636,672, filed on Feb. 28, 2018.

(51) Int. Cl.
*A61F 2/24*    (2006.01)
*A61F 2/95*    (2013.01)

(52) U.S. Cl.
CPC .......... *A61F 2/2409* (2013.01); *A61F 2/2418* (2013.01); *A61F 2/2427* (2013.01);
(Continued)

(58) Field of Classification Search
CPC ....................................................... A61F 2/24
See application file for complete search history.

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

(Continued)

*Primary Examiner* — Jacqueline Wozincki
(74) *Attorney, Agent, or Firm* — Knobbe, Martens, Olson & Bear LLP

(57) ABSTRACT

A mitral valve prosthesis includes an hourglass shaped inner frame and a bulbous outer frame. A valve body having a plurality of leaflets is positioned within an interior region of the inner frame. The leaflets are shaped to substantially conform to an interior surface of the inner frame when the leaflets are in an open position. As a result, the gap between the leaflets and the inner frame is decreased, thereby reducing the likelihood of thrombus formation. Ventricular anchors are preferably provided along a distal end of the inner frame. The anchors extend proximally for placement behind native mitral valve leaflets. A fabric skirt may extend along an inner or outer surface of the outer frame. In preferred embodiments, the fabric skirt extends distally (Continued)

beyond a distal end of the outer frame and is adapted for forming a seal along the mitral valve annulus.

20 Claims, 52 Drawing Sheets

(52) U.S. Cl.
CPC ............... *A61F 2002/9505* (2013.01); *A61F 2220/0008* (2013.01); *A61F 2220/0025* (2013.01); *A61F 2230/001* (2013.01); *A61F 2230/0093* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,944,690 A | 8/1999 | Falwell et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | Di Matteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,622,367 B1 | 9/2003 | Bolduc et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |

(56) References Cited

U.S. PATENT DOCUMENTS

| | | |
|---|---|---|
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0072710 A1 | 6/2002 | Stewart et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1* | 6/2005 | Justino .................. A61F 2/2418 623/1.24 |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |

(56) References Cited

U.S. PATENT DOCUMENTS

| | | |
|---|---|---|
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0100687 A1 | 5/2006 | Fahey et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0005131 A1 | 1/2007 | Taylor |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0065011 A1 | 3/2008 | Marchand et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0049313 A1* | 2/2010 | Alon .................. A61F 2/2436 623/2.11 |
| 2010/0069882 A1 | 3/2010 | Jennings et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0059458 A1* | 3/2012 | Buchbinder .......... A61F 2/2409 623/2.36 |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0165928 A1* | 6/2012 | Nitzan .................. A61F 2/2418 623/2.15 |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0030520 A1 | 1/2013 | Lee et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0261739 A1* | 10/2013 | Kuehn .................. A61F 2/2412 623/2.11 |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0005778 A1* | 1/2014 | Buchbinder .......... A61F 2/2412 623/2.18 |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0088565 A1 | 3/2014 | Vongphakdy et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0194982 A1* | 7/2014 | Kovalsky ............. A61F 2/2412 623/2.38 |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0358224 A1* | 12/2014 | Tegels .................. A61L 33/0011 623/2.14 |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |

(56) References Cited

U.S. PATENT DOCUMENTS

| | | | |
|---|---|---|---|
| 2014/0379077 A1 | 12/2014 | Tuval et al. | |
| 2015/0005863 A1 | 1/2015 | Para | |
| 2015/0012085 A1 | 1/2015 | Salahieh et al. | |
| 2015/0018938 A1 | 1/2015 | Von Segesser et al. | |
| 2015/0018944 A1 | 1/2015 | O'Connell et al. | |
| 2015/0039083 A1 | 2/2015 | Rafiee | |
| 2015/0045880 A1 | 2/2015 | Hacohen | |
| 2015/0142103 A1 | 5/2015 | Vidlund | |
| 2015/0148731 A1 | 5/2015 | McNamara et al. | |
| 2015/0157457 A1 | 6/2015 | Hacohen | |
| 2015/0157458 A1 | 6/2015 | Thambar et al. | |
| 2015/0173897 A1 | 6/2015 | Raanani et al. | |
| 2015/0196390 A1* | 7/2015 | Ma | A61F 2/2418 623/2.17 |
| 2015/0209141 A1 | 7/2015 | Braido et al. | |
| 2015/0238315 A1 | 8/2015 | Rabito et al. | |
| 2015/0272737 A1 | 10/2015 | Dale et al. | |
| 2015/0297346 A1 | 10/2015 | Duffy et al. | |
| 2015/0327994 A1 | 11/2015 | Morriss et al. | |
| 2015/0328000 A1 | 11/2015 | Ratz et al. | |
| 2015/0328001 A1 | 11/2015 | McLean et al. | |
| 2015/0335429 A1 | 11/2015 | Morriss et al. | |
| 2015/0351903 A1 | 12/2015 | Morriss et al. | |
| 2015/0351906 A1* | 12/2015 | Hammer | A61F 2/2418 623/2.11 |
| 2015/0359629 A1 | 12/2015 | Ganesan et al. | |
| 2016/0000591 A1 | 1/2016 | Lei et al. | |
| 2016/0030169 A1 | 2/2016 | Shahriari | |
| 2016/0030170 A1 | 2/2016 | Alkhatib et al. | |
| 2016/0030171 A1 | 2/2016 | Dugan et al. | |
| 2016/0038281 A1 | 2/2016 | Delaloye et al. | |
| 2016/0045311 A1 | 2/2016 | McCann et al. | |
| 2016/0074160 A1 | 3/2016 | Christianson et al. | |
| 2016/0106537 A1* | 4/2016 | Christianson | A61F 2/2463 623/2.17 |
| 2016/0113765 A1 | 4/2016 | Ganesan et al. | |
| 2016/0113766 A1 | 4/2016 | Ganesan et al. | |
| 2016/0113768 A1 | 4/2016 | Ganesan et al. | |
| 2016/0143732 A1 | 5/2016 | Glimsdale | |
| 2016/0158010 A1 | 6/2016 | Lim et al. | |
| 2016/0166383 A1 | 6/2016 | Lim et al. | |
| 2016/0184097 A1 | 6/2016 | Lim et al. | |
| 2016/0199206 A1 | 7/2016 | Lim et al. | |
| 2016/0213473 A1 | 7/2016 | Hacohen et al. | |
| 2016/0235529 A1 | 8/2016 | Ma et al. | |
| 2016/0242901 A1* | 8/2016 | Keren | A61F 2/2418 |
| 2016/0279386 A1 | 9/2016 | Dale et al. | |
| 2016/0317301 A1 | 11/2016 | Quadri et al. | |
| 2017/0035567 A1 | 2/2017 | Duffy | |
| 2017/0056169 A1 | 3/2017 | Johnson et al. | |
| 2017/0056171 A1 | 3/2017 | Cooper et al. | |
| 2017/0100236 A1* | 4/2017 | Robertson | A61F 2/2409 |
| 2017/0128209 A1 | 5/2017 | Morriss et al. | |
| 2017/0165064 A1 | 6/2017 | Nyuli et al. | |
| 2017/0216023 A1 | 8/2017 | Lane et al. | |
| 2017/0216026 A1* | 8/2017 | Quill | A61F 2/2418 |
| 2017/0216575 A1 | 8/2017 | Asleson et al. | |
| 2017/0258614 A1 | 9/2017 | Griffin | |
| 2017/0266003 A1* | 9/2017 | Hammer | A61F 2/2418 |
| 2017/0325954 A1 | 11/2017 | Perszyk | |
| 2017/0348096 A1 | 12/2017 | Anderson | |
| 2017/0360558 A1* | 12/2017 | Ma | A61F 2/2409 |
| 2017/0367823 A1 | 12/2017 | Hariton et al. | |
| 2018/0021129 A1 | 1/2018 | Peterson et al. | |
| 2018/0055629 A1 | 3/2018 | Oba et al. | |
| 2018/0055636 A1 | 3/2018 | Valencia et al. | |
| 2018/0085218 A1 | 3/2018 | Eidenschink | |
| 2018/0110534 A1 | 4/2018 | Gavala et al. | |
| 2018/0206983 A1* | 7/2018 | Noe | A61F 2/2409 |
| 2018/0296341 A1* | 10/2018 | Noe | A61M 39/22 |
| 2019/0008640 A1 | 1/2019 | Cooper et al. | |

FOREIGN PATENT DOCUMENTS

| | | |
|---|---|---|
| DE | 102006052564 B3 | 12/2007 |
| EP | 1171059 A1 | 1/2002 |
| EP | 1255510 A1 | 11/2002 |
| EP | 1259194 B1 | 11/2002 |
| EP | 1281375 A2 | 2/2003 |
| EP | 1369098 A1 | 12/2003 |
| EP | 1472996 A1 | 11/2004 |
| EP | 1734903 A1 | 12/2006 |
| EP | 1827558 A2 | 9/2007 |
| EP | 1239901 B1 | 10/2007 |
| EP | 2124826 A1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 A1 | 5/2011 |
| EP | 2398543 A1 | 12/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 9749355 A1 | 12/1997 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011008538 A1 | 1/2011 |
| WO | 2011025945 A1 | 3/2011 |
| WO | 2011057087 A1 | 5/2011 |

(56) References Cited

FOREIGN PATENT DOCUMENTS

| | | |
|---|---|---|
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Wayback Machine, Cleveland Clinic Lerner Research Institute, Transcatheter Mitral Stent/Valve Prosthetic, https:// web.archive.org/web/20130831094624/http://mds.clevelandclinic.org/Portfolio.aspx?n=331, indicated as archived on Aug. 31, 2013.

Bavaria, Joseph E M.D. et al.: "Transcatheter Mitral Valve Implantation: The Future Gold Standard for MR?," Applicant requests the Examiner to consider this reference to be prior art as of Dec. 2010.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

Bavaria, Joseph E. M.D.: "CardiAQ Valve Technologies: Transcatheter Mitral Valve Implantation," Sep. 21, 2009.

Boudjemline, Younes, et al., "Steps Toward the Percutaneous Replacement of Atrioventricular Valves," JACC, vol. 46, No. 2, Jul. 19, 2005:360-5.

"CardiAQTM Valve Technologies reports Successful First-in-Human Trans-Apical implantation of its Second Generation Transcatheter Mitral Valve," CardiAQ Valve Technologies Press Release, May 20, 2014.

"Company Overview," at TVT on Jun. 25, 2009.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. 2006.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Feldman, Ted, MD. "Prospects for Percutaneous Valve Therapies," Circulation 2007;116:2866-2877. Applicant believes that this may be available as early as Dec. 11, 2007.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.

Karimi, Houshang, et al., "Percutaneous Valve Therapies," SIS 2007 Yearbook, Chapter 11, pp. 1-11.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.

Mack, Michael, M.D., "Antegrade Transcatheter Mitral valve Implantation: A Short-term Experience in Swine Model," Applicant believes this may have been presented on May 2011 at TVT.

Mack, Michael, M.D., "Antegrade Transcatheter Mitral valve Implantation: On-Going Experience in Swine Model," Applicant believes this may have been presented on Nov. 2011 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

(56) References Cited

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes his may have been presented on Sep. 22, 2010 at TCT.
Ratz, J. Brent, "LSI EMT Spotlight," May 15, 2009.
Raiz, J. Brent, "In3 Company Overview," Jun. 24, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
"Update," Applicant believes this may have been presented on Jun. 6, 2010 at TVT.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

\* cited by examiner

PROSTHETIC MITRAL VALVE WITH IMPROVED ANCHORS AND SEAL

CROSS-REFERENCES TO RELATED APPLICATIONS

This application claims the benefit of U.S. Provisional Application No. 62/781,817, filed Dec. 19, 2018, entitled "PROSTHETIC MITRAL VALVE WITH IMPROVED ANCHORS AND SEAL" and U.S. Provisional Application No. 62/636,672, filed Feb. 28, 2018, entitled "PROSTHETIC MITRAL VALVE WITH IMPROVED ANCHORS AND SEAL", the entirety of each of which is hereby incorporated by reference.

BACKGROUND

Field

Certain embodiments disclosed herein relate generally to prostheses for implantation within a lumen or body cavity. In particular, certain embodiments relate to expandable prostheses such as replacement heart valves, such as for the mitral valve, that are configured to be secured to intralumenal tissue and prevent paravalvular leakage.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. For example, in the context of replacement heart valves, paravalvular leakage has proven particularly challenging. An additional challenge relates to the ability of such prostheses to be secured relative to intralumenal tissue, e.g., tissue within any body lumen or cavity, in an atraumatic manner. Yet another challenge arises when trying to reduce the likelihood of thrombosis within parts of the replacement valves.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

In some embodiments, a delivery system and method are provided for delivering a replacement heart valve to a native mitral valve location. The delivery system and method may utilize a transseptal approach. In some embodiments, components of the delivery system facilitate bending of the delivery system to steer a prosthesis from the septum to a location within the native mitral valve. In some embodiments, a capsule is provided for containing the prosthesis for delivery to the native mitral valve location. In other embodiments, the delivery system and method may be adapted for delivery of implants to locations other than the native mitral valve.

The present disclosure includes, but is not limited to, the following embodiments.

Embodiment 1

A mitral valve prosthesis configured to transition between a compressed position and an expanded position, the prosthesis having a proximal end and a distal end, the prosthesis comprising an inner frame comprising a body comprising a plurality of circumferentially extendable struts, and a plurality of longitudinally extending struts, wherein the plurality of circumferentially extendable struts and the plurality of longitudinally extending struts form two or more rows of cells, and a plurality of inner frame anchoring features extending distally from the body, wherein the inner frame is generally hourglass shaped in the expanded position, an outer frame connected to the inner frame and comprising a plurality of connected first v-shaped struts extending around a circumference of the prosthesis, and a plurality of separate second v-shaped struts, each of the separate second v-shaped struts attached within each of the connected first v-shaped struts, a valve body connected within an interior surface of the inner frame, the valve body comprising a plurality of leaflets arranged to allow flow in a first direction and prevent flow in a second direction opposite the first direction, wherein the leaflets conform to the interior surface of the inner frame when the valve body is in an open position for reducing a formation of thrombi between the plurality of leaflets and the interior surface of the inner frame, and a fabric skirt connected to an inner surface of the outer frame and extending distally beyond a distal end of the outer frame, wherein the fabric skirt is adapted for contacting a mitral annulus and forming a seal.

Embodiment 2

The mitral valve prosthesis of Embodiment 1, wherein the plurality of separate second v-shaped struts are thinner than the plurality of connected first v-shaped struts.

Embodiment 3

The mitral valve prosthesis of Embodiment 1 or Embodiment 2, further comprising a stiffness improving material attached to the outer frame, the inner frame, and the plurality of inner frame anchoring features, the stiffness improving material providing tension to the inner frame anchoring features when the prosthesis is in the expanded position and not providing tension to the inner frame anchoring features when the prosthesis is in the compressed position.

Embodiment 4

The mitral valve prosthesis of any one of Embodiments 1-3, wherein the plurality of inner frame anchoring features extend radially outwardly and then proximally, wherein each of the plurality of inner frame anchoring features ends with an anchoring tip.

Embodiment 5

The mitral valve prosthesis of Embodiment 4, wherein a distal end of the outer frame is longitudinally spaced above each of the anchoring tips.

Embodiment 6

The mitral valve prosthesis of any one of Embodiments 1-5, wherein a distal end of the outer frame ends proximal to a distal end of the two or more rows of cells.

Embodiment 7

The mitral valve prosthesis of any one of Embodiments 1-6, wherein the inner frame comprises a mushroom tab at a proximal end of at least one of the plurality of longitudinally extending struts.

Embodiment 8

The mitral valve prosthesis of any one of Embodiments 1-7, wherein the inner frame and the outer frame each comprise a plurality of apertures at or near a proximal end of the inner frame and the outer frame, and wherein each of the plurality of apertures of the inner frame generally aligns with an aperture of the plurality of apertures of the outer frame.

Embodiment 9

The mitral valve prosthesis of any one of Embodiments 1-8, wherein the outer frame comprises a plurality of outer frame anchoring features extending radially outwards.

Embodiment 10

The mitral valve prosthesis of any one of Embodiments 1-9, wherein the skirt is positioned between the inner frame and the outer frame.

Embodiment 11

The mitral valve prosthesis of any one of Embodiments 1-11, further comprising a valve body positioned within an interior of the inner frame, the valve body comprising a plurality of leaflets configured to allow flow in a first direction and prevent flow in a second opposite direction.

Embodiment 12

The mitral valve prosthesis of any one of Embodiments 1-11, wherein the expandable replacement heart valve prosthesis is configured to act as a replacement mitral heart valve.

Embodiment 13

The mitral valve prosthesis of any one of Embodiments 1-12, wherein each of the plurality of inner frame anchoring features ends with a pair of L-shaped anchors, the pair of L-shaped anchors being radially offset from one another.

Embodiment 14

The mitral valve prosthesis of any one of Embodiments 1-13, wherein the outer frame comprises a plurality of proximally extending struts extending between connections of adjacent connected first v-shaped struts.

Embodiment 15

The mitral valve prosthesis of Embodiment 14, wherein the outer frame comprises a circumferential shoulder spaced from a proximal end and a distal end of the outer frame, the circumferential shoulder being the radially outermost portion of the outer frame.

Embodiment 16

The mitral valve prosthesis of Embodiment 16, wherein the proximally extending struts are spaced radially inwards from the circumferential shoulder, and wherein a distal end of each of the plurality of first v-shaped struts is spaced radially inwards from the circumferential shoulder.

Embodiment 17

The mitral valve prosthesis of any one of Embodiments 1-16, wherein the expandable replacement heart valve prosthesis comprises nine inner frame anchoring features.

Embodiment 18

A delivery assembly configured to delivery an expandable replacement heart valve prosthesis, the delivery assembly comprising a steerable delivery system configured to releasably retain the expandable replacement heart valve prosthesis in a compressed position, and the expandable replacement heart valve prosthesis configured to expandable between the compressed position and an expanded position, the prosthesis comprising an inner frame comprising a plurality of circumferentially extendable struts, a plurality of longitudinal extending struts, and a plurality of inner frame anchoring features, wherein the inner frame is generally hourglass shaped in the expanded position, and an outer frame connected to the inner frame and comprising a plurality of connected first v-shaped struts extending around a circumference of the prosthesis, wherein the steerable delivery system is configured to sequentially expand portions of the prosthesis from the compressed position to the expanded position.

Embodiment 19

The delivery assembly of Embodiment 18, wherein the outer frame further comprises a plurality of separate second v-shaped struts, each of the separate second v-shaped struts attached within each of the connected first v-shaped struts.

Embodiment 20

The delivery assembly of Embodiment 18 or Embodiment 19, wherein the steerable delivery system further comprises an anchor separator comprising a body, a plurality of extensions extending radially away from the body, the plurality of extensions forming a plurality of longitudinally extending grooves, each of the plurality of longitudinally extending grooves configured to receive one of the plurality of inner frame anchoring features in the compressed position, and a lumen longitudinally extending through the body, wherein the body and the plurality of extensions are radially inwardly tapered at a proximal end and distal end of the anchor separator.

Embodiment 21

An expandable replacement heart valve prosthesis. The prosthesis can be configured to transition between a compressed position and an expanded position. The prosthesis can comprise an inner frame. The inner frame can comprise a plurality of circumferentially extendable struts. The inner frame can comprise a plurality of longitudinally extending struts. The plurality of circumferentially extendable struts and the plurality of longitudinally extending struts can form two or more rows of cells. The inner frame can comprise a plurality of inner frame anchoring features. The inner frame can be generally hourglass shaped in the expanded position. The prosthesis can comprise an outer frame. The outer frame can be connected to the inner frame. The outer frame can comprise a plurality of connected first v-shaped struts. The plurality of connected first v-shaped struts can extend around a circumference of the prosthesis. The outer frame can comprise a plurality of separate second v-shaped struts. Each of the separate second v-shaped struts can be attached within each of the connected first v-shaped struts. The plurality of separate second v-shaped struts can be thinner than the plurality of connected first v-shaped struts. The prosthesis can comprise a stiffness improving material attached to the outer frame. The stiffness improving material can be attached to the inner frame. The stiffness improving material can be attached to the plurality of inner frame anchoring features. The stiffness improving material can provide tension to the inner frame anchoring features when the prosthesis is in the expanded position. The stiffness improving material may not providing tension to the inner frame anchoring features when the prosthesis is in the compressed position.

Embodiment 22

The prosthesis of Embodiment 21, wherein the stiffness improving material can comprise sutures, fabric, or cloth.

Embodiment 23

The prosthesis of Embodiments 21-22, wherein the outer frame can comprise a plurality of outer frame anchoring features.

Embodiment 24

The prosthesis of Embodiments 21-23, wherein the prosthesis can be configured for use as a replacement mitral valve.

Embodiment 25

The prosthesis of any one of Embodiments 21-24, wherein the prosthesis can comprise a skirt positioned between the inner frame and the outer frame. The skirt can be configured to automatically tuck within cells in the outer frame when the prosthesis is compressed.

Embodiment 26

The prosthesis of any one of Embodiments 21-25, wherein the prosthesis can comprise a valve body. The valve body can be positioned within an interior of the first frame. The valve body can comprise a plurality of leaflets configured to allow flow in a first direction and prevent flow in a second opposite direction.

Embodiment 27

An expandable replacement heart valve prosthesis configured to transition between a compressed position and an expanded position, wherein the inner frame can comprise a generally cylindrical first frame and an inwardly curved secondary frame located within the generally cylindrical first frame and attached to the generally cylindrical first frame, the inwardly curved secondary frame forming a generally hourglass shape within a longitudinal lumen of the inner frame.

Embodiment 28

The prosthesis of Embodiment 27, wherein the secondary frame can comprise a plurality of longitudinal struts on an outer surface of a fabric component.

Embodiment 29

The prosthesis of Embodiment 27, wherein the secondary frame can comprise a balloon filled with fluid.

Embodiment 30

The prosthesis of Embodiment 27, wherein the secondary frame can comprise a swellable material.

Embodiment 31

The prosthesis of any one of Embodiments 21-26, comprising the features of any one of Embodiments 27-30.

Embodiment 32

The prosthesis of any one of Embodiments 21-31, wherein each of the plurality of inner frame anchoring features can end with a pair of L-shaped anchors, the pair of L-shaped anchors being radially offset from one another.

Embodiment 33

A delivery system configured to deliver a prosthesis comprising a plurality of anchors, including any of the prostheses described herein this specification. The delivery system comprises an anchor separator comprising a body, a plurality of extensions extending radially away from the body, the plurality of extensions forming a plurality of longitudinally extending grooves for receiving the anchors of the prosthesis, and a lumen longitudinally extending through the body. The body and the plurality of extensions are radially inwardly tapered at a proximal end and distal end of the anchor separator.

Embodiment 34

An expandable replacement heart valve prosthesis. The prosthesis can be configured to transition between a compressed position and an expanded position. The prosthesis can comprise a frame. The frame can have an inlet side. The frame can have a middle portion. The frame can have an outlet side. The frame can decrease in diameter at least from the inlet side to the middle portion. The prosthesis can comprise a valve body comprising a plurality of leaflets positioned within the frame. Each of the valve leaflets can have an inlet end positioned along the decreasing diameter portion of the frame.

Embodiment 35

The prosthesis of Embodiment 34, wherein the frame can be an hourglass shape.

Embodiment 36

An expandable replacement heart valve prosthesis. The prosthesis can be configured to transition between a compressed position and an expanded position. The prosthesis can comprise an inner frame. The inner frame can comprise a plurality of inner frame anchoring features. The features can extend from a lower portion of the inner frame. The prosthesis can comprise an outer frame. The outer frame can be connected to the inner frame. The prosthesis can comprise a stiffness improving material. The material attached to the outer frame. The material attached to the inner frame. The material attached to the plurality of inner frame anchoring features. The stiffness improving material can provide tension to the inner frame anchoring features when the prosthesis is in the expanded position. The material may not provide tension to the inner frame anchoring features when the prosthesis is in the compressed position.

Embodiment 37

The prosthesis of Embodiment 36, wherein the inner frame anchoring features can comprise a plurality of anchors. The anchors can extend radially outward from the inner frame. The anchors can extend generally toward an upper portion of the inner frame.

Embodiment 38

The prosthesis of any one of Embodiments 36 or 37, wherein the outer frame can extend over the inner frame.

Embodiment 39

The prosthesis of any one of Embodiments 36-38, wherein the stiffness improving material can comprise suture, fabric, or cloth material. The material can extend from a lower portion of the outer frame. The material can attach to the inner frame anchoring features. The material can attach to a lower portion of the inner frame.

Embodiment 40

An expandable replacement heart valve prosthesis. The prosthesis can be configured to transition between a compressed position and an expanded position. The prosthesis can comprise a frame. The frame can comprise a plurality of connected first v-shaped struts. The struts can extend around a circumference of the prosthesis. The frame can comprise a plurality of separate second v-shaped struts. Each of the separate second v-shaped struts can be attached within each of the connected first v-shaped struts. The plurality of separate second v-shaped struts can be thinner than the plurality of connected first v-shaped struts.

Embodiment 41

An expandable replacement heart valve prosthesis. The prosthesis can be configured to transition between a compressed position and an expanded position. The prosthesis can comprise a frame. The frame can comprise a plurality of circumferentially extendable struts. The frame can comprise a plurality of longitudinally extending struts. The plurality of circumferentially extendable struts and the plurality of longitudinally extending struts can form two or more rows of cells.

Embodiment 42

A frame which can comprise a cell pattern as shown and described in FIGS. 3, 4 and/or 5A.

Embodiment 43

A prosthesis comprising one or more features of the foregoing description.

Embodiment 44

A method of treating valve insufficiency comprising one or more features of the foregoing description.

Embodiment 45

A delivery system for delivering the prosthesis comprising one or more features of the foregoing description.

Embodiment 46

The mitral valve prosthesis of any one of Embodiments 1-17, wherein free edges of a distal end of each of the plurality of leaflets are spaced away from the inner frame.

Embodiment 47

The mitral valve prosthesis of any one of Embodiments 1-17 and 46, wherein the fabric skirt is connected to an outer surface of a distal end of the inner frame, and wherein the fabric skirt is held in tension between the outer frame and the inner frame.

Embodiment 48

The mitral valve prosthesis of any one of Embodiments 1-17 and 46-47, wherein the fabric skirt has sufficient flexibility to conform against a mitral annulus.

Embodiment 49

A mitral valve prosthesis configured to transition between a compressed position and an expanded position, the prosthesis having a proximal end and a distal end, the prosthesis comprising an inner frame comprising a body comprising a plurality of circumferentially extendable struts, and a plurality of longitudinally extending struts, wherein the plurality of circumferentially extendable struts and the plurality of longitudinally extending struts form two or more rows of cells, and a plurality of inner frame anchoring features extending distally from the body, wherein the inner frame is generally hourglass shaped in the expanded position, an outer frame connected to the inner frame and comprising a plurality of connected first v-shaped struts extending around a circumference of the prosthesis, and a plurality of separate second v-shaped struts, each of the separate second v-shaped struts attached within each of the connected first v-shaped struts, a valve body connected within an interior surface of the inner frame, the valve body comprising a plurality of leaflets arranged to allow flow in a first direction and prevent flow in a second direction opposite the first direction, and a fabric skirt connected to an inner surface of the outer frame and an outer surface of a distal end of the inner frame under tension, wherein the fabric skirt extends distally beyond a distal end of the outer frame, and wherein the fabric skirt is adapted for conforming against a mitral annulus.

Embodiment 50

A mitral valve prosthesis configured to transition between a compressed position and an expanded position, the prosthesis having a proximal end and a distal end, the prosthesis comprising an inner frame comprising a body comprising a plurality of circumferentially extendable struts, and a plurality of longitudinally extending struts, wherein the plurality of circumferentially extendable struts and the plurality of longitudinally extending struts form two or more rows of cells, and a plurality of inner frame anchoring features extending distally from the body, wherein the inner frame is generally hourglass shaped in the expanded position, an outer frame connected to the inner frame and comprising a plurality of connected first v-shaped struts extending around a circumference of the prosthesis, and a plurality of separate second v-shaped struts, each of the separate second v-shaped struts attached within each of the connected first v-shaped struts.

BRIEF DESCRIPTION OF THE DRAWINGS

These and other features, aspects and advantages are described below with reference to the drawings, which are intended to illustrate embodiments of prostheses including embodiments of various components of these prostheses.

DETAILED DESCRIPTION

Figure 1:
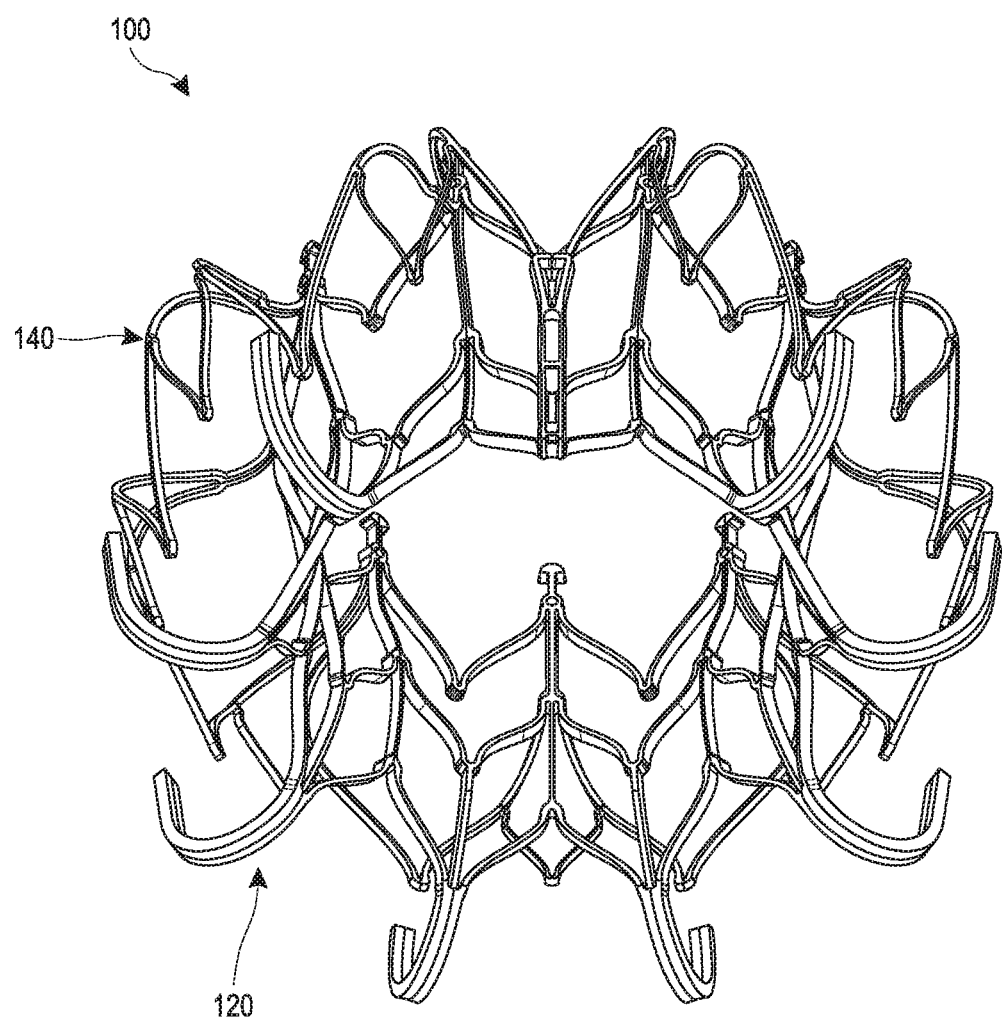
FIG. 1 illustrates an embodiment of a multi-portion replacement prosthesis.

The present specification and drawings provide aspects and features of the disclosure in the context of several embodiments of prostheses, replacement heart valves, and methods that are configured for use in the vasculature of a patient, such as for replacement of natural heart valves in a patient. These embodiments may be discussed in connection with replacing specific valves such as the patient's mitral valve. However, it is to be understood that the features and concepts discussed herein can be applied to replacing other types of valves including, but not limited to, the aortic valve, the pulmonary valve, and the tricuspid valve. Moreover, it is to be understood that the features and concepts discussed herein can be applied to products other than heart valve implants. For example, the controlled positioning, deployment, and/or securing features described herein can be applied to medical implants, for example other types of expandable prostheses, for use elsewhere in the body, such as within a vein, or the like. In addition, particular features of a prosthesis should not be taken as limiting, and features of any one embodiment discussed herein can be combined with features of other embodiments as desired and when appropriate.

Certain terminology may be used in the following description for the purpose of reference only, and thus are not intended to be limiting. For example, terms such as "upper", "lower", "upward", "downward", "above", "below", "top", "bottom" and similar terms refer to directions in the drawings to which reference is made. Terms such as "proximal", "distal", "radially outward", "radially inward", "outer", "inner", and "side", describe the orientation and/or location of portions of the components or elements within a consistent but arbitrary frame of reference which is made clear by reference to the text and the associated drawings describing the components or elements under discussion. Such terminology may include the words specifically mentioned above, derivatives thereof, and words of similar import. Similarly, the terms "first", "second", and other such numerical terms referring to structures neither imply a sequence or order unless clearly indicated by the context.

In some embodiments, the term "proximal" may refer to the parts of the prostheses, or components thereof, which are located closer to the operator of the device and system (e.g., the clinician implanting the prosthesis). The term "distal" may refer to the parts of the prostheses, or components thereof, which are located further from the operator of the device and system (e.g., the clinician implanting the prosthesis). However, it is to be understood that this terminology may be reversed depending on the delivery technique utilized (e.g., a transapical approach as compared to a transseptal approach). In some situations, the prosthesis, or components thereof, may be oriented such that an upper end is a proximal portion and a lower end is a distal portion.

In some situations, the prosthesis, or components thereof, the upper end may be an inflow end and the lower end may be an outflow end. For example, a valve body used with the prosthesis can allow flow from the upper end to the lower end. However, it is to be understood that the inflow end and the outflow end may be reversed. For example, the valve body used with the prosthesis can allow flow from the lower end to the upper end.

A longitudinal axis of the prosthesis, or components thereof, may be defined as the central axis that extends through the center of the prosthesis or component between the upper and lower ends of the prosthesis or component (e.g., the prosthesis, the outer frame, and/or the inner frame). The prostheses described herein may be replacement valves that can be designed to replace a damaged or diseased native heart valve such as a mitral valve, as discussed above. It should be understood that the prostheses are not limited to being a replacement valve.

As will be described in further detail below, the prostheses can include an inner frame and/or an outer frame or an inner portion and/or an outer portion. In some embodiments, the inner frame can be a valve frame designed to support a valve body. In some embodiments, the outer frame can be a sealing frame designed to form a seal about a periphery of the outer frame. For example, the outer frame can engage tissue of a body cavity about a periphery of the outer frame and form a seal with said tissue. In some embodiments described herein, the outer frame can be attached to the inner frame at one or more stationary couplings such that the outer frame is fixed to the inner frame at one or more locations. It is to be understood that the outer frame can be attached to the inner frame via one or more movable couplings such as, but not limited to, rails. This can beneficially allow the outer frame to be adjusted relative to the inner frame to better conform to the anatomy of a patient's body cavity.

The inner frame and/or outer frame may be described as having an upper region, an intermediate region, and a lower region. In some situations, such as those in which the prostheses are positioned within a native mitral valve, the upper region can be generally positioned supra-annularly (i.e., above the plane of the annulus), the intermediate region can be generally positioned intra-annularly (i.e., within the plane of the annulus), and the lower region can be positioned sub-annularly (i.e., below the plane of the annulus). However, it is to be understood that in some situations, the positioning of the inner frame and/or outer frame relative to the annulus can differ. Moreover, it is to be understood that in some embodiments, the inner frame and/or outer frame can omit one or more of the upper region, the intermediate region, and/or the lower region.

While certain combinations of inner frames and outer frames are described herein, it is to be understood that the inner frames and outer frames can be interchanged. This can beneficially allow the prosthesis to be configured in a manner which better suits the native anatomy of the patient. Moreover, while the inner frames and outer frames can be attached prior to delivery into the patient, it is to be understood that the inner frames and outer frames can be delivered separately into the patient and subsequently attached in the patient's body. This can beneficially reduce the crimp profile when delivering the frames to the body cavity. The prostheses described herein can be used as a standalone device. For example, the prosthesis can be deployed at a native mitral valve and be sized and shaped appropriately to replace the function of the native mitral valve. However, it is to be understood that the prostheses described herein can be used with other devices. For example, one or more clips can be used to hold together native leaflets of a heart valve. This can advantageously allow a smaller prosthesis to be utilized at the native mitral valve.

Embodiments of Replacement Valves and Frames

FIG. 1 shows an embodiment of the frame of a multi-portion prosthesis 100 in an expanded configuration. The prosthesis 100 can include, but are not limited to, an inner frame 120, an outer frame 140, a valve body 160 (shown in FIGS. 9-11), and a skirt 180 (also shown in FIGS. 9-11). A longitudinal axis of the prosthesis 100 may be defined as the central axis that extends through the center of the prosthesis 100 between the upper and lower ends of the prosthesis 100. In some situations, the prosthesis 100 may be oriented such that an upper end of the prosthesis 100 is a proximal portion and a lower end of the prosthesis 100 is a distal portion. The illustrated prosthesis 100, as well as other prostheses described herein, may include components which are self-expanding or balloon expandable. For example, in some embodiments, the inner frame 120 and/or outer frame 140 can be self-expanding. The prosthesis 100, as well as other prostheses described herein, may be a replacement valve that can be designed to replace a damaged or diseased native heart valve such as a mitral valve, as discussed above. It should be understood that the prosthesis 100, as well as other prostheses described herein, are not limited to being a replacement valve.

Embodiments of the disclosed prosthesis 100 may have a reduced crimp inner diameter (ID), such as 25Fr, 24Fr, 23Fr, 22Fr, 21Fr, or 20Fr. Embodiments of the disclosed prosthesis 100 may have a reduced crimp ID, such as less than 25Fr, 24Fr, 23Fr, 22Fr, 21Fr, or 20Fr. Embodiments of the disclosed prosthesis 100 may have a reduced crimp ID, such as greater than 25FR, 24Fr, 23Fr, 22Fr, 21Fr, or 20Fr. In some embodiments, the prosthesis 100 may have a crimp length of 48, 47, 46, 45, 44, 43, 42, 41, or 40 mm. In some embodiments, the prosthesis 100 may have a crimp length of less than 48, 47, 46, 45, 44, 43, 42, 41, or 40 mm. In some embodiments, the prosthesis 100 may have a crimp length of greater than 48, 47, 46, 45, 44, 43, 42, 41, or 40 mm. In some embodiments, the prosthesis 100 may only require retrieval forces of 60, 55, 50, 45, or 40 lbs. to compress the prosthesis 100. In some embodiments, the prosthesis 100 may only require retrieval forces of less than 60, 55, 50, 45, or 40 lbs. to compress the prosthesis 100. In some embodiments, the prosthesis 100 may only require retrieval forces of greater than 60, 55, 50, 45, or 40 lbs. to compress the prosthesis 100.

As further disclosed below, the multi-portion prosthesis 100 can be made of one or more frames, such as one, two, or three frames. In some embodiments, the prosthesis 100 can be a dual-frame design, having an inner and an outer frame. In some embodiments, the inner and outer frame are integrally formed into one frame. In other embodiments, the frames can be separate and connected together.

Inner Frame

Figure 2:
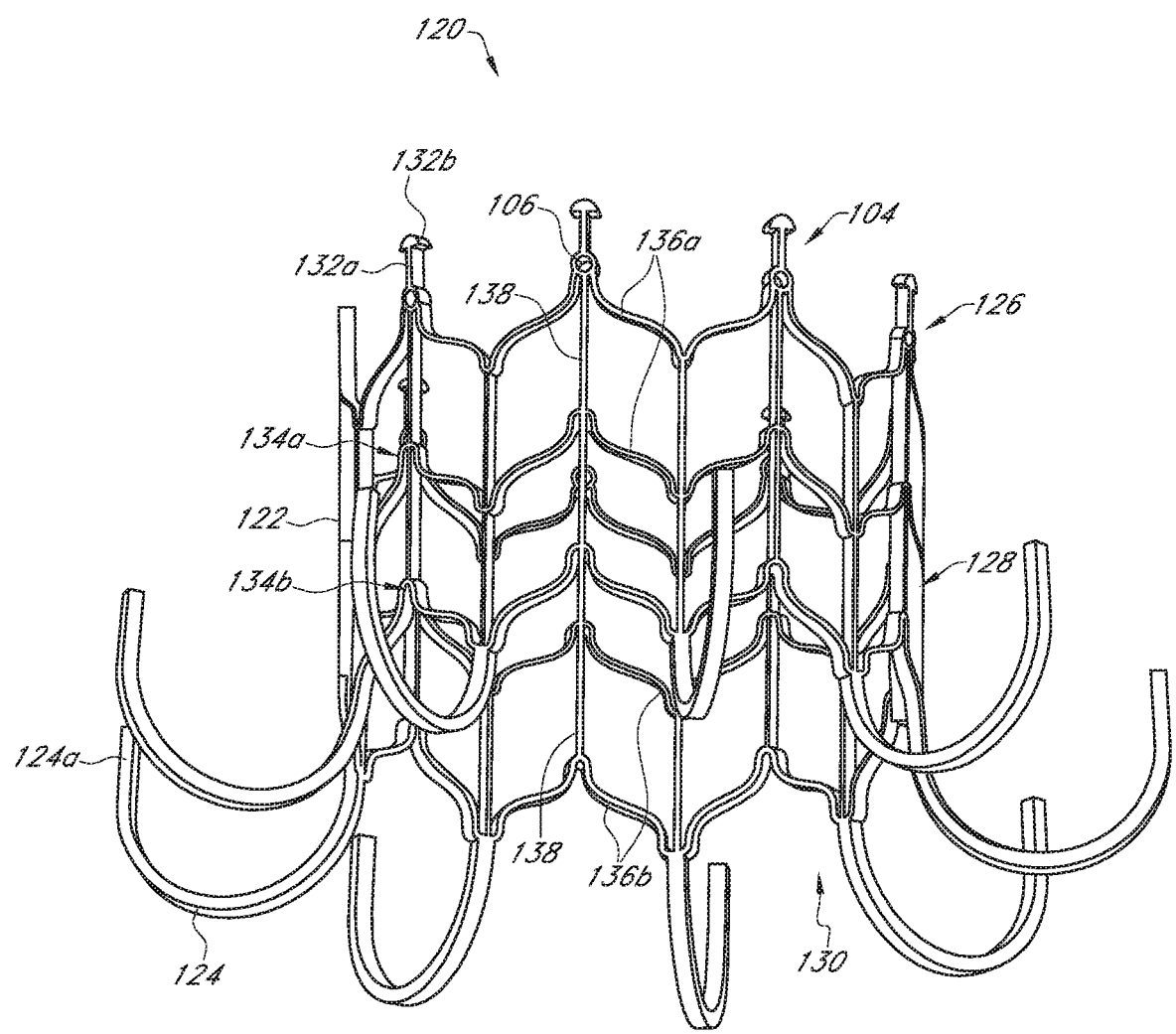
FIG. 2 illustrates an embodiment of an inner frame of the multi-portion replacement prosthesis shown in FIG. 1.
Figure 3:
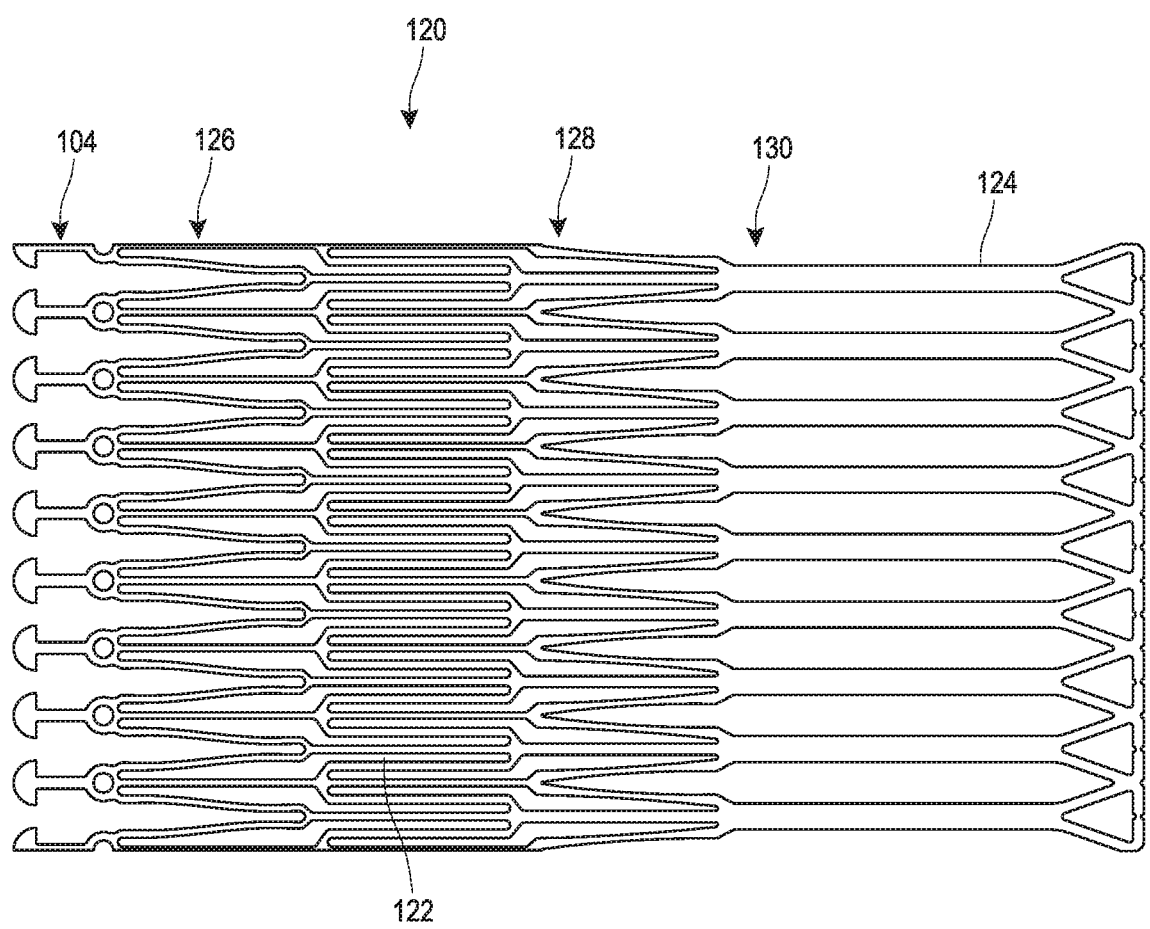
FIG. 3 illustrates a flat pattern of an embodiment of the inner frame shown in FIG. 2.

FIG. 2 illustrates the inner frame 120 of the prosthesis 100 with the outer frame 140 removed for clarity. Further, FIG. 3 illustrates a flat pattern of the inner frame 120. The inner frame 120 can generally include an inner frame body 122 and an inner frame anchoring feature 124 (if used in a mitral valve, also known as a ventricular or distal anchor). The inner frame body 122 can have an upper region 126, an intermediate region 128, and a lower region 130. As shown, the inner frame body 122 can have a generally cylindrical shape such that the diameters of the upper region 126, the intermediate region 128, and the lower region 130 are generally equivalent. However, it is to be understood that the diameters of the upper region 126, the intermediate region 128, and/or the lower region 130 can be different, such as the hourglass shape discussed below with respect to FIGS. 5A-5E. For example, in some embodiments, a diameter of the intermediate region 128 can be larger/smaller than the upper region 126 and the lower region 130 such that the frame body 122 has a generally bulbous shape. In some embodiments, the diameter of the lower region 130 can be larger than the diameter of the upper region 126. In other embodiments, the diameter of the upper region 126 can be larger than the diameter of the lower region 130. Moreover, although the inner frame body 122 has been described and illustrated as being cylindrical or having circular cross-sections, it is to be understood that all or a portion of the inner frame body 122 can have a non-circular cross-section such as, but not limited to, a D-shape, an oval or an otherwise ovoid cross-sectional shape.

In some situations, such as those in which the prosthesis 100 is positioned within a native mitral valve, the upper region 126 can be generally positioned supra-annularly (i.e., above the plane of the annulus), the intermediate region 128 can be generally positioned intra-annularly (i.e., within the plane of the annulus), and the lower region 130 can be positioned sub-annularly (i.e., below the plane of the annulus). However, it is to be understood that in some situations, the positioning of the inner frame 120 relative to the annulus can differ. For example, the intermediate region 128 can be positioned supra-annularly. Moreover, it is to be understood that in some embodiments, the inner frame 120 can omit one or more of the upper region 126, the intermediate region 128, and/or the lower region 130.

As shown FIG. 2, the inner frame 120 can include inner frame anchoring feature(s) 124 (in some embodiments ventricular anchors) which can extend generally downwardly and/or radially outwardly at or proximate a lower end of the lower region 130 of the inner frame body 122. The inner frame anchoring feature 124 can extend upwardly towards the upper region 126 after extending radially outwards. As will be discussed in further detail below, components of the inner frame 120, such as the inner frame anchoring feature 124, can be used to attach or secure the prosthesis 100 to a native valve. For example, in some situations, the inner frame anchoring feature 124 can be used to attach or secure the prosthesis 100 to a native mitral valve. In such an embodiment, the inner frame anchoring feature 124 can be positioned to contact or engage a native mitral valve annulus on a ventricular side, tissue beyond the native valve annulus on a ventricular side, native leaflets on a ventricular side, and/or other tissue at or around the implantation location during one or more phases of the cardiac cycle, such as systole and/or diastole. When positioned within the native mitral valve, the inner frame anchoring feature 124 can beneficially eliminate, inhibit, or limit upward movement of the prosthesis 100 when subject to upwardly directed forces such as those which are applied on the prosthesis 100 during systole. As shown, the prosthesis 100 can have nine inner frame anchoring features 124, but in some embodiments may have more or less, such as 1, 2, 3, 4, 5, 6, 7, 8, 9, 10, 11, or 12 inner frame anchoring features 124.

With continued reference to the inner frame 120 illustrated in FIG. 2, the inner frame anchoring feature 124 can have ends or tips 124a positioned radially outwardly relative to the longitudinal axis of the prosthesis 100. The inner frame anchoring feature 124 can extend at or proximate a lower end of the lower region 130 of the inner frame body 122. As shown, the inner frame anchoring feature 124 can be formed from a plurality of individual anchors extending from the frame body 122. The anchors can extend downwardly from one or more attachment points to the frame body 122 including, but not limited to, lower apices of cells 134b. The anchors can bend to extend generally radially outwardly of the longitudinal axis of the prosthesis 100. As shown in the illustrated embodiment, the anchors can extend upwardly towards an end or tip 124a.

As shown in the illustrated embodiment, the tips or ends 124a extend upwardly in a direction parallel or generally parallel to the longitudinal axis of the prosthesis 100. In some embodiments, the tip or end 124a of anchoring feature 124 can extend generally perpendicular to the longitudinal axis of the prosthesis 100. This can beneficially increase the tissue contact area of the tip 124a of the anchor. This increased tissue contact area can beneficially reduce the stress applied by the tip 124a to tissue thereby reducing the amount of pressure and potential for trauma to the tissue. In some embodiments, the tip or ends 124a of the anchoring feature 124 extend radially inward towards the longitudinal axis and/or radially outward away from the longitudinal axis.

Figure 5A:
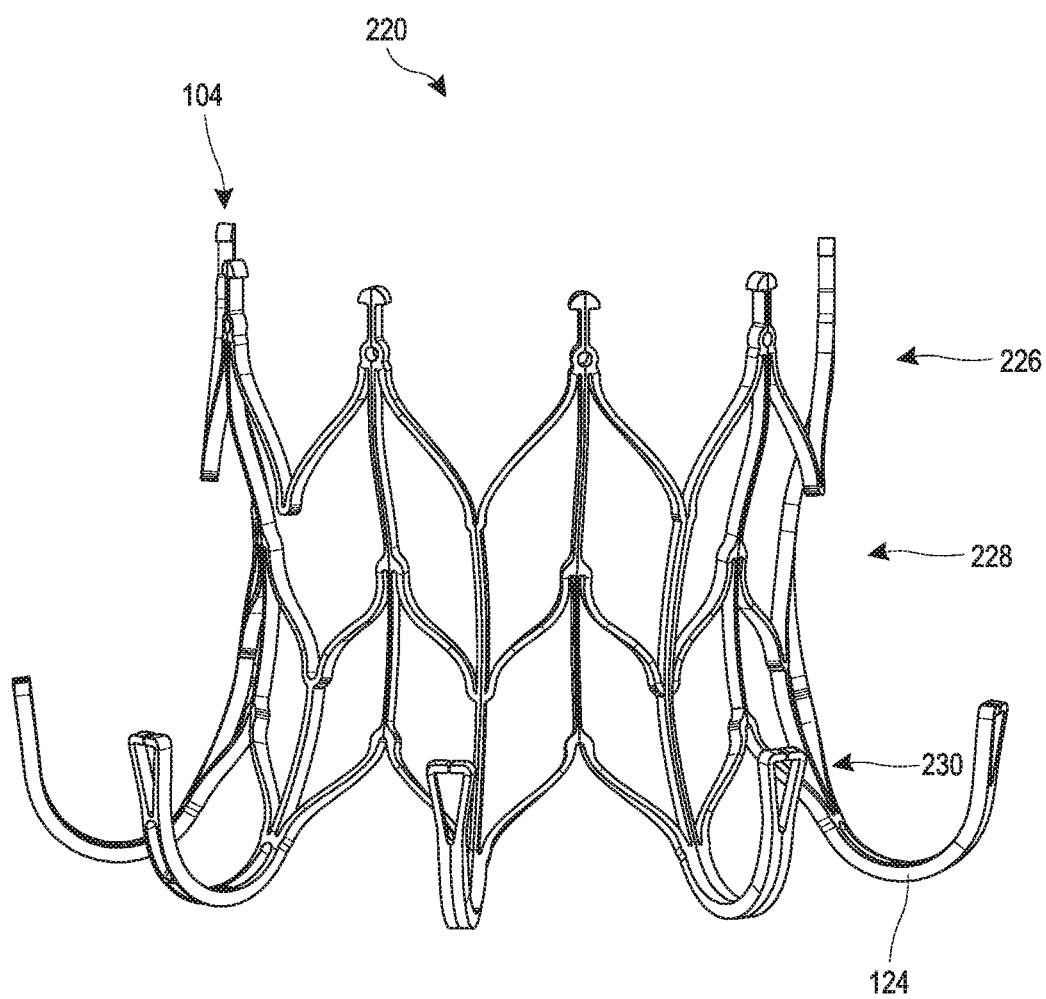
FIGS. 5A-5E illustrate an inner frame having an hourglass shape.
Figure 5B:
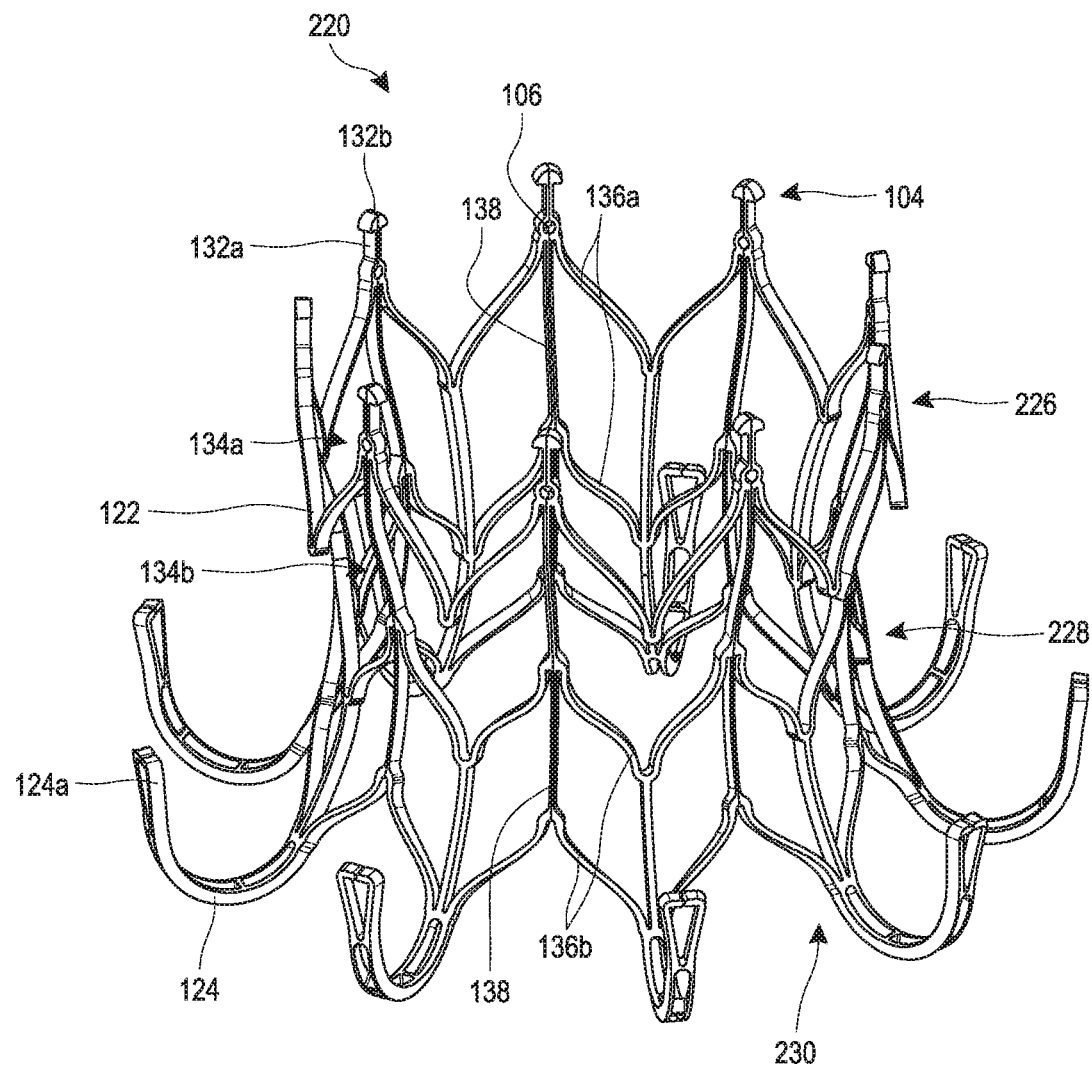
Figure 5C:
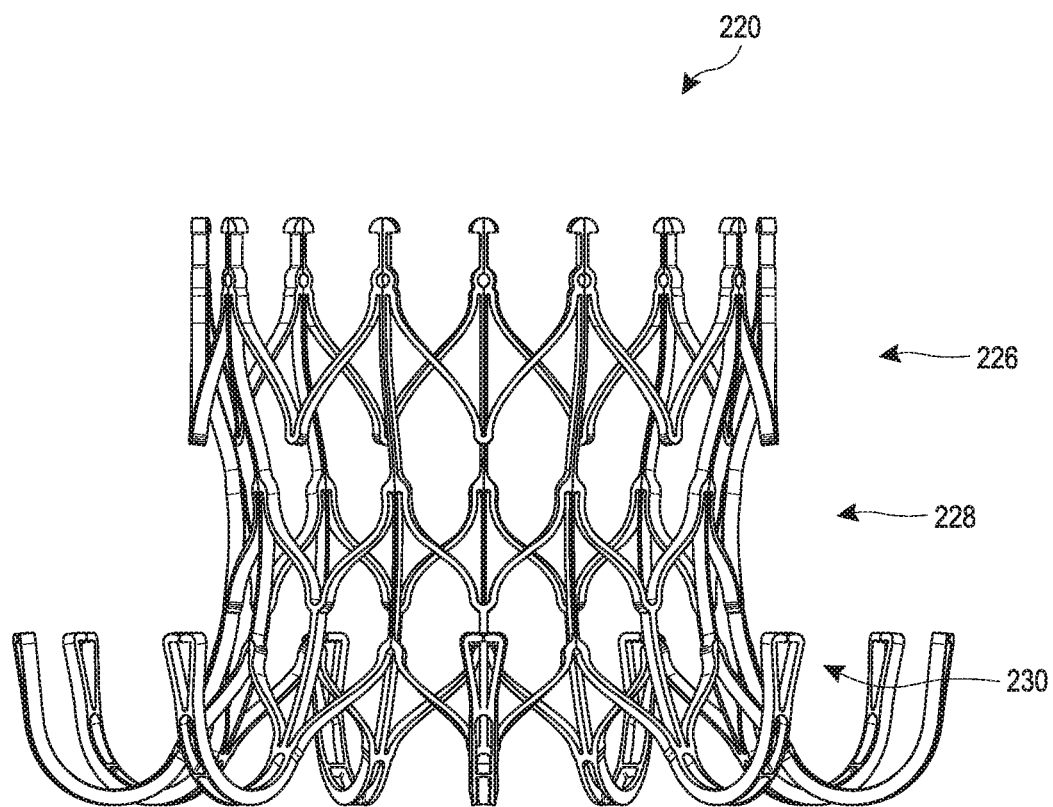
Figure 5D:
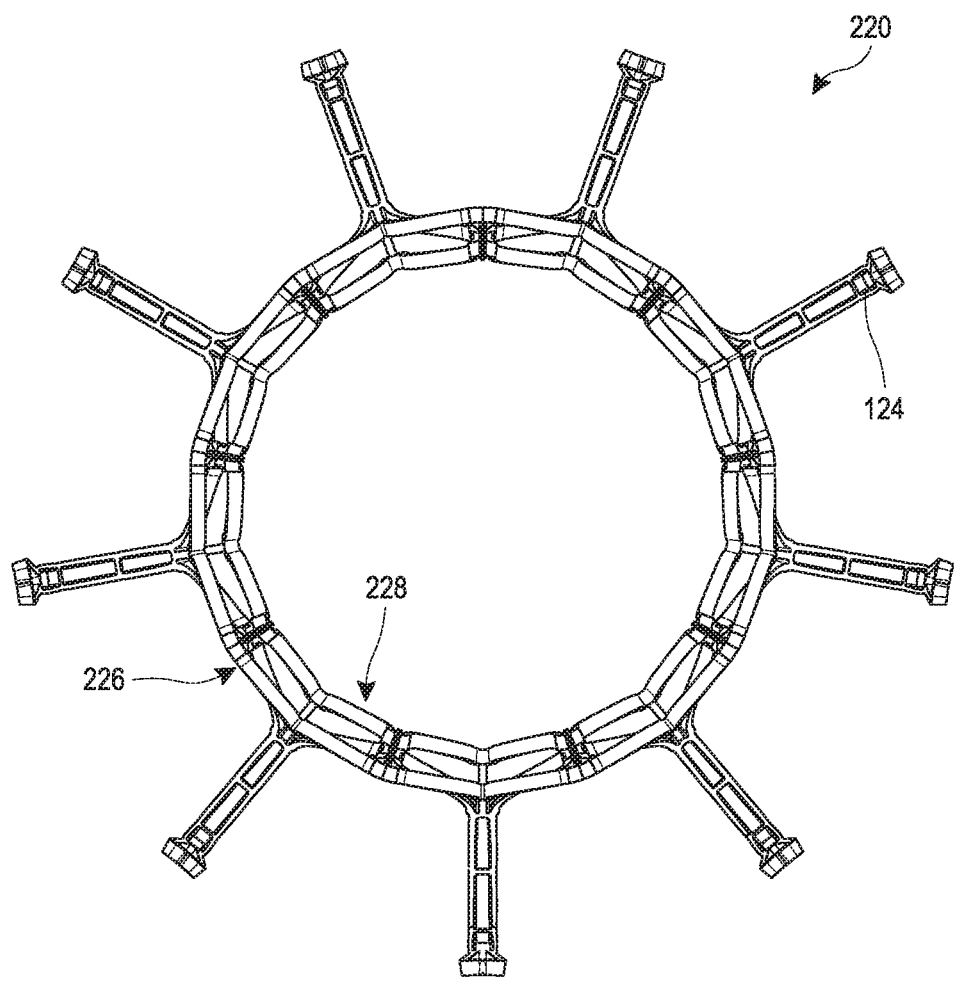
Figure 5E:
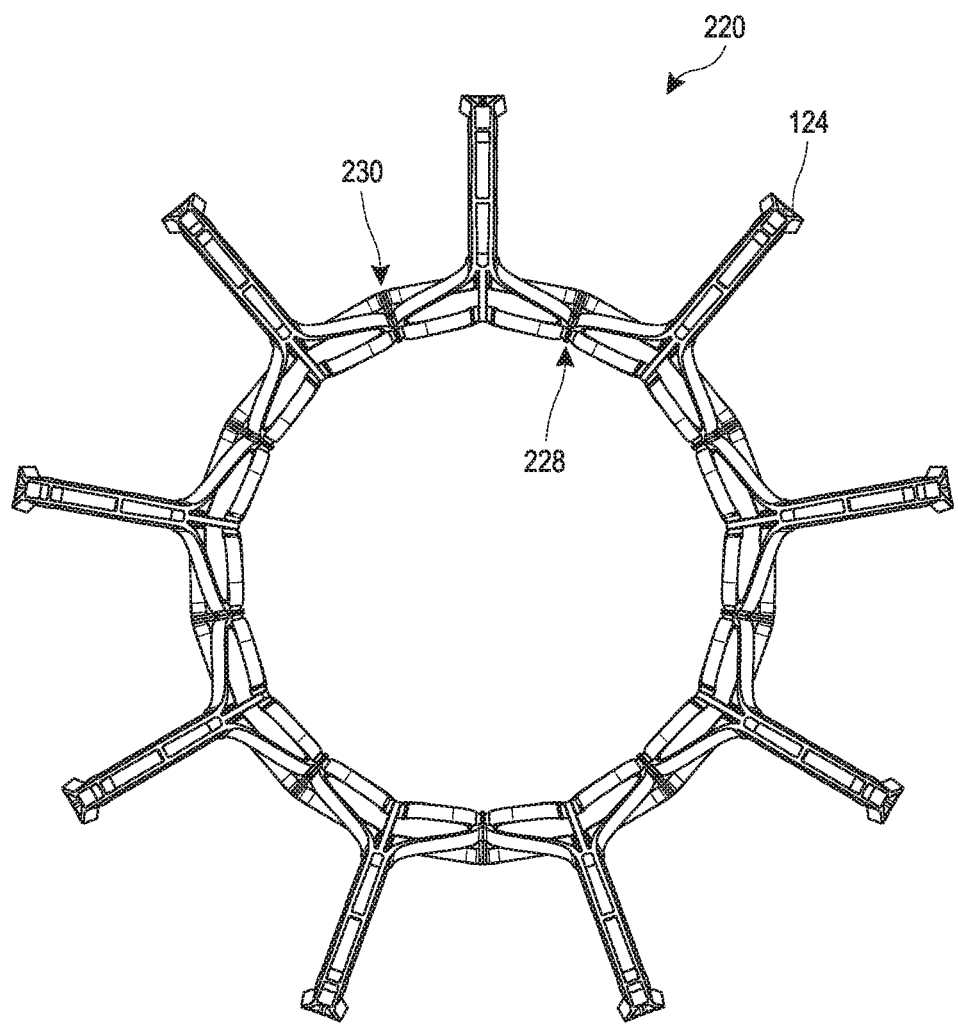
Figure 24:
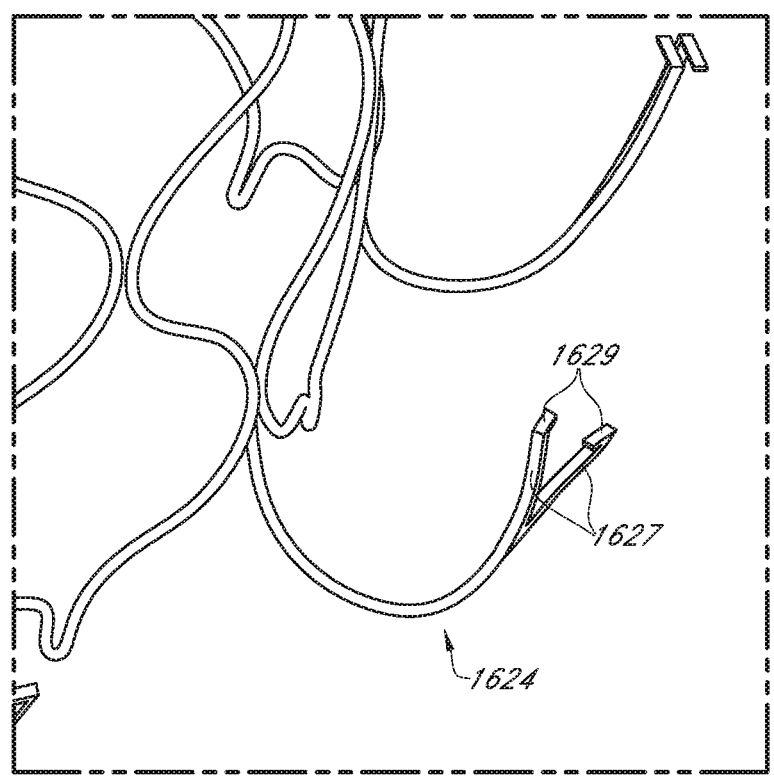
FIG. 24 show an embodiment of anchoring elements.

The tips or ends 124a as described above can advantageously provide atraumatic surfaces that may be used to contact or engage intralumenal tissue without causing unnecessary or undesired trauma to tissue. For example, the tips or ends 124a can form flat, substantially flat, curved or other non-sharp surfaces to allow the tips to engage and/or grasp tissue, without necessarily piercing or puncturing through tissue. A looped end or looped anchor, such as shown in FIG. 5A, may assist the frame in not getting caught up on structures at or near the treatment location. For example, each loop can be configured so that when the prosthesis 100 is deployed in-situ and the anchoring features 124a expands away from the frame bodies 122, the movement of each loop from a delivered position to a deployed position avoids getting caught on the papillary muscles. In some embodiments, the inner frame anchoring feature 124 can include a lacrosse-head-shaped tip or end 124a. In some embodiments, the tips or ends 124a of the inner frame 120 may have a split design such as shown in FIG. 24.

The anchoring features 124 can include nine individual anchors; however, it is to be understood that a greater number or lesser number of individual anchors can be used. For example, the number of individual anchors can be chosen as a multiple of the number of commissures for the valve body 160 (shown in FIG. 10). As such, for a prosthesis 100 with a valve body 160 having three commissures, the inner frame anchoring feature 124 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. It is to be understood that the number of individual anchors need not correspond to the number of commissures of the valve body 160. Moreover, while the prosthesis 100 includes anchoring features 124 with twelve anchors each, it is to be understood that a greater number of anchors or a lesser number of anchors can be used.

With reference to the inner frame 120 illustrated in FIGS. 9-11 and 17B, the inner frame anchoring feature 124 can include covers and/or cushions 138 to surround or partially surround at least a portion of the inner frame anchoring feature 124, such as the tips or ends 124a. The covers and/or cushions 138 can be similar to those described in U.S. Publication No. 2015/0328000, which is incorporated by reference herein in its entirety. The covers and/or cushions 138 can either fit snuggly around the tips 124a of the inner frame anchoring feature 124 or can have extra padding so that the covers extend radially away from the inner frame body 122. As shown in the illustrated embodiment, covers and/or cushions 138 are attached to a subset of anchors of the inner frame anchoring feature 124 such that a cover and/or cushion 138 is used on every third anchor. In some embodiments, the outer frame anchoring feature 144 can include covers and/or cushions to surround or partially surround at least a portion of the outer frame anchoring feature 144, such as the tips or ends 144a.

Figure 9:
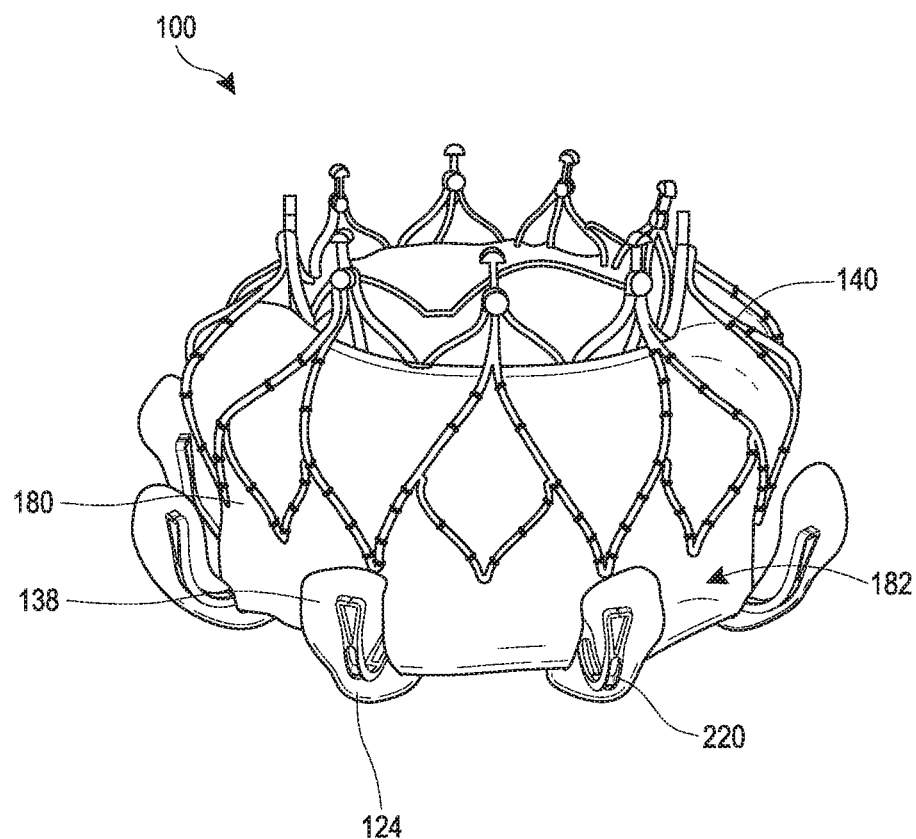
FIGS. 9-11 illustrate a multi-portion replacement prosthesis with an outer skirt.
Figure 10:
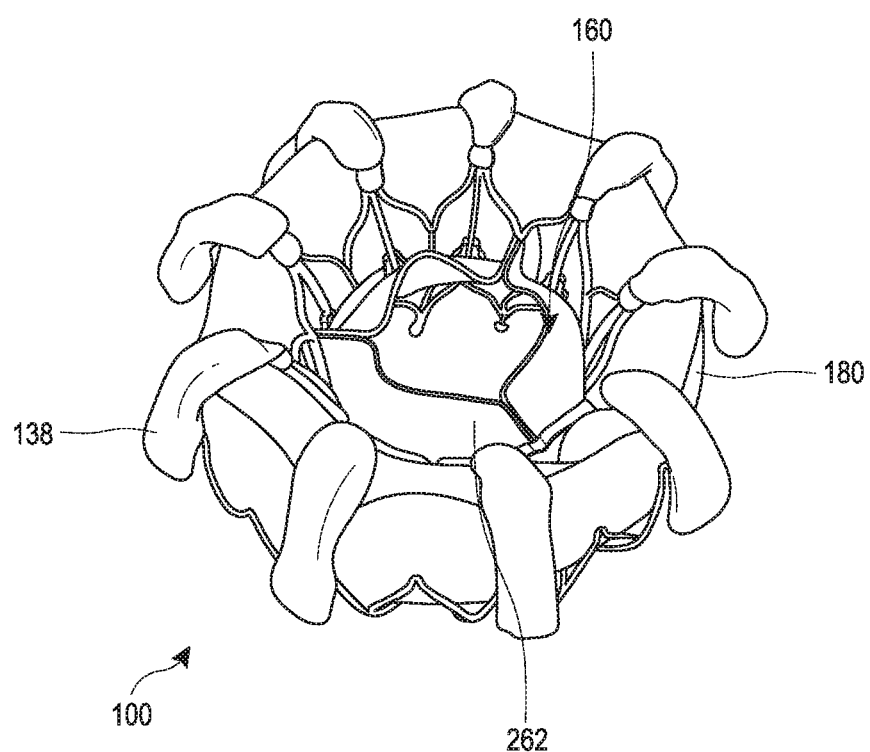
Figure 11:
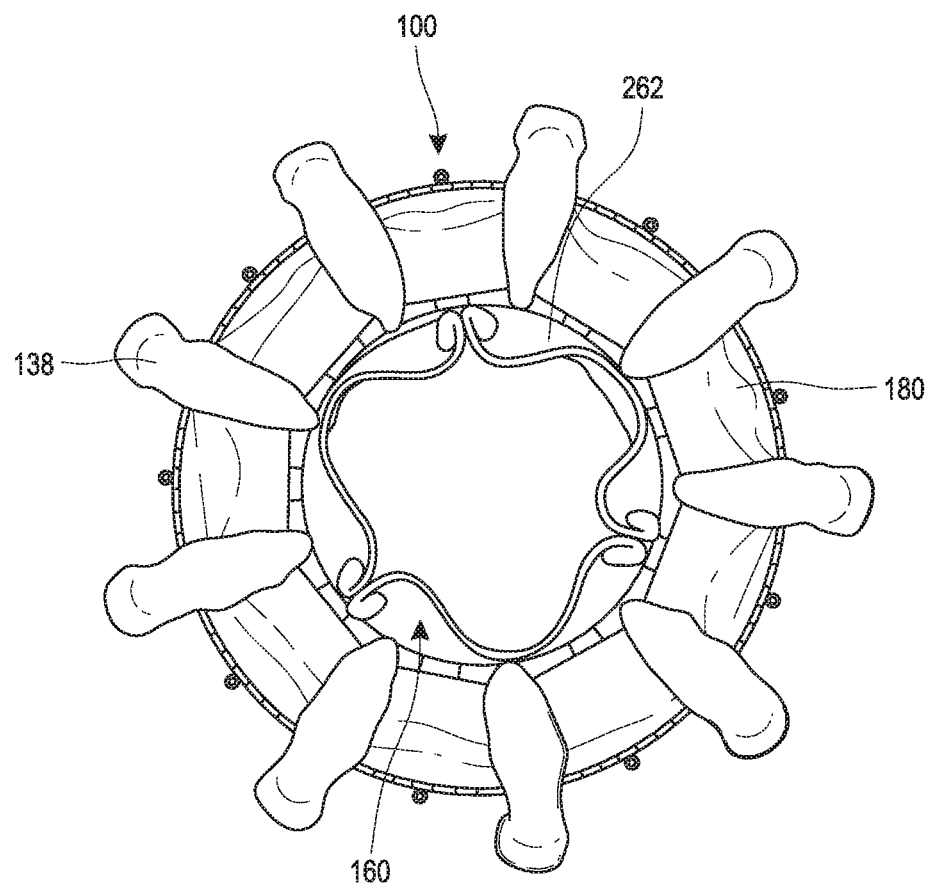

It is to be understood that greater or fewer numbers of covers and/or cushions 138 can be used with anchors of the inner frame anchoring feature 124. For example, a cover and/or cushion 138 can be used on every other anchor such that there is a 1:2 ratio of covers and/or cushions 138 to anchors. As another example, a cover and/or cushion 138 can be used on every anchor (as shown in FIGS. 9-11). In some embodiments, all of the anchors can have the covers and/or cushions with some of the anchors having less cushioning than others. In some embodiments, all of the anchors can have the padded covers. In other embodiments, all of the anchors can have the snuggly fitting cushions.

The cover and/or cushion 138 can be formed from a deformable material. When the top portion of the cover and/or cushion 138 is subject to pressure due to a downwardly directed force, the cover and/or cushion 138 can compress and expand laterally outward. Such a force may be exerted upon the cover and/or cushion 138, for example, when the cover and/or cushion 138 contacts a ventricular side of the mitral valve annulus during systole. The compression and lateral expansion of cover and/or cushion 138 can increase the surface area of the cover and/or cushion 138 in contact with the tissue, thereby exerting less pressure on the tissue and reducing the potential for trauma.

The inner frame 120 can be formed from many different materials including, but not limited to a shape-memory metal such as Nitinol. The inner frame 120 can be formed from a plurality of struts forming open cells, discussed below. In some embodiments, the inner frame 120 can have a relatively rigid construction as compared to other components of the prosthesis 100 including, but not limited to, the outer frame 140. This can be achieved, for example, by the dimensions of the struts and by the configuration of the struts. The relatively rigid construction can more strongly resist deformation when subject to stress. This can be beneficial during certain portions of the cardiac cycle, such as systole, during which the inner frame 120 may be subject to significant stresses on the inner frame anchoring feature 124. The relatively rigid construction can also be beneficial when a valve body 160 is positioned within the inner frame 120 to maintain the shape of the valve body 160. Moreover, the relatively rigid construction can be beneficial when the inner frame 120 is used for a valve-in-valve procedure wherein a supplemental prosthesis is positioned within the inner frame 120. However, although the inner frame 120 has been described as having a relatively rigid construction, it is to be understood that in some embodiments the inner frame 120 can have a construction relatively flexible construction. For example, the inner frame 120 can have a construction which is about as flexible as, or more flexible than, other components of the prosthesis 100, such as the outer frame 140.

The diameter of the upper region 126, intermediate region 128, and/or lower region 130 of the inner frame body 122 may be chosen such that the inner frame body 122 is adequately spaced from the body cavity when the prosthesis 100 is positioned within the body cavity. For example, in embodiments where the prosthesis 100 is positioned within the native mitral valve, the inner frame body 122 may have a diameter which is less than the diameter of the native mitral valve annulus. In situations where the native mitral valve annulus is about 40 mm in diameter, the diameter of the inner frame body 122 can be about 30 mm. Accordingly, the diameter of the inner frame body 122 may be about 75% of the diameter of the native mitral valve annulus.

In some embodiments, the diameter of the inner frame body 122 may be between about 40% to about 90% of the diameter of the native valve annulus, between about 60% to about 85%, of the diameter of the native valve annulus, between about 70% to about 80% of the diameter of the native valve annulus, any other sub-range between these ranges, or any other percentage as desired. In some embodiments, the diameter of the inner frame body 122 can be in the range of about 20 mm to about 40 mm when expanded, in the range of about 25 mm to about 35 mm when expanded, in the range of about 28 mm to about 32 mm when expanded, any other sub-range within these ranges when expanded, or any other diameter when expanded as desired. Although the inner frame body 122 has been described and illustrated as being cylindrical or having circular cross-sections, it is to be understood that all or a portion of the inner frame body 122 can be have a non-circular cross-section such as, but not limited to, a D-shape, an oval or an otherwise ovoid cross-sectional shape.

In other embodiments, the diameter of portions of the inner frame body 122 such as the upper region 126, intermediate region 128, and/or lower region 130 may be chosen such that the inner frame body 122 is positioned at the periphery of the body cavity. For example, in embodiments where the prosthesis 100 is positioned within the native mitral valve, the inner frame body 122 may have a diameter which is about equal to the diameter of the native mitral valve annulus.

Figure 4:
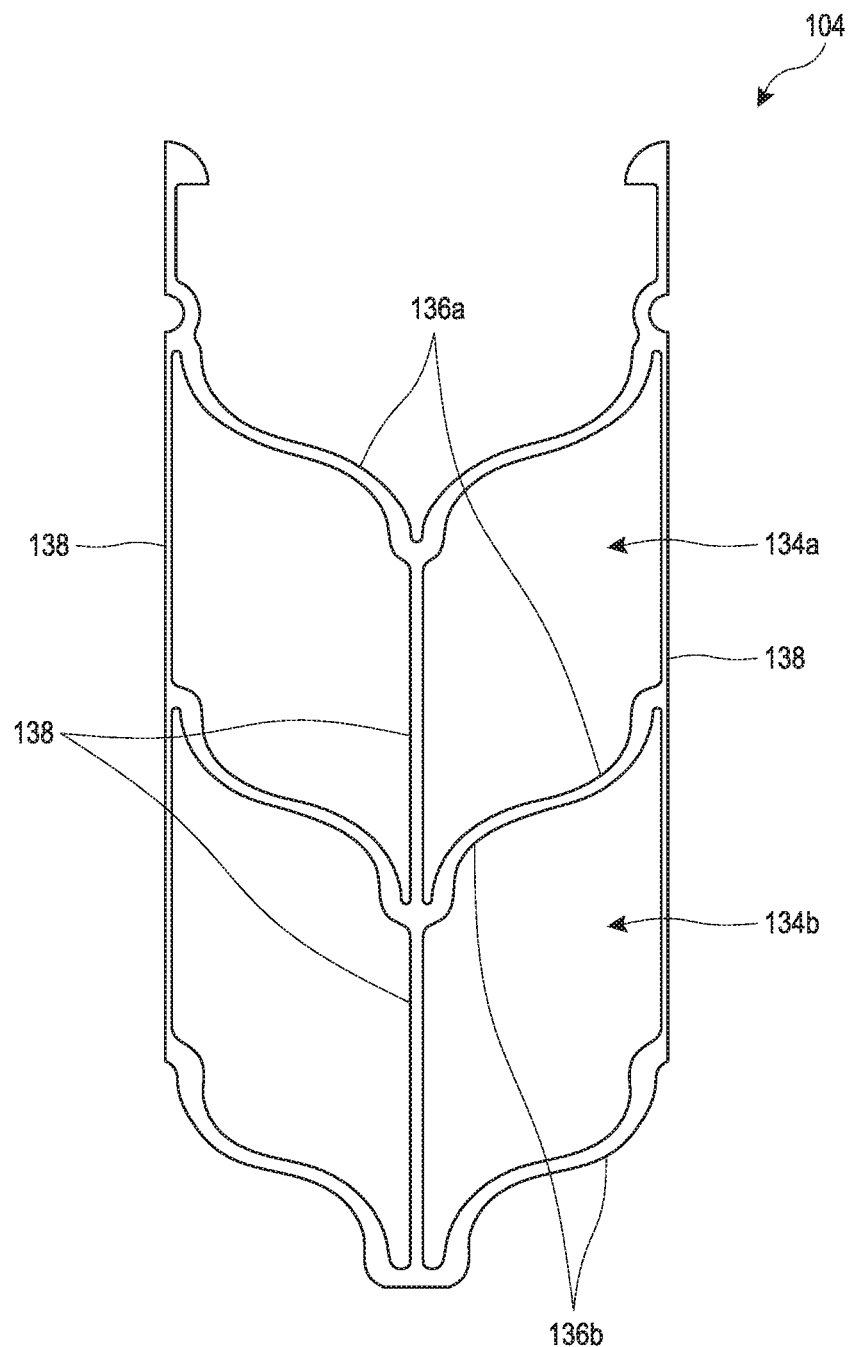
FIG. 4 illustrates a portion of the inner frame of FIG. 2.

FIG. 4 illustrates a portion of the inner frame body 122. As shown, the inner frame body 122 can include a plurality of struts with at least some of the struts forming cells 134a-b. Any number of configurations of struts can be used, such as rings of undulating struts shown forming ellipses, ovals, rounded polygons, and teardrops, but also chevrons, diamonds, curves, and various other shapes. The upper row of cells 134a and the lower row of cells 134b can have a diamond/parallelogram or generally diamond/parallelogram shape. The rows of cells 134a-b can be formed via a combination of struts. As shown in the illustrated embodiment, the upper row of cells 134a can be formed from a first set of circumferentially-expansible struts 136a at the top and bottom and a longitudinally extending strut 138. The lower row of cells 136b can be formed from the second set of circumferentially-expansible struts 136b on the top and bottom and a longitudinally extending strut 138 on each side, which can be a continuation of the longitudinally extending strut mentioned above. As shown, the upper row of cells 134a and the lower row of cells 136b can share one circumferentially-expansible strut. For example, the bottom strut of the upper row of cells 134a and the top strut of lower row of cells 136b may be shared. The first and second sets of struts 136a-b can have a zig-zag or undulating shape forming a repeating "V" shape. While the struts 136a-b are generally described and illustrated as being straight segments, it is to be understood that some or all of the struts 136a-b may not form entirely straight segments. For example, the struts 136a-b can include some curvature such that the upper and/or lower apices are curved as shown in FIG. 2.

Further, as shown in FIG. 4 the longitudinally extending strut 138 can generally extend from a bottom of the inner frame body 122 to a top of the inner frame body 122. Advantageously, the longitudinally extending strut 138 may effectively experience little to no strain during crimping. The longitudinally extending strut 138 may be one single strut extending through both rows of cells 134a/134b. Further, as shown each cell of the rows of cells 134a/134b can be circumferentially between longitudinally extending struts 138.

As shown in the illustrated embodiment, the upper row of cells 134a and the lower row of cells 134b extend in a direction generally parallel to the longitudinal axis of the prosthesis 100. There can be a row of eighteen cells 134a and a row of eighteen cells 134b. While each of the cells 134a-b are shown as having the same shape as other cells 134a-b of the same row but mirrored, it is to be understood that the shapes of cells 134a-b within a row can differ. Moreover, it is to be understood that any number of rows of cells can be used and any number of cells may be contained in the rows. In some embodiments, the number of cells can correspond to the number of anchors or anchor tips forming the inner frame anchoring feature 124. In some embodiments, both rows of cells 134a-b can have different numbers of cells. Moreover, it is to be understood that fewer or greater numbers of rows of cells can be used.

The geometry of cells 134a-b can allow the cells 134a-b to foreshorten as the inner frame 120 is expanded. As such, one or more of cells 134a-b can allow the inner frame 120 to foreshorten as the inner frame 120 is expanded. Foreshortening of the inner frame 120 can be used to secure the prosthesis to intralumenal tissue in a body cavity such as tissue at or adjacent a native valve including, but not limited to, a native valve annulus and/or leaflets. For example, expansion of the inner frame 120 can allow the inner frame anchoring feature 124 to extend radially outward and draw closer to tissue of the body cavity, such as a native valve annulus and/or leaflets, to engage tissue of the body cavity. In some embodiments, the use of longitudinally extending strut 138 can reduce the foreshortening.

Additionally, as shown in FIG. 2, the inner frame 120 can include tabs (or locking tabs) 104 extending from a portion of the inner frame 120. The tabs 104 can extend at or proximate an upper end of the upper region 126 of the inner frame body 122 such as upper apices of cells 134a. The inner frame 120 can include twelve locking tabs 104, however, it is to be understood that a greater number or lesser number of locking tabs can be used, such as 1, 2, 3, 4, 5, 6, 7, 8, 9, 10, or 11. The locking tabs 104 can extend generally upwardly from the upper region 126 of the inner frame body 122 in a direction generally aligned with the longitudinal axis of the prosthesis 100. As shown in the illustrated embodiment, the locking tabs 104 can include a longitudinally-extending strut 132a. At an upper end of the strut 132a, the locking tab 104 can include an enlarged head 132b. As shown, the enlarged head 132b can have a semi-circular or semi-elliptical shape forming a "mushroom" shape with the strut 132a.

In some embodiments, the inner frame 120 can include an eyelet 106. The eyelet 106 can be advantageously used to couple the inner frame 120 to an outer frame 140. For example, a suture can be passed through the eyelet 106 for coupling to an eyelet 143 of the outer frame 140. In some embodiments, the eyelet 106 can be used to couple to other components of a prosthesis in which the inner frame 120 is used such as, but not limited to, a valve body and/or a skirt.

While the locking tabs 104 have been described as being attached to the inner frame body 122, it is to be understood that the locking tabs 104 can be attached to other portions of the prosthesis 100 such as, but not limited to, the outer frame body 142. For example, in some embodiments, the locking tabs 104 can extend from an upper end of an upper region 146 of the outer frame body 142. Moreover, it is to be understood that portions of, or the entirety of, the locking tabs 104 can be omitted. For example, in some embodiments, the strut 132a can be omitted such that the enlarged head 132b and eyelet 106 are positioned at an upper end of the upper region 126 of the inner frame body 122, such as at upper apices of cell 134a.

In some embodiments, each tab 104 can be aligned vertically over an inner frame anchoring feature 124. In some embodiments, each tab 104 is circumferentially offset from an inner frame anchoring feature 124. In some embodiments, there are the same number of tabs 104 as inner frame anchoring features 124. In some embodiments, there are a different number of tabs 104 as inner frame anchoring features 124. There can be more tabs 104 than inner frame anchoring features 124. There can be less tabs 104 as inner frame anchoring features 124.

In some embodiments, the tab 104 can be advantageously used to couple the inner frame 120 with multiple types of delivery systems. For example, the shape of the tab 104 can be used to secure the inner frame 120 to a "slot" based delivery system. The eyelets 106 can be used to secure the inner frame 120 to a "tether" based delivery system such as those which utilize sutures, wires, or fingers to control delivery of the inner frame 120 and the prosthesis. This can advantageously facilitate recapture and repositioning of the inner frame 120 and the prosthesis in situ. In some embodiments, the inner frame 120 and prosthesis can be used with the delivery systems described herein, including but not limited to, those described in U.S. Pat. Nos. 8,414,644 and 8,652,203 U.S. Publication Nos. 2015/0238315, 2019/0008640, 2017/0056169, 2016/0317301 and 2017/0056171, the entireties of each of which have been incorporated by reference herein. In such embodiments, the tab 104 may be omitted to advantageously the axial dimension between the upper end and the lower end of the inner frame 120 (i.e., the "height" of the inner frame 120).

The inner frame 120, and any other frame described herein, may include features and concepts similar to those disclosed in U.S. Pat. Nos. 8,403,983, 8,414,644, and 8,652,203, U.S. Publication Nos. 2011/0313515, 2014/0277390, 2014/0277427, 2014/0277422, 2015/0328000, 2018/0021129, and 2018/0055629, the entireties of each of which are hereby incorporated by reference and made a part of this specification. This is inclusive of the entire disclosure and is not in any way limited to the disclosure of the associated frames. Moreover, although the inner frame 120 has been described as including an inner frame body 122 and an inner frame anchoring feature 124, it is to be understood that the inner frame 120 need not include all components. For example, in some embodiments, the inner frame 120 can include the inner frame body 122 while omitting the inner frame anchoring feature 124. Moreover, although the inner frame body 122 and the inner frame anchoring feature 124 have been illustrated as being unitarily or monolithically formed, it is to be understood that in some embodiments the inner frame body 122 and the inner frame anchoring feature 124 can be formed separately. In such embodiments, the separate components can be attached using any of the fasteners and/or techniques described herein. For example, the inner frame anchoring feature 124 can be formed separately from the inner frame body 122 and can be attached to the inner frame body 122.

FIGS. 5A-5E illustrates an inner frame 220 with an "hourglass" or generally hourglass shape. A full multi-portion replacement valve with an hourglass inner frame is shown with respect to FIGS. 30A-30D. The inner frame 220 can incorporate any or all of the features discussed above with respect to inner frame 120, for example inner frame anchoring feature 124, and the inner frame 120 can incorporate any or all of the features discussed above with respect to inner frame 220. Inner frame 220 can include an upper region 226, an intermediate region 228, and a lower region 230. As shown, the intermediate region 228 can have a smaller diameter than the upper region 226, the lower region 230, or both. This can form an hourglass shape wherein the intermediate region 228 is thinner in diameter than both the upper region 226 and the lower region 230. In some embodiments, the upper region 226 and the lower region 230 can have approximately the same diameter. In some embodiments, the upper region 226 can have a larger diameter than the lower region 230. In some embodiments, the upper region 226 can have a smaller diameter than the lower region 230.

FIGS. 5A-5E further illustrates that the inner frame 220 can smoothly transition between the different diameters forming a curved shape. In some embodiments, the struts making up the inner frame 220 can be curved to form the hourglass. In some embodiments, the struts can be relatively straight, and there can be inflection points in the struts or at meeting points between the struts. In some embodiments, the inner frame 220 can be concave. In some embodiments, a portion of the inner frame 220, such as the upper region 226, the intermediate region 228, and/or the lower region 230 may be concave. In some embodiments, the inner frame 220 can curve inward, or be thinner, in the middle than at the top and bottom. In some embodiments, the inner frame 220 can form the hourglass shape in its fully expanded form. In some embodiments, an hourglass can be shaped from a linear radially inwards taper from the upper region 226 to the intermediate region 228 (so the diameter is smaller at the intermediate region 228 than the upper region 226) and a subsequent radially outwards taper (e.g., reversing the taper) from the intermediate region 228 to the lower region 230 (so the diameter is smaller at the intermediate region 228 than the lower region 230). In some embodiments, the frame 220 may have a tapered waist or a narrowed waist.

In some embodiments, the inner frame 220 can taper radially inwards (e.g., reducing diameter) in one direction from one end to the other end. For example, the upper region 226 may have the largest diameter, and the inner frame 220 can taper radially inwards to the intermediate region 228, and further radially inwards to the lower region 230. In some embodiments, the lower region 230 may have the largest diameter, and the inner frame 220 can radially inwards to the intermediate region 228, and further radially inwards to the upper region 226. The taper may be smooth, or may be a series of straight portions, like steps. In some embodiments, the taper may occur in 1, 2, 3, 4, 5 straight lines reducing the diameter. In some embodiments, the taper may be curved. In some embodiments, the taper may be linear.

In some embodiments, a portion of the inner frame 220 may be tapered radially inwards, and a different portion may be cylindrical (or generally cylindrical). For example, the upper region 226 may be tapered radially inwards, but the intermediate region 228 and/or the lower region 230 may be cylindrical. In some embodiments, the lower region 230 may be tapered radially inwards, but the intermediate region 228 and/or the upper region 226 may be cylindrical.

In some embodiments, a portion of the inner frame 220 may be tapered radially inwards, and a different portion may be concave (or generally concave). For example, the upper region 226 may be tapered radially inwards, but the intermediate region 228 and/or the lower region 230 may be generally. In some embodiments, the lower region 230 may be tapered radially inwards, but the intermediate region 228 and/or the upper region 226 may be generally.

The hourglass shape and/or tapering described above can allow for the leaflets of the valve to be "flush" against the inner frame 220 when opened. Further, the longitudinal length of the leaflets can be against the inner frame 220 as much as possible. For example, each of the valve leaflets can have an inlet end positioned along the decreasing diameter portion of the frame as discussed above. Additionally, the narrower intermediate region 228 can provide for smaller replacement valve leaflets to be used, and the smaller diameter can allow for increased blood flow through the narrower area.

Embodiments of the inner frame 220 can advantageously reduce thrombogenicity. For example the hourglass shape can help create a vortex which encourages particles to be washed-out during valve opening with high turbulence during closing. This can also include squeezing out any thrombus that may be forming in the gap between leaflets and the frame 220. In addition, this shape can reduce leaflet thickening, which can cause increased risk of stroke. This can allow for the reduction or avoidance of blood thinners, or at least the avoidance of lifetime blood thinners. This could clinically lead to less anticoagulation, better durability, and lower stroke.

Figures 5F, 5G:
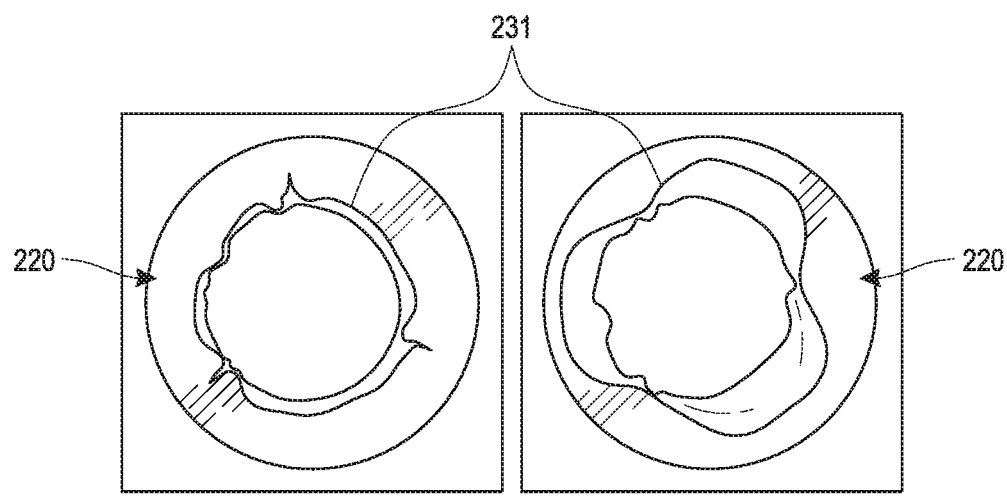
FIGS. 5F-5I illustrate leaflets opening in a frame having an hourglass shape such as shown in FIGS. 5A-5E.
Figures 5H, 5I:
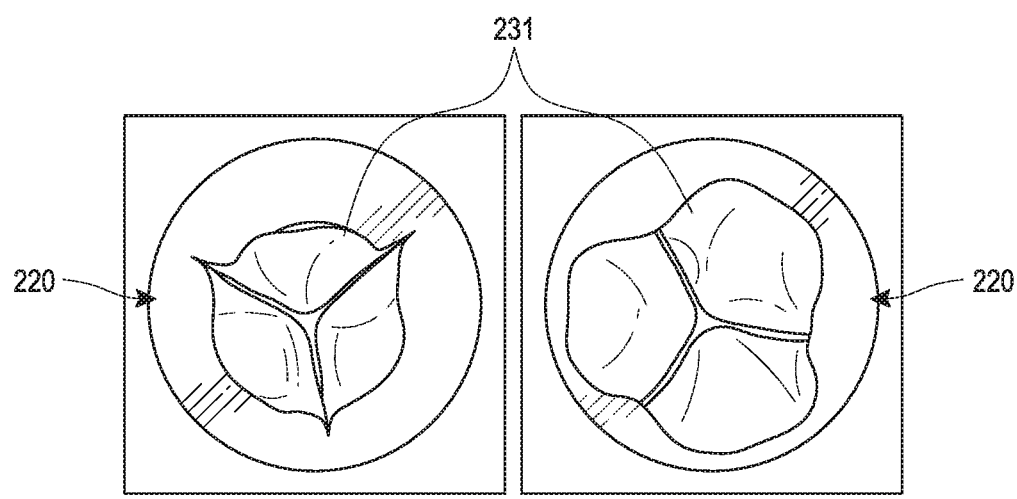

FIGS. 5F-5I illustrate the valve leaflets 231 opening in an hourglass shaped frame 220. FIG. 5F shows the outflow end open, FIG. 5G shows the inflow end open, FIG. 5H shows the outflow end closed, and FIG. 5I shows the inflow end closed. In some embodiments, the inlet end of the valve leaflets 231 can lie flat along the inner frame 220 when the valve is open. Thus, if the inner frame 220 is in a cylindrical frame, the valve leaflets 231 may not be parallel to the walls of the frame because the leaflets 231 naturally are inclined outwards in the opened position, causing compression or distortion of the leaflets. However, using the inner frame 220 shapes described above (an hourglass, tapered, concave or similar shape) where the valve leaflet 231 inlets are, then the valve leaflets 231 more naturally rest closer to the frame 220 itself when the valve is open as shown in FIGS. 5F and 5G, and do not compress or deform. Thus, the leaflets 231 follow the shape of the hourglass frame 220 when opening, providing for optimal washout. In some embodiments, the leaflets 231 can be attached generally at the intermediate region 228, so when the leaflets 231 are opened they can extend further radially outwards in the larger diameter regions.

Figure 5J:
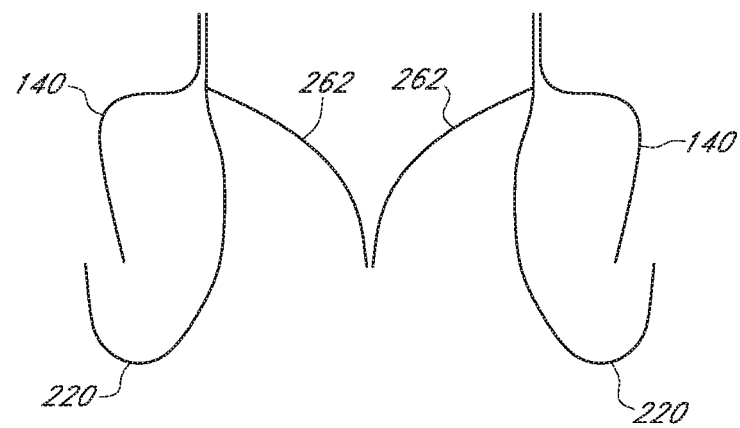
FIGS. 5J-5K illustrate a cross section of leaflets in open and closed positions in a frame having an hourglass shape such as shown in FIGS. 5A-5E.
Figure 5K:
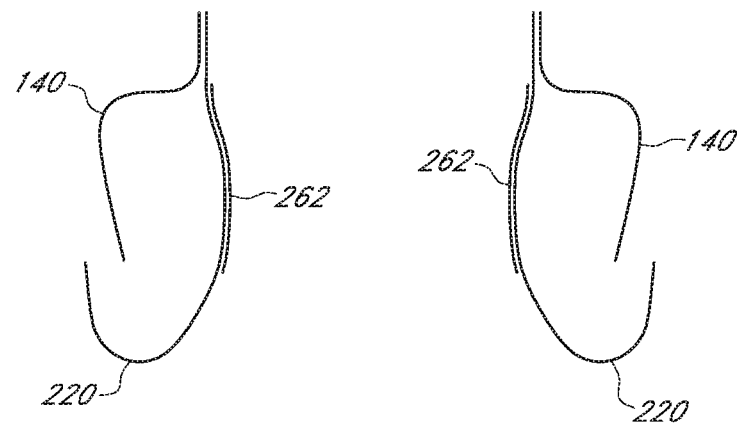
Figure 6A:
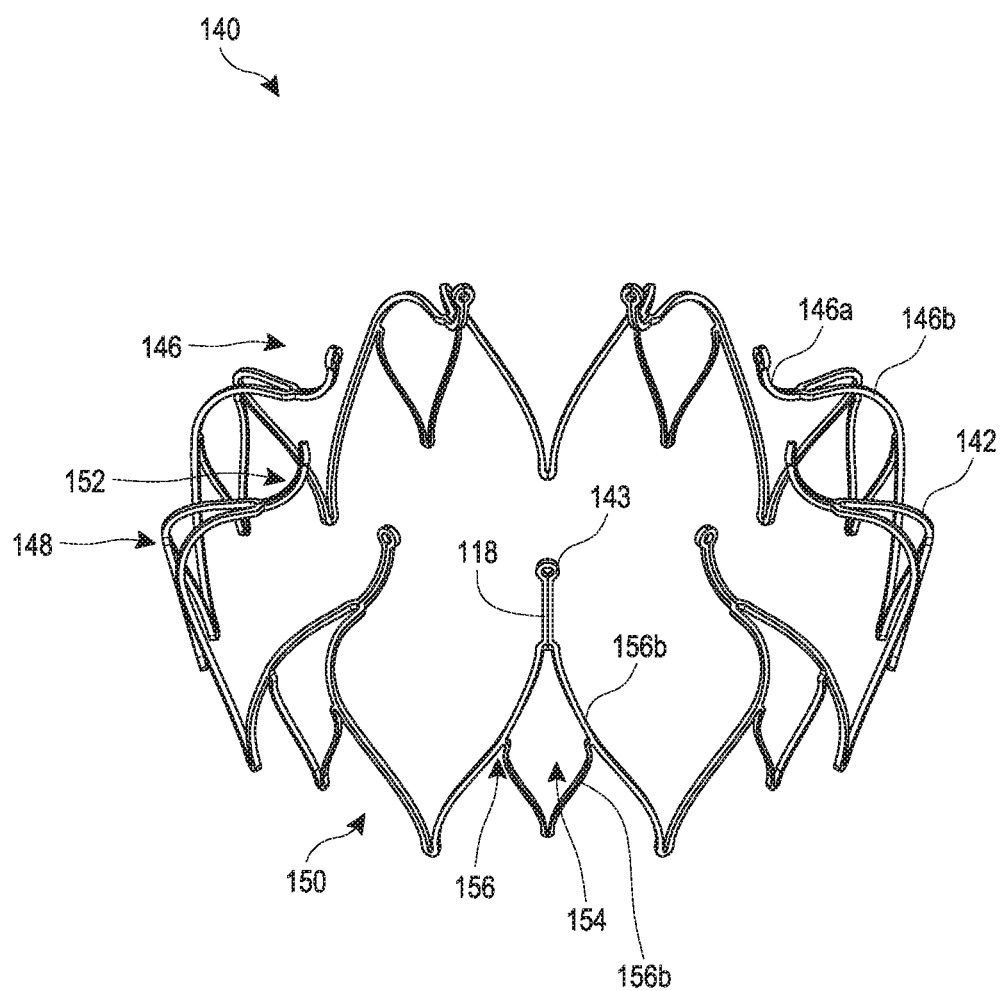
FIGS. 6A-6D illustrate an embodiment of an outer frame of the multi-portion replacement prosthesis shown in FIG. 1.
Figure 6B:
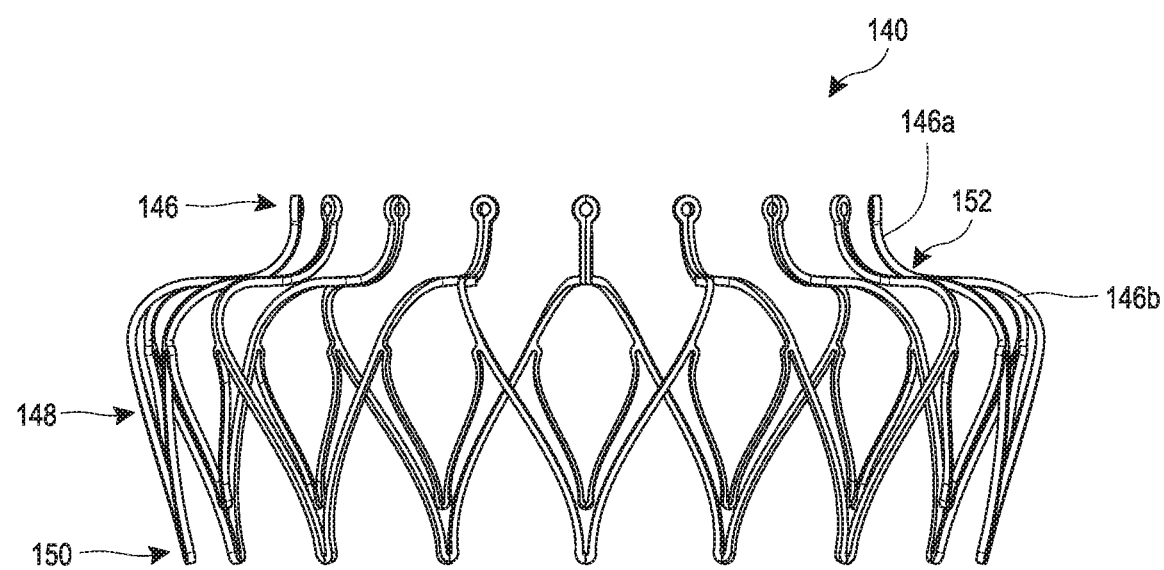
Figure 6C:
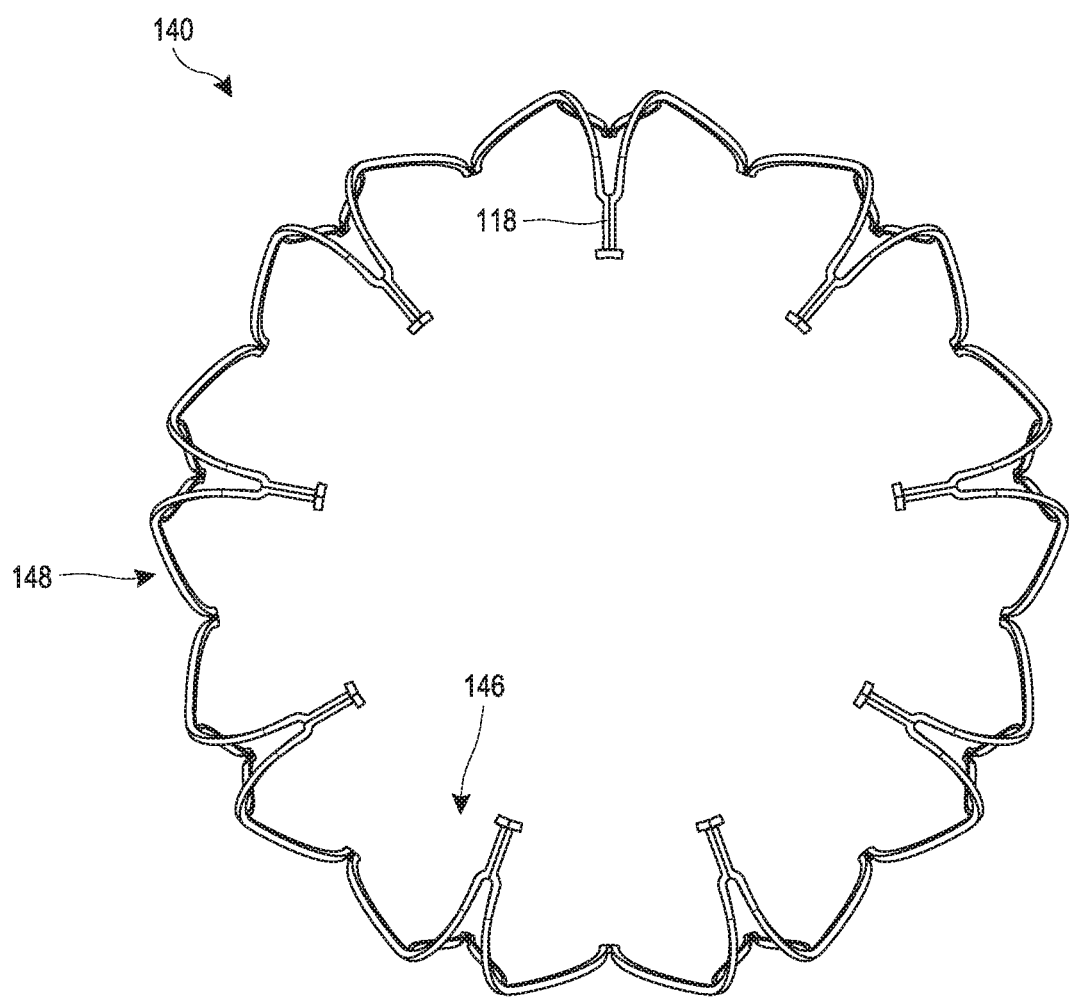
Figure 6D:
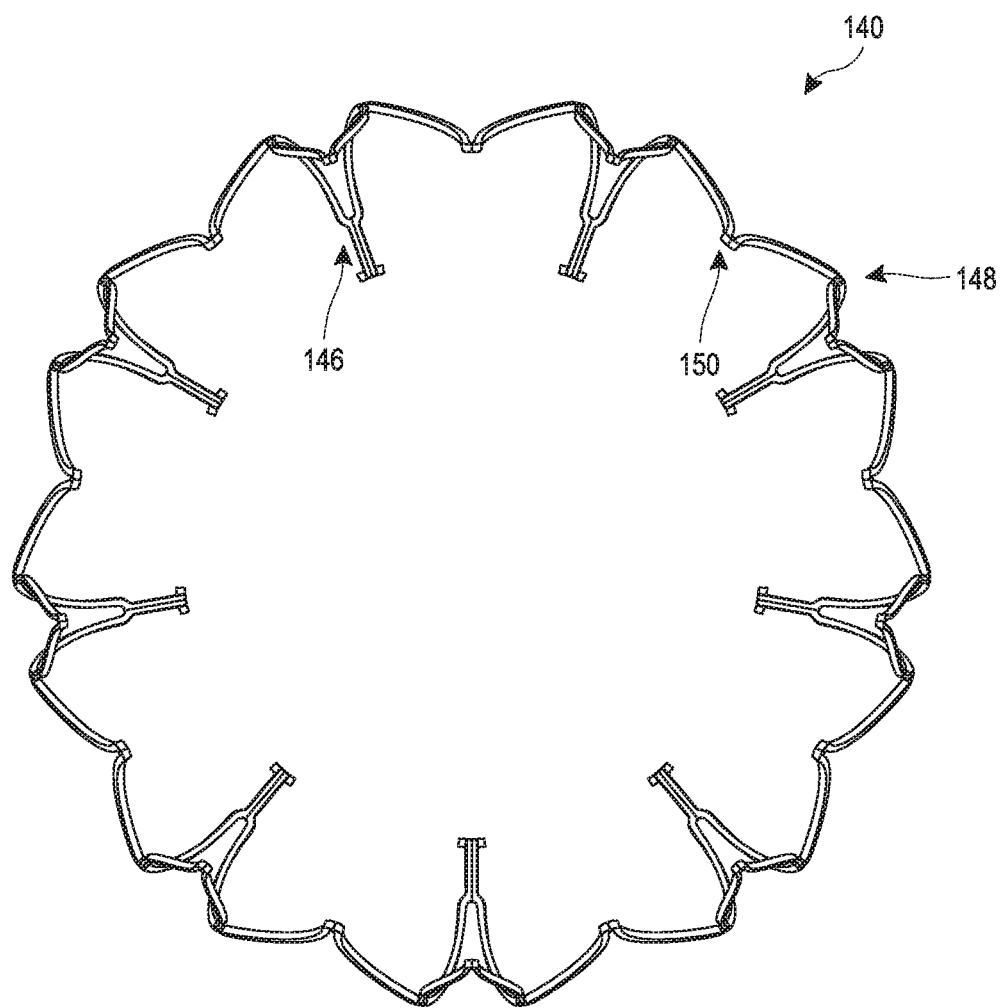

Further, the hourglass inner frame 220 can allow for the leaflets of the valve body to conform with and/or contact the inner surface of the hourglass inner frame 220. Thus, the hourglass design can improve washout by reducing any gap between the seamline of the leaflets and the wall of the inner frame 220 on which the leaflets are attached to. Specifically, FIG. 5J shows the leaflets 262 in the closed position and FIG. 5K shows the leaflets 262 in the fully open position generally conforming to the inner frame 220. Thus, as shown, in some embodiments the only portions of each of the leaflets 262 that do not contact the frame 220 when opened are the free edges of the leaflets 262 at the outlet end. Accordingly, almost the entire "belly" or "surface" of each of the leaflets 262 (e.g., the surface of the leaflets 262 which face the interior surface of the inner frame 220) conform to and/or contact the inner frame 220 of the hourglass shape (e.g., reducing any gap between the leaflets 262 and the interior surface of the inner frame 220). In some embodiments, over 50%, over 75%, over 90%, over 95%, or over 99% of the belly of the leaflets 262 can conform to and contact the interior surface of the inner frame 220 when in the fully open position. In some embodiments, the free edges of the outlet end of the leaflets 262 do not contact the inner frame 220. In some embodiments, only the free edges of the outlet end of the leaflets 262 do not contact the inner frame 220. In some embodiments, the free edges of the outlet end of the leaflets 262 are spaced away from the interior surface of the inner frame 220.

This configuration can be advantageous as free edges contacting the frame can create major durability issues, as constant opening and closing can wear on the edges and damage/destroy them. Thus, advantageously the hourglass inner frame 220 is shaped to achieve optimal contact between the leaflet surface and the frame surface when the leaflets 262 are fully opened while avoiding contact by the free edges to reduce overall damage to the leaflets during motion. This can improve washout and reduce thrombogenicity, while also providing a more durable leaflet.

While the hourglass and tapering shape is described above in conjunction with the inner frame 220, similar dimensions/shapes can be used with respect to the outer frame 140 or a single frame prosthesis. Further, this can be applied to any type of valve, such as a replacement mitral valve or a replacement aortic valve.

Figure 31:
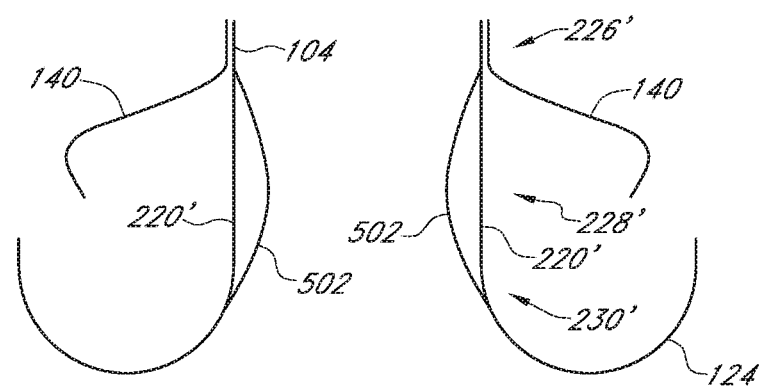
FIG. 31 illustrates an alternate embodiment of an inner frame with a secondary inner frame having an hourglass shape.

FIG. 31 illustrates an example alternate configuration of the hourglass shape discussed above for the inner frame 220, and can include any or all of the features discussed with respect to frames 120/220 shown in FIGS. 2 and 5A. Instead of the inner frame 220' being an hourglass shape as discussed above with respect to inner frame 220, the inner frame 220' can have a non-hourglass cylindrical shape such as shown in FIG. 2 between its upper region 226', intermediate region 228', and lower region 230', as shown in FIG. 31. For example, the inner frame 220' can have a substantially constant cross-sectional dimension, e.g., generally circular, between its upper region 226', intermediate region 228', and lower region 230'. An additional secondary inner frame 502 can then be attached (permanently or removably) on an inner surface of the inner frame 220'. The secondary inner frame 502 can have a generally circular cross section.

The secondary inner frame 502 can be shaped to form an hourglass within the lumen of the inner frame 220'. For example, an intermediate region 288' can have a smaller radial diameter than the upper region 226' and the lower region 230'. In some embodiments, the upper region 226' and the lower region 230' can have approximately the same dimensions. In other embodiments, the dimensions may be different. In some embodiments, the transition between different diameters can be smooth, such as with a curve, or can be angular with discrete corners. The secondary inner frame 502 can have a concave shape.

As shown in FIG. 31, the secondary inner frame 502 can attach generally at proximal (e.g., in the upper region 226') and distal (e.g., in the lower region 230') ends of the secondary inner frame 502, and a central portion of the secondary inner frame 502 can be located radially inwards from the ends and from the inner surface of the inner frame 220'.

In some embodiments, a proximal portion of the secondary inner frame 502 can be attached to the inner frame 220' proximal to where the tabs 104 begin. In some embodiments, a proximal portion of the secondary inner frame 502 can be attached to the inner frame 220' distal to where the tabs 104 begin. In some embodiments, a proximal portion of the secondary inner frame 502 can be attached to the inner frame 220' where the tabs 104 begin.

In some embodiments, a distal portion of the secondary inner frame 502 can be attached to the inner frame 220' proximal to where the inner frame anchoring feature 124 begins bending radially outwards. In some embodiments, a distal portion of the secondary inner frame 502 can be attached to the inner frame 220' distal to where the inner frame anchoring feature 124 begins bending radially outwards. In some embodiments, a distal portion of the secondary inner frame 502 can be attached to the inner frame 220' where the inner frame anchoring feature 124 begins bending radially outwards.

The secondary inner frame 502 can be attached to the inner frame 220' by, for example, sutures, adhesives, frictional forces, mechanical attachment, or the two frames can be integrally formed together.

The secondary inner frame 502 can be an "ultra-thin walled" inner frame, such as between 200-400 microns of thickness, though the particular size is not limiting. For example, the secondary inner frame 502 may be formed of a plurality of longitudinal strips (e.g., ribs), for example metallic, composite, or polymer strips. The strips could bow inwardly as the inner frame 220' foreshortens upon radial expansion. In some embodiments, the strips could always be bowed inwardly. In some embodiments, the strips could be used in combination with a fabric or polymer. Thus, the secondary inner frame 502 could generally be a tube of fabric with a plurality of ribs on the outside of the fabric that would push the fabric inwardly to form the hourglass shape. Alternatively, a thin braided mesh which can bow inwardly, such as during foreshortening, could be used in conjunction with a fabric as discussed above.

In some embodiments, a cloth or other fabric can be used to form the hourglass shape. For example, the cloth could act as a pocket that would fill with blood and harden over time into the particular hourglass shape. Alternatively, a balloon could be used to form the hourglass shape where the balloon could be filed with saline or other biocompatible fluid.

In some embodiments, a swellable material could be used to form the secondary inner frame 502. The swellable material could absorb water, or other fluid, from blood and swell into the desired shape.

The secondary inner frame 502 can be advantageous as it leverages the highly stable cylindrical inner frame design of inner frame 220' while still providing the anti-thrombosis benefit of the hourglass secondary inner frame 502.

Outer Frame

With reference next to the outer frame 140 which is illustrated alone in FIGS. 6A-6D. The outer frame 140 can be incorporated into a prosthesis with any of the variations of the described inner frames. The outer frame 140 can provide a structure to which various components of the prosthesis 100 can be attached. The outer frame 140 can be attached to the inner frame 120 using any of the fasteners and/or techniques described herein including, but not limited to, mechanical fasteners, such as sutures, staples, fabric screws, rivets, interfacing members (e.g., tabs and slots which can be on the inner frame 120 and the outer frame 140), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. In some embodiments, the inner frame 120 and the outer frame 140 can be indirectly attached via an intermediate component, such as the skirt 180. In some embodiments, sutures are used to attached eyelet 143 of the outer frame 140 with eyelet 106 of the inner frame 120.

The outer frame 140 can be attached to the inner frame 120 at one or more attachment points. The outer frame 140 can be tautly attached to the inner frame 120 such that little to no relative movement between the outer frame 140 and the inner frame 120 occurs at the one or more attachment points. In other embodiments, the outer frame 140 can be loosely attached to the inner frame 120 such that some relative movement between the outer frame 140 and the inner frame 120 can occur at the one or more attachment points. Although the outer frame 140 is illustrated as a separate component from the inner frame 120, it is to be understood that the frames 120, 140 can be unitarily or monolithically formed.

Figure 12:
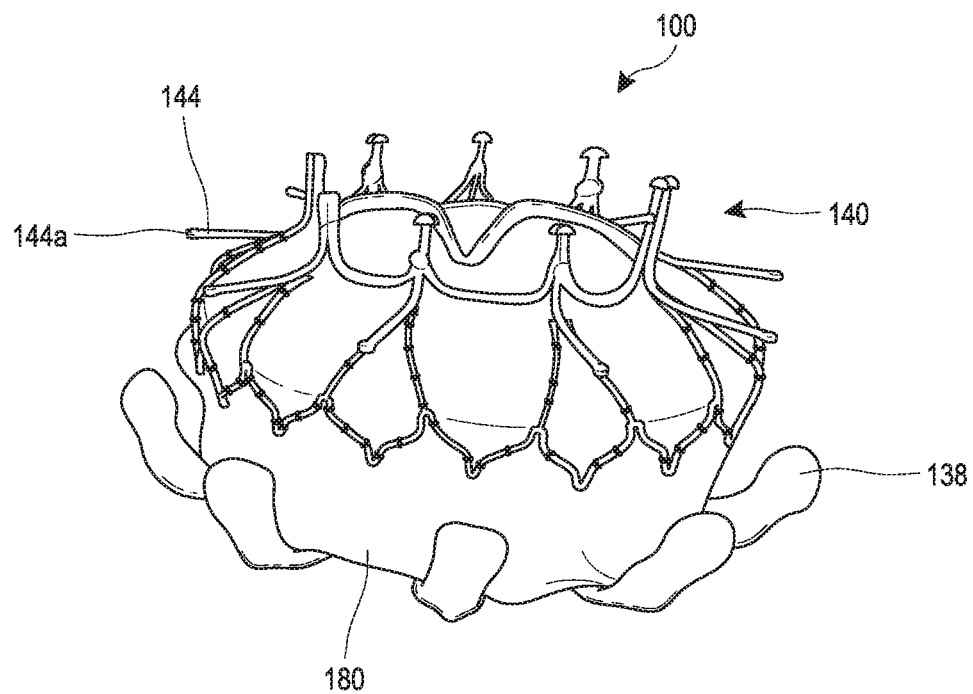
FIG. 12 illustrate a multi-portion replacement prosthesis having outer frame anchoring features.

As shown in the illustrated embodiment, the outer frame 140 can include an outer frame body 142. In some embodiments, such as shown in FIG. 12, the outer frame 140 can further include an outer frame anchoring feature 144 (if used in a mitral valve, also known as an atrial or proximal anchor). However, as shown in FIGS. 6A-6D (and FIGS. 9-11), the outer frame may not include an outer frame anchoring feature 144.

The outer frame body 142 can have an upper region 146, an intermediate region 148, and a lower region 150. In some situations, such as those in which the prosthesis 100 is positioned within a native mitral valve, the upper region 146 can be generally positioned supra-annularly, the intermediate region 148 can be generally positioned intra-annularly, and the lower region 150 can be positioned sub-annularly. However, it is to be understood that in some situations, the positioning of the outer frame 140 relative to the annulus can differ. Moreover, it is to be understood that in some embodiments, the outer frame 140 can omit one or more of the upper region 146, the intermediate region 148, and/or the lower region 150.

When in an expanded configuration such as a fully expanded configuration, the outer frame body 142 can have an enlarged/bulbous shape with the intermediate region 148 and the lower region 150 being larger than the upper region 146, or the intermediate region 148 being larger than the lower region 150 and the upper region 146. The bulbous shape of the outer frame body 142 can advantageously allow the outer frame body 142 to engage a native valve annulus, native valve leaflets, or other body cavity, while spacing the inlet and outlet from the heart or vessel wall. This can help reduce undesired contact between the prosthesis 100 and the heart or vessel, such as the atrial and ventricular walls of the heart. The bulbous shape can further enhance securement of the outer frame body 142 to the body cavity. For example, in some embodiments, the bulbous shape can allow the intermediate region 148 to extend further radially outward compared to an anchoring feature. In this manner, the intermediate region 148 can exert a greater radial force on tissue of the body cavity and/or can more completely conform to the tissue of the body cavity, such as the native valve annulus and/or native leaflets.

The upper region 146 of the outer frame body 142 can include a generally longitudinally-extending section 146a and an outwardly-extending section 146b. The longitudinally-extending section 146a can be generally concentric with the inner frame body 122. The outwardly-extending section 146b can extend radially outwardly away from the longitudinal axis 102 of the prosthesis 100. The outwardly-extending section 146b can extend in a direction that is more perpendicular to the longitudinal axis 102 than parallel and/or in a downward direction from the longitudinally-extending section 146a. However, it is to be understood that the outwardly-extending section 146b can extend generally perpendicularly to the longitudinal axis 102 and/or in an upward direction from the longitudinally-extending section 146a. Moreover, it is to be understood that the longitudinally-extending section 146a can be omitted such that the upper region 146 extends radially outwardly at the upper end of the upper region 146.

At the juncture between the longitudinally-extending section 146a and the outwardly-extending section 146b, the outer frame body 140 can include a bend 152. The bend 152 can be about a circumferential axis such that the outwardly-extending section 146b extends in a direction more perpendicular to the longitudinal axis of the outer frame 140 than the longitudinally-extending section 146a. In some embodiments, the bend 152 can generally form an arc with an angle between about 20 degrees to about 90 degrees. For example, as shown in the illustrated embodiment, the arc can have an angle of about 60 degrees. In some embodiments, the bend 152 can form an arc with an angle between about 30 degrees to about 60 degrees. The radius of curvature of the arc may be constant such that the bend 152 forms a circular arc or may differ along the length of the bend 152.

In some embodiments, the outwardly-extending section 146b can form an angle of between about 20 degrees to about 70 degrees with a plane orthogonal to the longitudinal axis of the prosthesis 100, an angle of between about 30 degrees to about 60 degrees with a plane orthogonal to the longitudinal axis of the prosthesis 100, an angle of between about 40 degrees to about 50 degrees with a plane orthogonal to the longitudinal axis of the prosthesis 100, an angle of about 45 degrees with a plane orthogonal to the longitudinal axis of the prosthesis 100, any subrange within these ranges, or any other angle as desired. In some embodiments, the outwardly-extending section 146b can form an angle of less than 70 degrees with a plane orthogonal to the longitudinal axis of the prosthesis 100, an angle of less than 55 degrees with a plane orthogonal to the longitudinal axis of the prosthesis 100, an angle of less than 40 degrees with a plane orthogonal to the longitudinal axis of the prosthesis 100, an angle of less than 25 degrees with a plane orthogonal to the longitudinal axis of the prosthesis 100, or less than any other angle as desired.

The intermediate region 148 of the outer frame body 142 can extend generally downwardly from the outwardly-extending section 146b of the upper region 146. As shown, the intermediate region 148 can have a generally constant diameter from an upper end of the intermediate region 148 to a lower end of the intermediate region 148 such that the intermediate region 148 forms a generally cylindrical shape. However, it is to be understood that the diameters of the upper end, the lower end, and/or the portion therebetween can be different. For example, a diameter of the portion between the upper end and the lower end can be larger than the upper end and the lower end such that the intermediate region 148 has a generally bulbous shape. In some embodiments, the diameter of the lower end can be larger than the diameter of the upper end. In other embodiments, the diameter of the upper end can be larger than the diameter of the lower end. Moreover, although the outer frame body 142 has been described and illustrated as being cylindrical or having circular cross-sections, it is to be understood that all or a portion of the outer frame body 142 can be have a non-circular cross-section such as, but not limited to, a D-shape, an oval or an otherwise ovoid cross-sectional shape.

In some embodiments, the lower region 150 can be curved and/or inclined towards the longitudinal axis of the frame such that the lower ends of the lower region 150 can extend in a direction that is between about 20 degrees to about 80 degrees with respect to a plane parallel to the longitudinal axis, between about 25 degrees to about 70 degrees with respect to a plane parallel to the longitudinal axis between about 30 degrees to about 60 degrees with respect to a plane parallel to the longitudinal axis, about 30 degrees with respect to a plane parallel to the longitudinal axis. The lower region 150 can be curved and/or inclined towards the longitudinal axis such that the lower ends of the lower region 150 can extend in a direction generally perpendicular to the longitudinal axis.

In some embodiments, the outer frame body 142 in an expanded configuration can have a diameter at its widest portion of between about 30 mm to about 60 mm, between about 35 mm to about 55 mm, about 40 mm, any sub-range within these ranges, or any other diameter as desired. In some embodiments, the outer frame body 142 in an expanded configuration can have a diameter at its narrowest portion between about 20 mm to about 40 mm, any sub-range within these ranges, or any other diameter as desired. In some embodiments, the outer frame body 142 in an expanded configuration can have a diameter at a lower end of the lower region 150 between about 20 mm to about 40 mm, any sub-range within these ranges, or any other diameter as desired. In some embodiments, in an expanded configuration, the ratio of the diameter of the outer frame body 142 at its widest portion to the diameter of the frame body 142 at its narrowest portion can be about 3:1, about 5:2, about 2:1, about 3:2, about 4:3, any ratio within these ratios, or any other ratio as desired.

The outer frame body 142 can have an axially compact configuration relative to the radial dimension. The outer frame body 142 in an expanded configuration can have an the axial dimension between the upper and lower ends of the outer frame body 142 (i.e., the "height" of the outer frame body 142) of between about 10 mm to about 40 mm, between about 18 mm to about 30 mm, about 20 mm, any sub-range within these ranges, or any other height as desired. In some embodiments, the ratio of the diameter of the largest portion of the outer frame body 142 to the height of the outer frame body 142 when the frame is in its expanded configuration can be about 3:1, about 5:2, about 2:1, about 3:2, about 4:3, about 13:10, about 5:4, or about 1:1. Thus, in some embodiments the width at the largest portion of the outer frame body 142 can be greater than the height of the outer frame body 142.

With continued reference to the outer frame 140 illustrated in FIGS. 6A-6D, the outer frame body 142 can include a plurality of struts with at least some of the struts forming cells 154. Any number of configurations of struts can be used, such as rings of undulating struts shown forming ellipses, ovals, rounded polygons, and teardrops, but also chevrons, diamonds, curves, and various other shapes.

The cells 154 can have an irregular octagonal shape such as a "teardrop" shape. The cells 154 can be formed via a combination of struts. As shown in the illustrated embodiment, the upper portion of cells 154 can be formed from a set of circumferentially-expansible struts 156a having a zig-zag or undulating shape forming a repeating "V" shape. The circumferentially-expansible struts 156a can be inclined or curved radially outwardly away from the longitudinal axis of the prosthesis 100 such that an upper portion of the struts 156a are positioned closer to the longitudinal axis of the prosthesis 100 than the lower portion of the struts 156a. The bottom portion of cells 154 can be formed from a set of struts 156b extending downwardly from a central or generally central location of each of the "V" shapes. The struts 156b can extend along with a plane parallel to and/or extending through the longitudinal axis of the prosthesis 100.

While the struts 156 are generally described and illustrated as being straight segments, it is to be understood that some or all of the struts 156 may not form entirely straight segments. For example, the struts 156 can include some curvature such that the upper and/or lower apices are curved.

The geometry of cells 154 can allow the cells 154 to foreshorten as the outer frame 140 is expanded. As such, one or more of cells 154 can allow the outer frame 140 to foreshorten as the outer frame 140 is expanded. Foreshortening of the outer frame 140 can be used to secure the prosthesis to intralumenal tissue in a body cavity such as tissue at or adjacent a native valve including, but not limited to, a native valve annulus and/or leaflets. For example, expansion of the outer frame 140 can allow the outer frame 140 to exert a radially outward force against the tissue at or adjacent the native valve, such as the native valve annulus and/or leaflets.

Figure 7A:
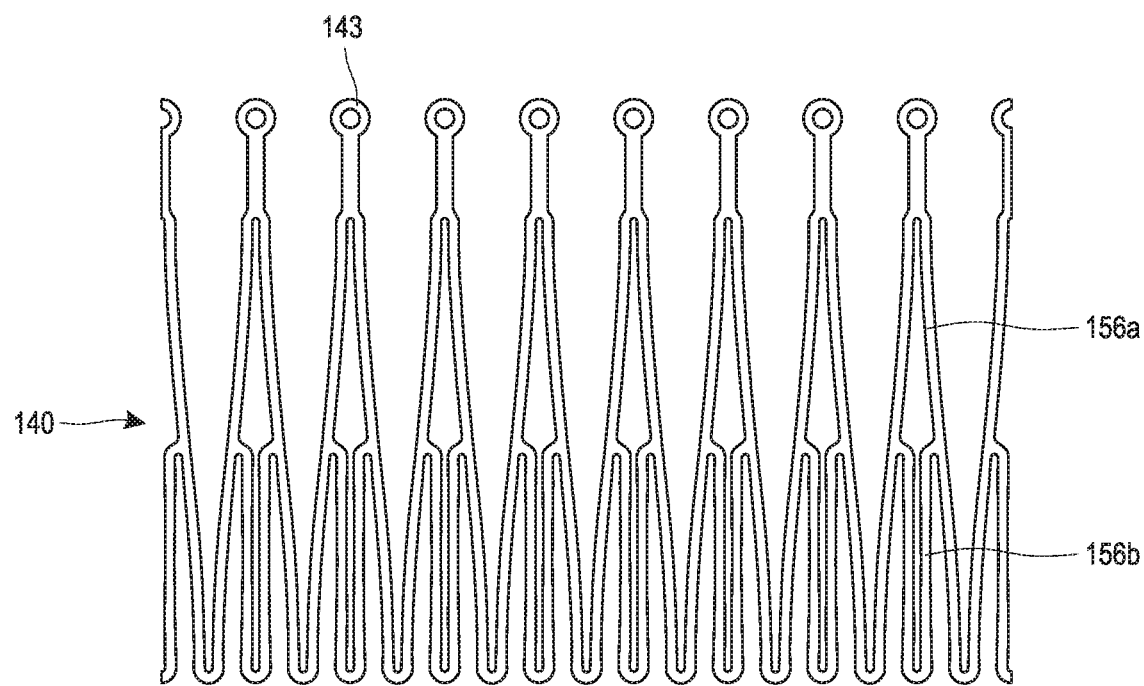
FIG. 7A illustrates a flat pattern of the outer frame of FIG. 6 in a compressed configuration.
Figure 7B:
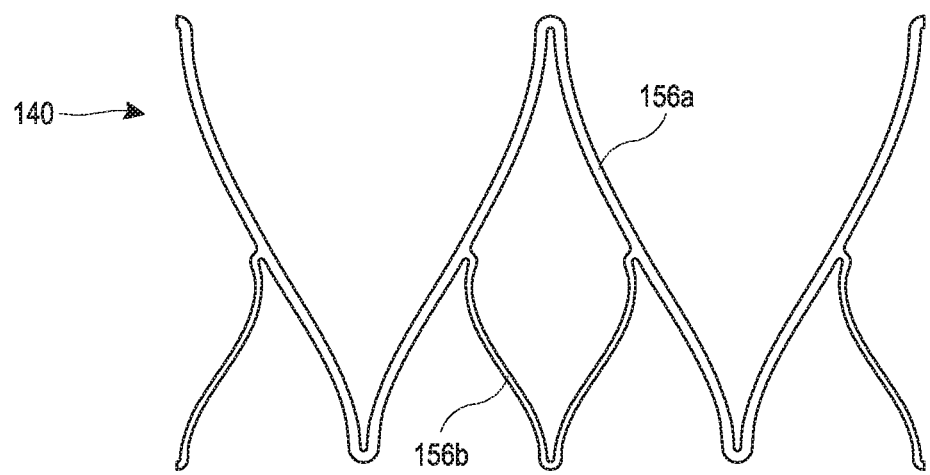
FIG. 7B illustrates a flat pattern of the outer frame of FIG. 6 in an expanded configuration.

FIGS. 7A-7B illustrate a flat pattern of the outer frame 140 in the compressed (FIG. 7A) and expanded (FIG. 7B) position. As shown, struts 156b are generally held circumferentially between struts 156a in both the compressed and expanded position. Further, in some embodiments, the struts 156a/156b can be asymmetric, thus making some struts compressible/expandably weaker than other struts. In particularly, struts 156b can have a different width/thickness than struts 156a. While symmetric cells can have uneven expansion and crimp, the asymmetric cells disclosed herein can have even expansion and crimping. Further, having the different width/thickness can promote stability of the valve. The larger struts can be what the delivery system hold onto, so these can be stronger so when the delivery system crimps the prosthesis 100, it has more leverage over the thinner struts. However, in some embodiments struts 156a/156b are the same thickness/width (e.g., are symmetric).

In some embodiments, struts 156b can be 100%, 95%, 90%, 80%, 70%, 60%, 50%, 40%, or 30% the thickness/width of struts 156a. In some embodiments, struts 156b can be less than 100%, 95%, 90%, 80%, 70%, 60%, 50%, 40%, or 30% the thickness/width of struts 156a. In some embodiments, struts 156b can be greater than 95%, 90%, 80%, 70%, 60%, 50%, 40%, or 30% the thickness/width of struts 156a.

Figure 7C:
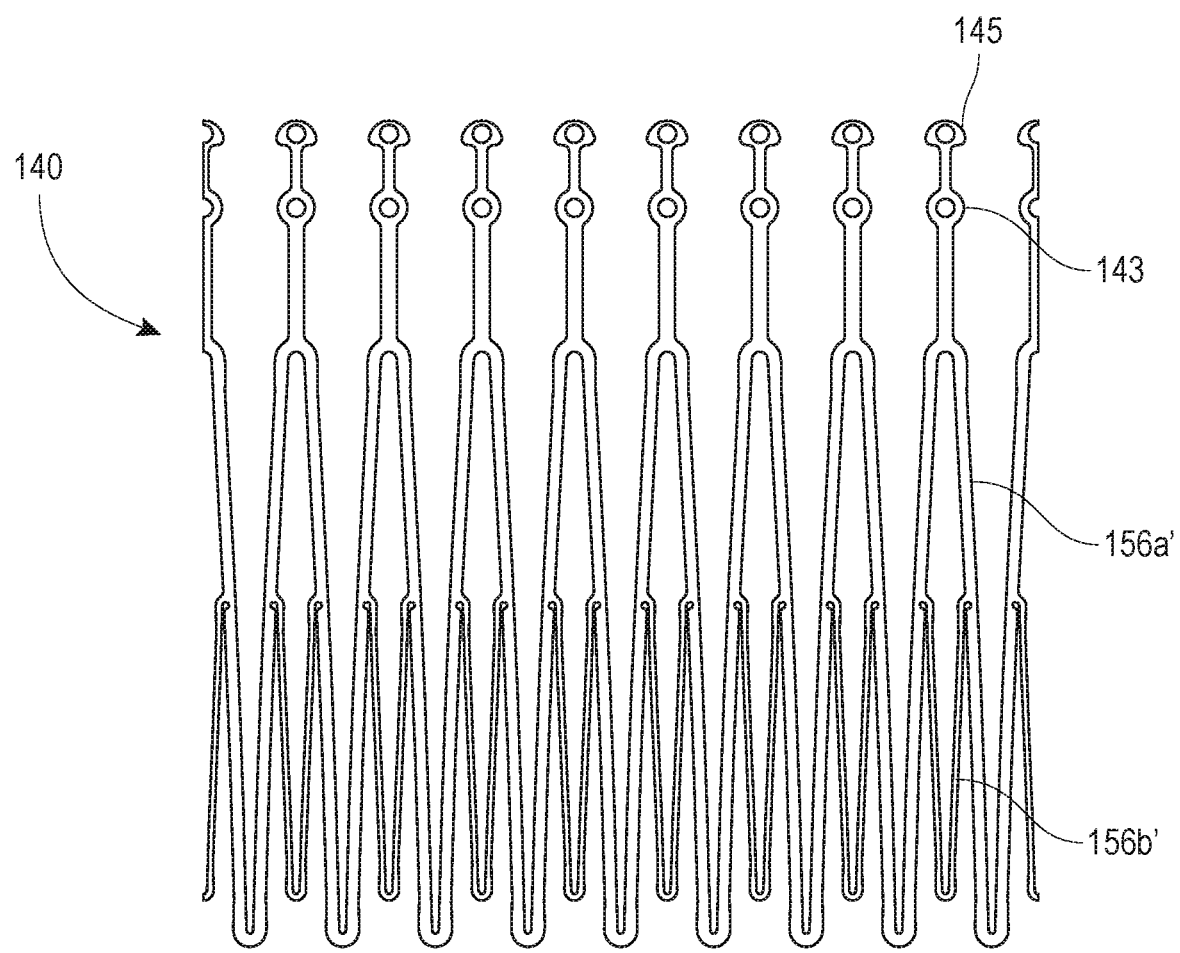
FIGS. 7C-7D illustrate alternate embodiments of a flat pattern of an outer frame.
Figure 7D:
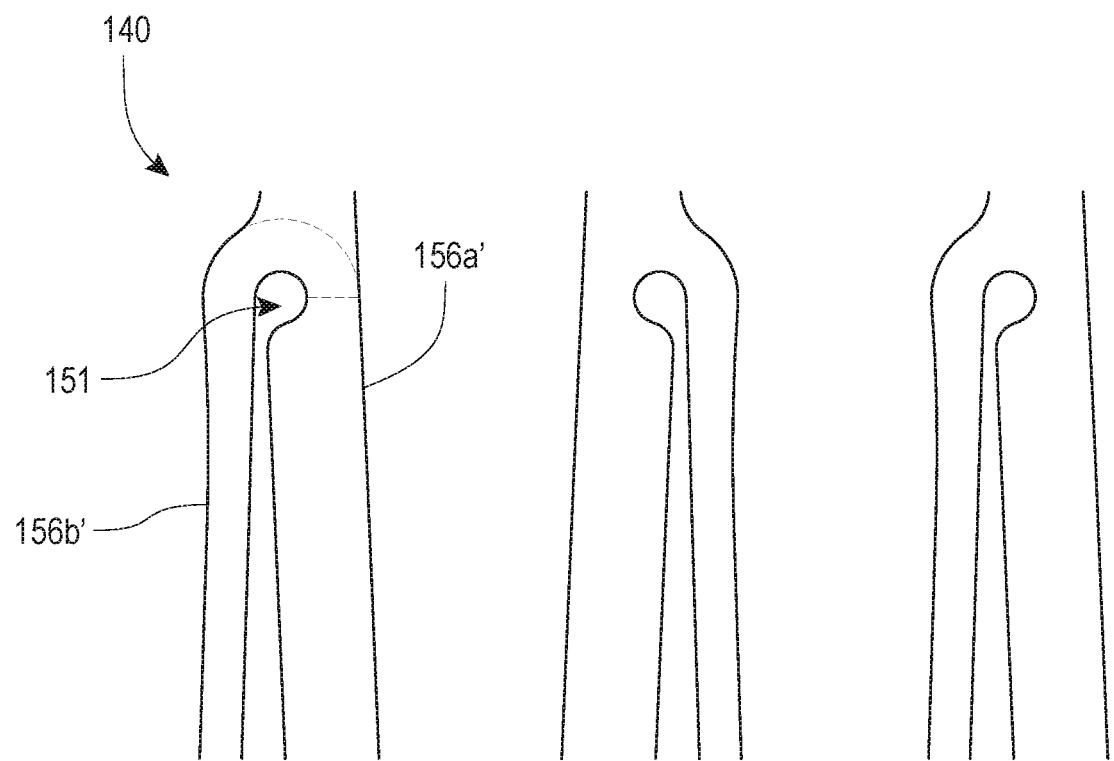

FIGS. 7C-7D illustrates another embodiment of a flat pattern of an outer frame 140, and can include any or all of the features discussed above with respect to FIGS. 7A-7B. Features disclosed with respect to FIGS. 7C-7D can be used in conjunction with, or instead of any of the outer frame features discussed herein. Advantageously, the outer frame 140 can include a notch 151 that partially extends into the strut 156a' at the connection between the struts 156a/156b'. The notch can be rounded, as shown in FIG. 7D, or may be triangular, squared, or another cut pattern and the particular shape of the notch is not limiting. The notch 151 can save approximately 0.25 mm of material per strut, allowing for a total reduction of 4.55 mm in circumference as compared to non-notched configurations. Further, as the peak force is generally at the connection of the struts 156a/156b', and the design can reduce the overall straight on the outer frame 140.

Additionally, the outer frame 140 can include a tab 145 extending proximally away from the eyelet 143, such as also shown in the following FIGS. 8A-8B. This can allow for better attachment between the outer frame and the inner frame, for example by allowing for a second aperture per strut and more area for sutures to attach, and can provide for an alternative attachment mechanism. Thus, the tab 145 can be, for example, a mushroom tab as disclosed herein with respect to the inner frame 120, and may allow for attachment into the delivery system.

Figure 8A:
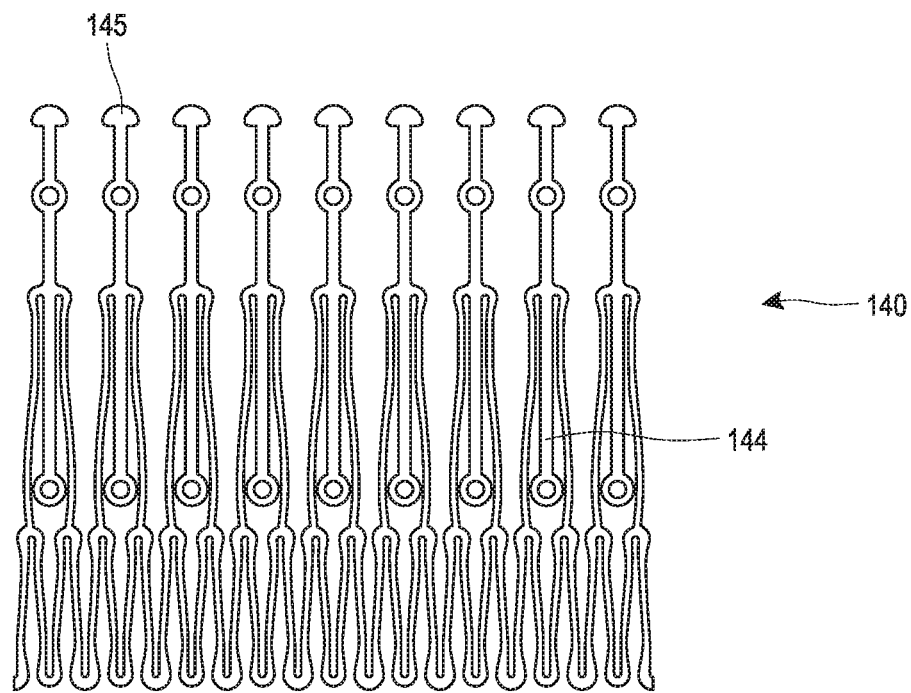
FIGS. 8A-8B illustrate alternative flat patterns for an outer frame.
Figure 8B:
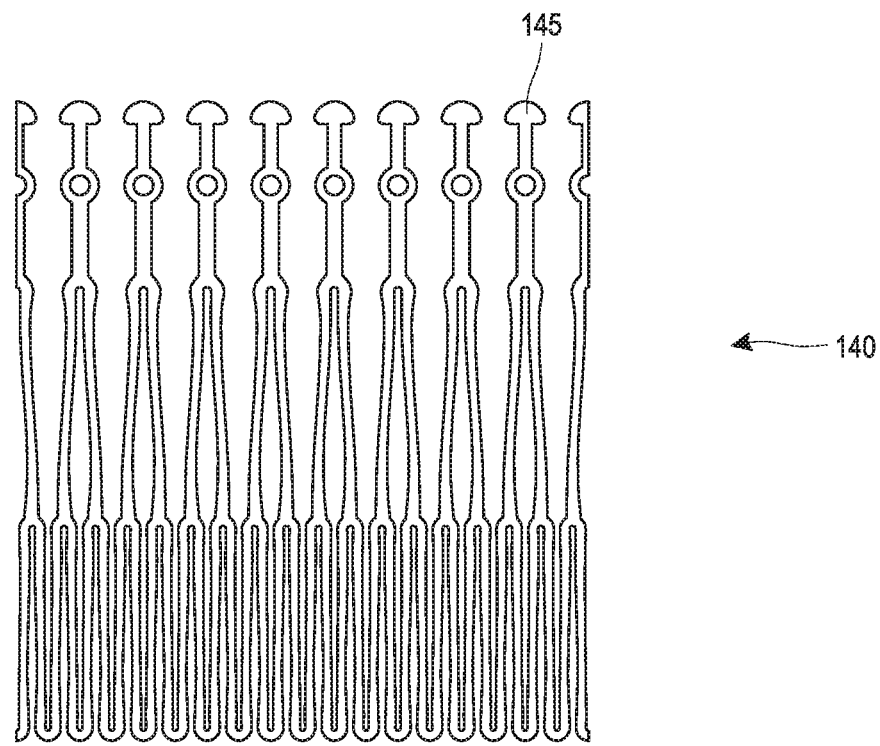

FIGS. 8A-8B illustrate flat patterns of alternative configurations of the outer frame 140, and can include any or all of the features disclosed above with respect to FIGS. 7A-7D. Notably, FIG. 8A illustrates an outer frame 140 having outer frame anchoring feature 144, an expanded version of which is shown in FIG. 12. In addition, both FIGS. 8A and 8B include tabs 145 extending upwards.

In embodiments including the outer frame anchoring feature 144, such as shown in FIG. 12, the outer frame anchoring feature 144 can extend outwardly relative to the longitudinal axis 102 of the prosthesis 100. The outer frame anchoring feature 144 can extend at or proximate the juncture between the upper region 146 and the intermediate region 148 of the outer frame body 142. The outer frame anchoring feature 144 can extend in a direction that is more perpendicular to the longitudinal axis 102 than parallel and/or can extend in a downward direction from the longitudinally-extending section 146a. The outer frame anchoring feature 144 can extend in a direction generally aligned with the outwardly-extending section 146b of the upper region 146. However, it is to be understood that the outer frame anchoring feature 144 can extend generally perpendicularly to the longitudinal axis 102 and/or in an upward direction.

In some embodiments, the outer frame anchoring feature 144 can extend in a direction that is more perpendicular to the longitudinal axis of the prosthesis 100 than parallel. As shown, the outer frame anchoring feature 144 can extend in a downward direction generally parallel to the outwardly-extending section 146b. In some embodiments, the outer frame anchoring feature 144 can extend generally perpendicularly to the longitudinal axis 102 and/or in an upward direction.

As shown in the illustrated embodiment, the outer frame 140 can include tabs 118 extending from a portion of the outer frame 140 such as an upper end of the outer frame 140. The tabs 118 can include an eyelet 143. The tab 118 can be advantageously used to couple the outer frame 140 to an inner frame 120 of the prosthesis. For example, a suture can be passed through the eyelet 143 for coupling to an inner frame 120. In some embodiments, the tabs 118 can be used to couple to other components of a prosthesis in which the outer frame 140 is used such as, but not limited to, a valve body and/or a skirt.

In some embodiments, the tab 118 can be advantageously used to couple the outer frame 140 with multiple types of delivery systems. For example, the shape of the tab 118 can be used to secure the outer frame 140 to a "slot" based delivery system. The eyelets 120 can be used to secure the outer frame 140 to a "tether" based delivery system such as those which utilize sutures, wires, or fingers to control delivery of the outer frame 140 and the prosthesis. This can advantageously facilitate recapture and repositioning of the outer frame 140 and the prosthesis in situ. In some embodiments, the outer frame 140 and prosthesis can be used with the delivery systems described herein, including but not limited to, those described in U.S. Pat. Nos. 8,414,644 and 8,652,203 and U.S. Publication Nos. 2015/0238315, the entireties of each of which are incorporated by reference herein. In some embodiments, a tab can be positioned at an end of a strut similar to locking tabs 232.

While the below discusses anchoring features 124, 144, it will be understood that the prosthesis 100 may not include feature 144. One or both anchoring features 124, 144 (if used) can contact or engage a native valve annulus, such as the native mitral valve annulus, tissue beyond the native valve annulus, native leaflets, and/or other tissue at or around the implantation location during one or more phases of the cardiac cycle, such as systole and/or diastole. In some embodiments, one or both anchoring features 124, 144 (if used) do not contact or engage, or only partially contact or engage, a native valve annulus, such as the native mitral valve annulus, tissue beyond the native valve annulus, native leaflets, and/or other tissue at or around the implantation location during one or more phases of the cardiac cycle, such as systole and/or diastole. However, it is to be understood that in some embodiments, when the prosthesis 100 is used for a replacement mitral valve prosthesis, during diastole and/or systole, both the inner frame anchoring feature 124 and the outer frame anchoring feature 144 (if used) can be sized to contact or engage the native mitral valve annulus.

The anchoring features 124, 144 (if used) and anchor tips 124a, 144a (if used) are preferably located along the prosthesis 100 with at least part of the foreshortening portion positioned between the anchoring features 124, 144 (if used) so that a portion of the anchoring features 124, 144 (if used) will move closer together with expansion of the prosthesis 100. This can allow the anchoring features 124, 144 (if used)

to close in on opposite sides of the native mitral annulus to thereby secure the prosthesis at the mitral valve. In some embodiments, the anchoring features 124, 144 (if used) can be positioned such that the anchoring features 124, 144 (if used) do not contact opposing portions of the native mitral annulus at the same time. For example, when the prosthesis 100 is used for a replacement mitral valve prosthesis, during at least systole, in some embodiments the inner frame anchoring feature 124 is sized to contact or engage the native mitral valve annulus whereas the outer frame anchoring feature 144 (if used) is sized to be spaced from the native mitral valve annulus. This can be beneficial when outer frame anchoring feature 144 (if used) is used to provide stabilization and help align the prosthesis. In some embodiments, the anchoring features 124, 144 (if used) can be positioned such that the anchoring features 124, 144 (if used) grasp opposite side of the native mitral annulus.

While the anchoring features 124, 144 (if used) have been illustrated as extending from the lower end of the lower region 130 of the inner frame body 122 and at a junction between the upper region 146 and the intermediate region 148 of the outer frame body 142 respectively, it is to be understood that the anchoring features 124, 144 (if used) can be positioned along any other portion of the prosthesis 100 as desired. Moreover, while two anchoring features 124, 144 (if used) have been included in the illustrated embodiment, it is to be understood that a greater number or lesser number of sets of anchoring features can be utilized.

Components of the outer frame 140, such as the outer frame body 142 can be used to attach or secure the prosthesis 100 to a native valve, such as a native mitral valve. For example, the intermediate region 148 of the outer frame body 142 and/or the outer anchoring feature 144 can be positioned to contact or engage a native valve annulus, tissue beyond the native valve annulus, native leaflets, and/or other tissue at or around the implantation location during one or more phases of the cardiac cycle, such as systole and/or diastole. In situations where the outer frame body 142 is positioned within a native mitral valve, the outer frame body 142 can beneficially eliminate, inhibit, or limit downwardly directed forces such as those which are applied on the prosthesis 100 during diastole and/or upwardly directed forces such as those which are applied on the prosthesis 100 during systole. As another example, the outer frame body 142 can be sized and positioned relative to the inner frame anchoring feature 124 such that tissue of the body cavity positioned between the outer frame body 142 and the inner frame anchoring feature 124, such as native valve leaflets and/or a native valve annulus, can be engaged or pinched to further secure the prosthesis 100 to the tissue. For example, the lower region 150 of the outer frame body 142 can be positioned at or proximate a tip or end of the inner frame anchoring feature 124. As shown, the lower region 150 of the outer frame body 142 is positioned such that at least a portion is positioned radially inward of and below the inner frame anchoring feature 124. In some embodiments, a portion of the outer frame 140, such as the lower region 150, can be attached to the inner frame body 122 via one or more tethers or sutures to limit the outward extension of the outer frame 140 relative to the inner frame body 122. This can beneficially maintain a portion of the outer frame 140 between the inner frame body 122 and the inner frame anchoring feature 124. Although the inner frame anchoring feature 124 is shown extending from the inner frame body 122, it is to be understood that such an anchoring feature can extend from the outer frame body 140.

Use of an inner frame 120 and an outer frame 140 can be beneficial for the design of the prosthesis in that the inner frame 120 can be designed to suit the structure of the valve body 160 and the outer frame 140 can be designed to suit the anatomy of the body cavity in which the prosthesis 100 is to be used. For example, the valve body 160 (shown in FIG. 10) can be cylindrical and have a smaller diameter than the body cavity. In such an embodiment, the inner frame 120 can advantageously have a smaller shape and/or size to support the valve body 160 while the outer frame 140 can have a larger shape and/or size to secure the prosthesis 100 to the body cavity. Moreover, in embodiments in which the outer frame 140 is larger than the inner frame 120, the shape of the outer frame 140 can beneficially enhance hemodynamic performance. For example, the shape of the outer frame 140 with a larger, generally cylindrical intermediate region 148 can allow for significant washout on an underside of the valve body 160. This washout can beneficially reduce the risk of thrombosis or clot formation under and around the valve body 160.

The outer frame 140 can be formed from many different materials including, but not limited to, a shape-memory metal such as Nitinol. The outer frame 140 can be formed from a plurality of struts forming open cells. In some embodiments, the outer frame 140 can have a more flexible construction as compared to other components of the prosthesis 100 such as, but not limited to, the inner frame 120. This can be achieved, for example, by the dimensions of the struts and by the configuration of the struts. For example, fewer struts, thinner struts, and/or a different material for the struts can be used. The more flexible construction can allow the outer frame 140 to better conform to the anatomy of the body cavity, such a native valve annulus and/or native leaflets. This can be beneficial for anchoring against the body cavity and/or forming a seal against the body cavity. However, it is to be understood that in some embodiments the outer frame 140 can have a construction which is about as rigid as, or more rigid than, other components of the prosthesis 100, such as the inner frame 120.

The outer frame 140, and any other frame described herein, may include features and concepts similar to those disclosed in U.S. Pat. Nos. 8,403,983, 8,414,644, and 8,652,203, U.S. Publication Nos. 2011/0313515, 2014/0277390, 2014/0277427, 2014/0277422, 2018/0021129, 2018/0055629, and 2015/0328000, the entireties of each of which have been incorporated by reference. Moreover, although the outer frame 140 has been described as including an outer frame body 142 and an outer frame anchoring feature 144, it is to be understood that the outer frame 140 need not include all components. For example, in some embodiments, the outer frame 140 can include the outer frame body 142 while omitting the outer frame anchoring feature 144. Moreover, although the outer frame body 142 and the outer frame anchoring feature 144 have been illustrated as being unitarily or monolithically formed, it is to be understood that in some embodiments the outer frame body 142 and the outer frame anchoring feature 144 can be formed separately. In such embodiments, the separate components can be attached using any of the fasteners and techniques described herein. For example, the outer frame anchoring feature 144 can be formed separately from the outer frame body 142 and can be attached to the outer frame body 142.

Skirt

FIGS. 9-11 illustrate the prosthesis 100 with the skirt 180. The skirt 180 can be attached to the inner frame 120 and/or outer frame 140 (or any of the alternate frames disclosed herein). As shown, the skirt 180 can be positioned around and secured to a portion of, or the entirety of, the exterior of the inner frame 120 and/or outer frame 140, such as in between the two frames 120/140. The skirt 180 can also be secured to a portion of the valve body 160. The skirt 180 can follow the contours of the outer frame 140, such as the contours of the upper region 146, the intermediate region 148, and/or the lower region 150. In some embodiments, the skirt 180 can be used to attach the outer frame 140 to the inner frame 120. Although not shown, it is to be understood that the skirt 180 can be positioned around and secured to a portion of, or the entirety of, an interior of the inner frame 120 and/or the outer frame 140. Moreover, it is to be understood that while the skirt 180 can follow the contours of portions of the inner frame 120 and the outer frame 140, at least a portion of the skirt 180 can be spaced apart from at least a portion of both the inner frame 120 and the outer frame 140. In some embodiments, the skirt 180 can be spaced apart from the upper region 146 of the outer frame 140. For example, the skirt 180 can be positioned below the upper region 146. In such an embodiment, the spaced-apart portion of the skirt 180 can be loose such that the skirt 180 is movable relative to the upper region 146 or can be taut such that the skirt 180 is generally fixed in position.

The skirt 180 can be annular and can extend entirely circumferentially around the inner frame 120 and/or outer frame 140. The skirt 180 can prevent or inhibit backflow of fluids, such as blood, around the prosthesis 100. For example, with the skirt 180 positioned annularly around an exterior of the inner frame 120 and/or outer frame 140, the skirt 180 can create an axial barrier to fluid flow exterior to the inner frame 120 and/or outer frame 140 when deployed within a body cavity such as a native valve annulus. The skirt 180 can encourage tissue in-growth between the skirt 180 and the natural tissue of the body cavity. This may further help to prevent leakage of blood flow around the prosthesis 100 and can provide further securement of the prosthesis 100 to the body cavity. In some embodiments, the skirt 180 can be tautly attached to the inner frame 120 and/or outer frame 140 such that the skirt 180 is generally not movable relative to the inner frame 120 and/or outer frame 140. In some embodiments, the skirt 180 can be loosely attached to the inner frame 120 and/or outer frame 140 such that the skirt 180 is movable relative to the inner frame 120 and/or outer frame 140.

In some embodiments, the skirt 180 can be formed from a material such as knit polyester (e.g., polyethylene terephthalate (PET), polyvalerolactone (PVL)) or any other biocompatible material such as those which are wholly or substantially fluid impermeable, flexible, stretchable, deformable, and/or resilient. The skirt 180 and/or the liner may be made from the same or similar materials. As shown in the illustrated embodiment, the skirt 180 can be formed as separate components. The components can be attached together using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques.

In some embodiments, the skirt 180 can be attached to the inner frame 120, such as at one of the struts. For example, the skirt 180 can attach to longitudinally extending strut 138 or the circumferentially extending struts 136a/13b. The skirt 180 can be attached through sutures, adhesives, tying, etc. and the attachment is not limiting. In some embodiments, the skirt 180 can also be attached to the outer frame 140.

Figure 13A:
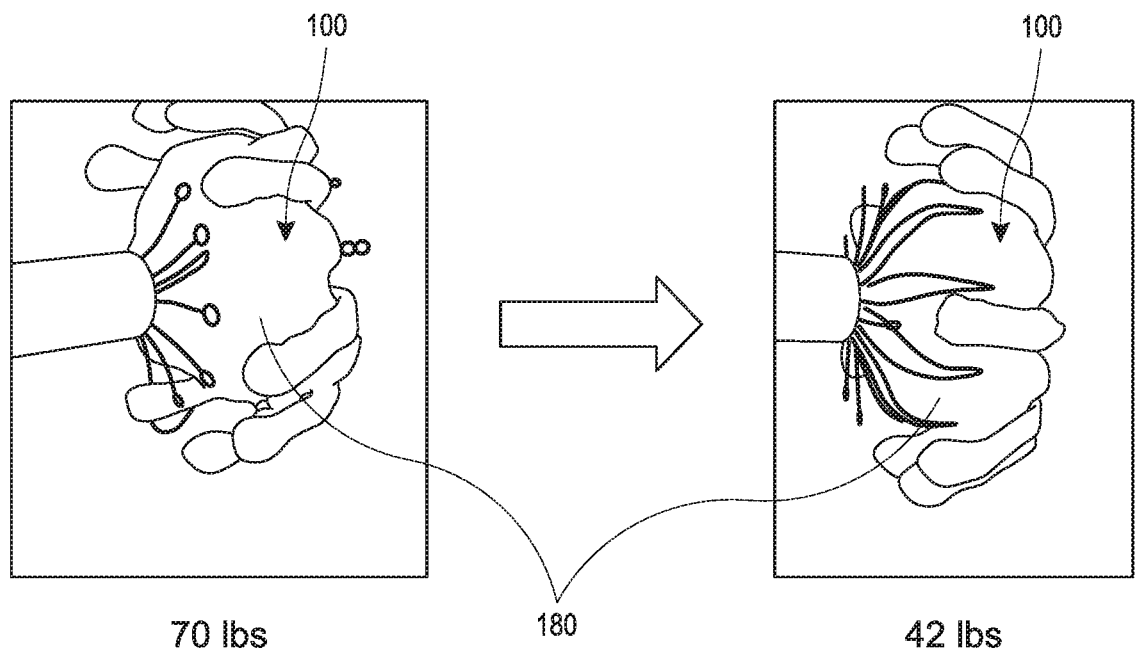
FIGS. 13A-13B illustrate auto-tucking features of embodiments of the disclosed prosthesis.
Figure 13B:
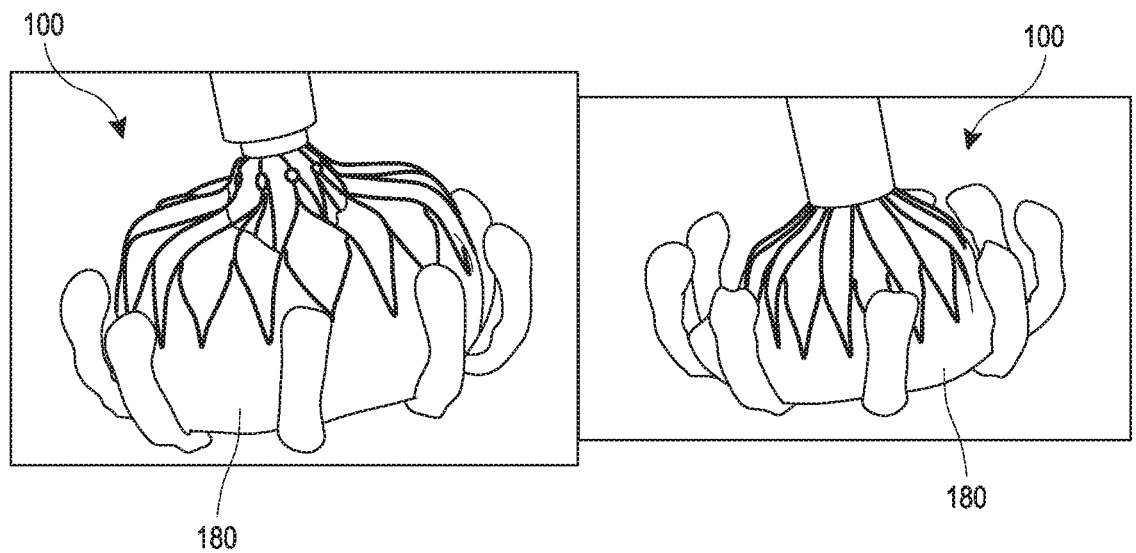

As the skirt 180 is attached to the inner frame 120, when the prosthesis 100 first begins to crimp, such as for retraction/retrieval, the skirt 180 is pulled inwardly with the inner frame 180. Thus, the skirt 180 can be tucked between the struts of the outer frame 140. It can be advantageous to perform this automatic tucking as in some embodiments a large amount of material (such as cloth) of the outer skirt 180 is needed to seal particularly large annuluses. Accordingly, the skirt 180 can bunch up/prevent low profile crimping or require large amounts of force to fully crimp the prosthesis because of the skirt 180 "clogging" the struts and preventing closure. Thus, manual tucking can be avoided and retrieval forces can be removed. FIGS. 13A-13B illustrate the automatic tucking of the cloth into the prosthesis 100.

As shown in FIG. 9, the ventricular portion (e.g., the bottom, distal, or lower portion) of the skirt 180 (e.g., fabric skirt) may act as a "curtain" around the inner frame 220. For example, the ventricular portion 182 of the outer skirt 180 is not attached to the outer frame 140 as the outer frame 140 ends above this portion of the skirt 180. This portion 182 is also not attached to the inner frame 220 until the bottom of the skirt 180. Thus, the portion 182 of the outer skirt 180 is circumferentially unattached, and is instead held generally in tension between an inner surface of the outer frame 140 and the an outer surface of the ventricular or distal end of the inner frame 220. This allows the outer skirt 180 to flex or bend when radial pressure is applied to it. Thus, the outer skirt 180 has the flexibility to conform to a valve annulus, such as the mitral valve annulus, which can create an improved seal between the prosthesis 100 and the annulus. This can be especially advantageous as by having the curtain configuration and a reduced outer frame 140, the overall profile of the device can be reduced. Further, by eliminating the lower portion of the outer frame 140 (e.g., the portion that would surround portion 182), the outer frame 140 can compress more easily against the inner frame 220 and the overall structure can compress to a much smaller diameter as compared to a device having an outer frame extending all the way to the inner frame anchoring features 124.

Figure 14A:
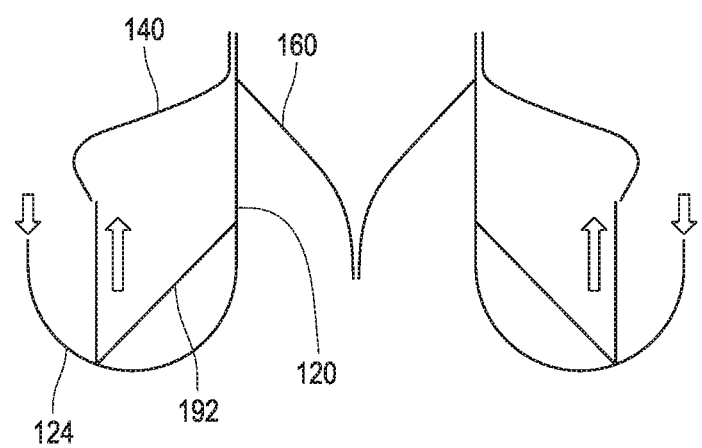
FIGS. 14A-14B illustrate an embodiment for improving inner frame anchoring feature stiffness.
Figure 14B:
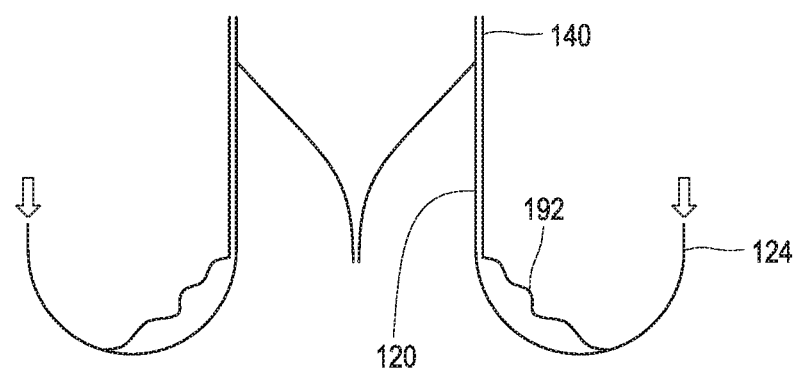
Figure 15:
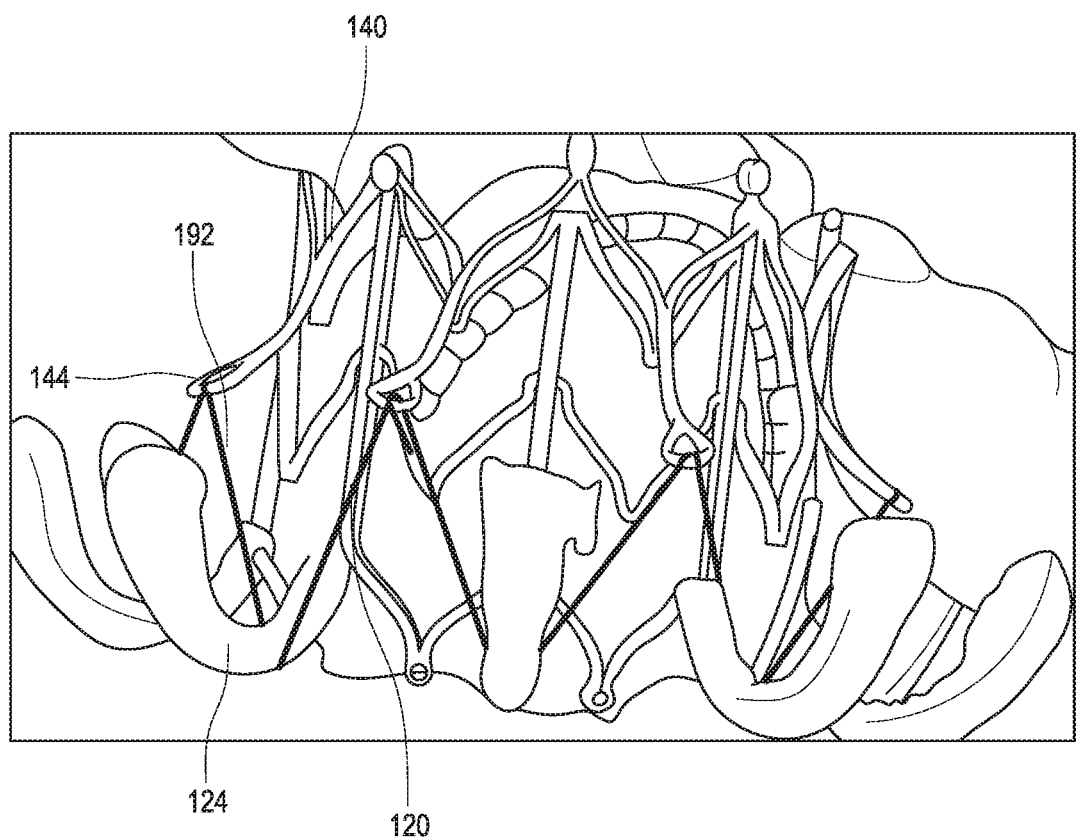
FIG. 15 illustrates an alternate embodiment for improving inner frame anchoring feature stiffness.

FIGS. 14A-B and 15 illustrate an embodiment of a prosthesis 100 which can improve the stiffness of the inner frame anchoring features 124 using the outer skirt 180. In particular, the skirt 180 can be added into the prosthesis 100 to increase the stiffness of the inner frame anchoring features 124, for example by distributing force between the inner frame 120, the outer frame 140, and the added stiffness improving material 192 (which can be a portion of skirt 180). Thus, the stiffness improving material 192 can be incorporated into, or can be the same, as the skirt 180 or can be its own separate material.

FIGS. 14A-B illustrate an example embodiment of the improved stiffness. As shown, the prosthesis can include the inner frame 120 having the inner frame anchoring features 124, the outer frame 140, and the stiffness improving material 192. In some embodiments, the stiffness improving material 192 can be cloth, fabric, or other soft material such as discussed above with respect to skirt 180. As shown, the stiffness improving material 192 can be attached at three different points on the prosthesis 100. The stiffness improving material 192 can be located between the frames 120/140 our radially outwards of both frames 120/140.

At one point, the stiffness improving material 192 can be attached to a lower end of the outer frame 140. This stiffness improving material 192 can be attached at the base apices of struts 156a or at the base apices of struts 156b. However, the stiffness improving material 192 can be attached at any particular point of the outer frame 140. In some embodiments, the stiffness improving material 192 can be attached to outer frame anchoring feature 144 if used. The attachment can be sutures, threads, chemical adhesives, mechanical fastening, and the particular attachment is not limiting.

Next, the stiffness improving material 192 can be attached on the inner frame anchoring features 124. For example, it can be attached approximately midway along the inner frame anchoring features 124, such as shown in FIGS. 14A-B. However, the stiffness improving material 192 can be attached at any point along the inner frame anchoring features 124, and the particular location is not limiting. The attachment can be generally at the midpoint of the stiffness improving material 192, but this is not limiting. The attachment can be sutures, threads, chemical adhesives, mechanical fastening, and the particular attachment is not limiting.

Further, the second end of the stiffness improving material 192 can be attached to a portion of the inner frame 120. For example, it can be attached at the longitudinally extending strut 138 or at the circumferentially extending struts 136*b*. The stiffness improving material 192 can be attached at the first and second ends generally at the same longitudinal position. At some embodiments, the stiffness improving material 192 is attached to the inner frame 120 at a different longitudinal position than where it is attached to the outer frame 140. In some embodiments, the stiffness improving material 192 is attached to the inner frame 120 at a lower longitudinal position (e.g., towards the inner frame anchoring features 124) than where it is attached to the outer frame 140. In some embodiments, the stiffness improving material 192 is attached to the inner frame 120 at a higher longitudinal position (e.g., away from the inner frame anchoring features 124) than where it is attached to the outer frame 140. The attachment can be sutures, threads, chemical adhesives, mechanical fastening, and the particular attachment is not limiting.

FIG. 14A shows the prosthesis 100 in the expanded position. As shown, the stiffness improving material 192 is pulled taught, thereby applying an upward force on the stiffness improving material 192 and thus the inner frame anchoring features 124. Once the prosthesis 100 begins compress, as shown in FIG. 14B, the stiffness improving material 192 becomes slack, thus reducing the stiffness of the inner frame anchoring features 124 and facilitating retrieval.

In some embodiments, the stiffness improving material 192 can extend along a circumference of the prosthesis 100 such as discussed above with respect to skirt 180. In some embodiments, the stiffness improving material 192 can extend partially around the circumference of the prosthesis 100. In some embodiments, multiple the stiffness improving material 192 can be used. In some embodiments, the stiffness improving material 192 is attached to every inner frame anchoring features 124. In some embodiments, the stiffness improving material 192 is attached to every other inner frame anchoring features 124. In some embodiments, the stiffness improving material 192 is attached to every third inner frame anchoring features 124.

Further, the use of the stiffness improving material 192 can create a "sealed void", "clot pocket", "cloth pocket", or "pocket" between the inner frame 120 and the outer frame 140. The pocket is an empty volume covered with the stiffness improving material 192 between the inner frame 120 and the outer frame 140. This can reduce thrombosis formation on the prosthesis 100 as in an open configuration blood can flow through struts in the frames and circulate between the frames causing thrombus. In some embodiments, there can be a number of holes in the stiffness improving material 192, and thus the stiffness improving material 192 can inflate, clot over, and permanently stay inflated.

FIG. 15 illustrates an alternate stiffness improving material 192 where the stiffness improving material 192 is one or more sutures. As shown, a single suture can extend around the circumference of the prosthesis 100, but in some embodiments multiple discrete sutures can be used. In this embodiment, the sutures extend between outer frame anchoring features 144 and circumferentially adjacent inner frame anchoring feature 124, thus forming a "zig-zag" pattern around the prosthesis 100. As shown, the stiffness improving material 192 can pass through apertures at the ends of the outer frame anchoring features 144. The stiffness improving material 192 can either be tied in or pass through the apertures. The stiffness improving material 192 can then attach to material around the inner frame anchoring feature 124. In some embodiments, the stiffness improving material 192 can wrap around the inner frame anchoring features 124 themselves, such as forming a loop in the suture or extending through an aperture or around a protrusion in the inner frame anchoring feature 124. However, in some embodiments outer frame anchoring features 144 may not be used and the sutures can attach directly to the outer frame 140 such as discussed above.

Advantageously, the use of the stiffness improving material 192 of any of the above embodiments can prevent the outer frame 140 from crimping inside the inner frame 120. This can be done by providing sufficient tension with the stiffness improving material 192 to prevent insertion of lower portions of the outer frame 140 from entering the inner frame 120.

Although the prosthesis 100 has been described as including an inner frame 120, an outer frame 140, a valve body 160, and a skirt 180, it is to be understood that the prosthesis 100 need not include all components. For example, in some embodiments, the prosthesis 100 can include the inner frame 120, the outer frame 140, and the valve body 160 while omitting the skirt 180. Moreover, although the components of the prosthesis 100 have been described and illustrated as separate components, it is to be understood that one or more components of the prosthesis 100 can be integrally or monolithically formed. For example, in some embodiments, the inner frame 120 and the outer frame 140 can be integrally or monolithically formed as a single component.

Additionally, the prosthesis 100 may only include a single frame. For example, just the inner frame 120, just the outer frame 140, or a combination of the two in a single frame. Thus, the concepts discussed above, such as the hourglass shape, the strut/cell shape, etc. can be incorporated into a single frame prosthesis.

Moreover, the prosthesis 100 may be applicable to a prosthesis having more than just the inner frame 120 and the outer frame 140. Thus, the concepts discussed above, such as the hourglass shape, the strut/cell shape, etc. can be incorporated into a prosthesis having 1, 2, 3, 4, 5, or 6 frames.

Figure 16:
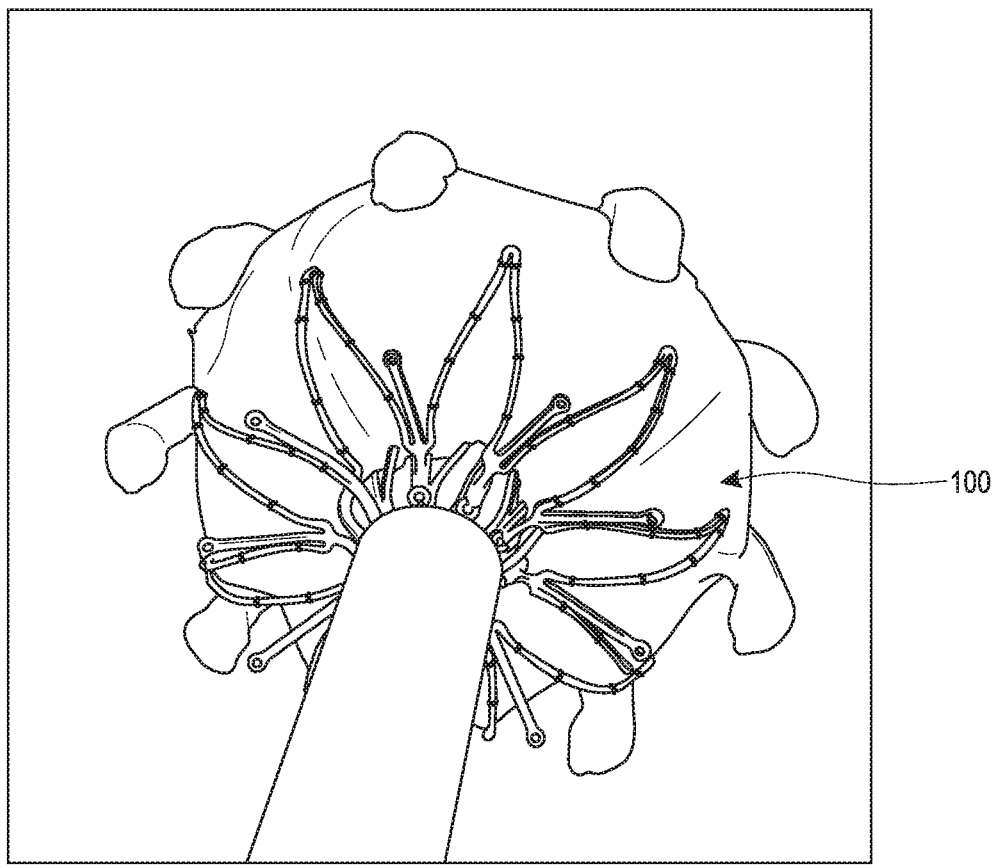
FIG. 16 illustrates assessment of prosthesis function prior to release.

FIG. 16 illustrates an embodiment of the prosthesis 100 being radially compressed.

Figure 17A:
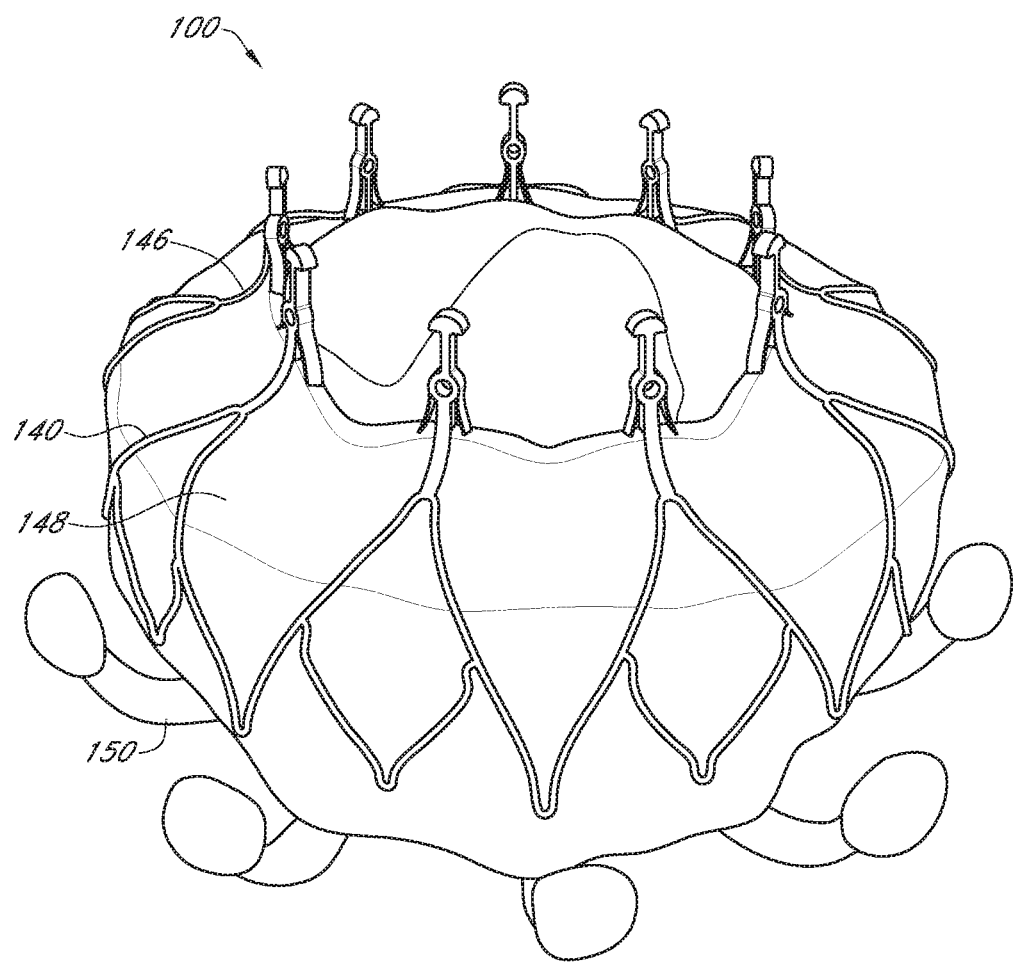
FIGS. 17A-17B illustrate an embodiment of replacement prosthesis.
Figure 17B:
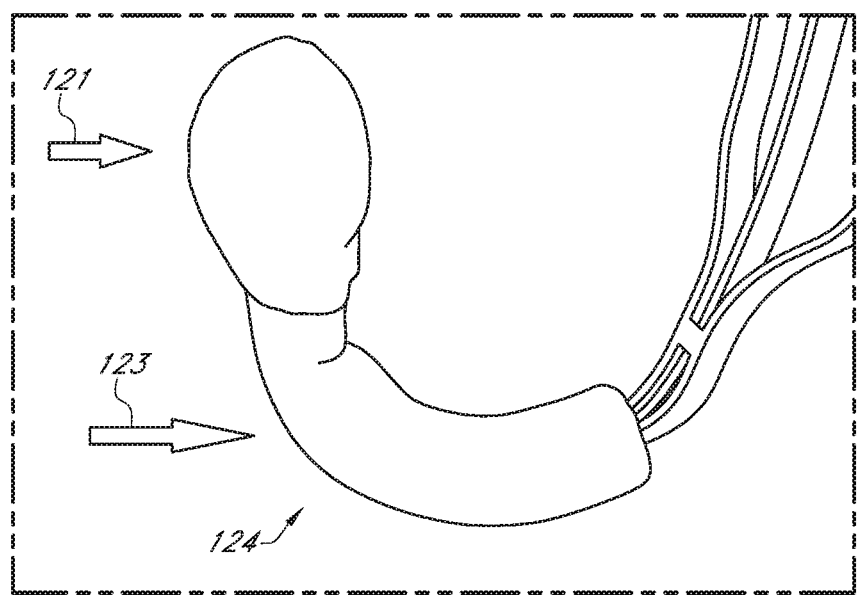

FIGS. 17A-17B illustrate embodiments of the prosthesis 100 with some modifications which can be used in conjunction with any of the implementations disclosed herein. As shown in the figures, the outer frame 140 can have a substantial angular change (e.g., bend or shoulder) between the upper region 146 and the intermediate region 148 and the lower region 150. In some embodiments, the bend could be 50, 60, 70, 80, 90, or 100 degrees. In some embodiments, the bend could be greater than 50, 60, 70, 80, 90, or 100 degrees. In some embodiments, the bend could be less than 50, 60, 70, 80, 90, or 100 degrees. In some embodiments, the lower region 150 may have approximately the same radial diameter than the intermediate region 148. In some embodiments, the lower region 150 may have smaller radial diameter than the intermediate region 148. This can, for example, allow the frame to act as a "plug" or "cork" within the mitral valve annulus. In some embodiments, the mitral valve annulus, or other structural heart features, may apply radially inward pressure on the prosthesis 100, causing some indents, bends, or compression of the intermediate region 148 or the lower region 150, which can allow the prosthesis 100 to achieve a tighter fit. The prosthesis 100 can have a scalloped inflow. This can help reduce atrial projection and promote flow prior to release from the delivery system. FIG. 17B illustrates an embodiment of an inner frame anchoring feature 124. As shown, the distal tip can be covered by a first material 121, such as ePTFE or other plastic, while the main curve can be covered by a second material 123. The second material 123 can be a foam or fabric. In some embodiments, the second material 123 can be a PET-covered polyurethane foam, though this is not limiting. The two materials can be attached together, such as by suturing, shrinkage, friction, or mechanical fastening, or can be separate.

Figure 29:
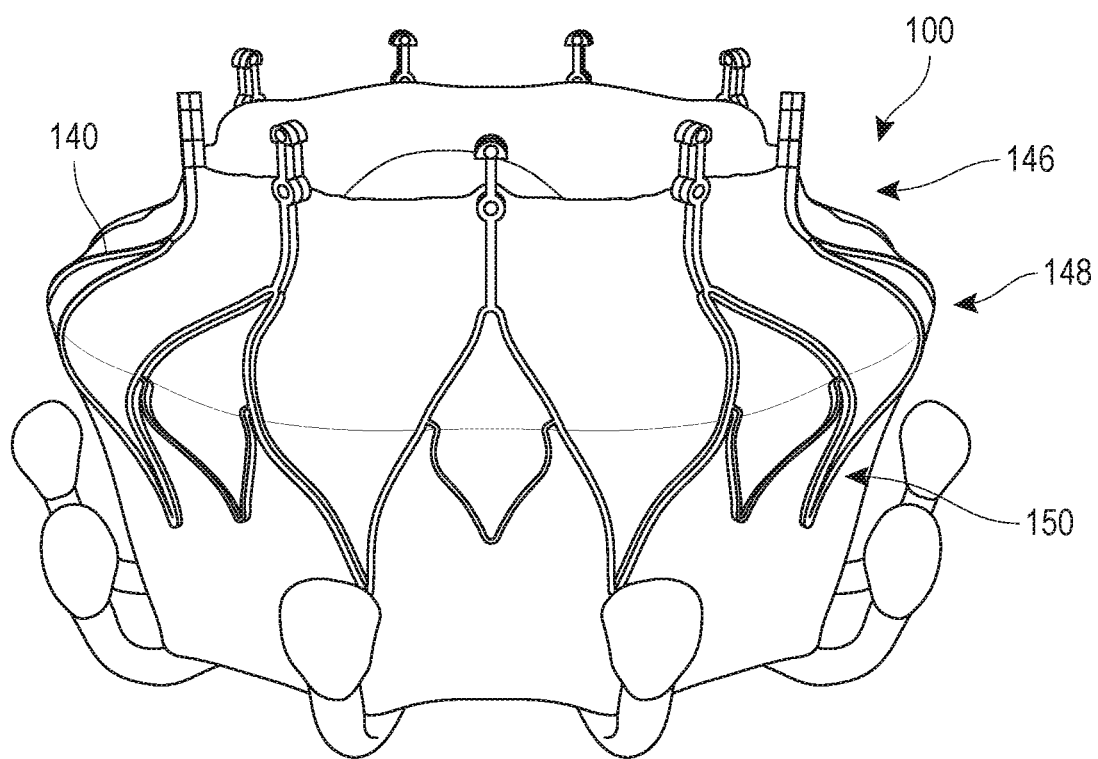
FIG. 29 is an embodiment of an alternative replacement prosthesis.
Figure 30A:
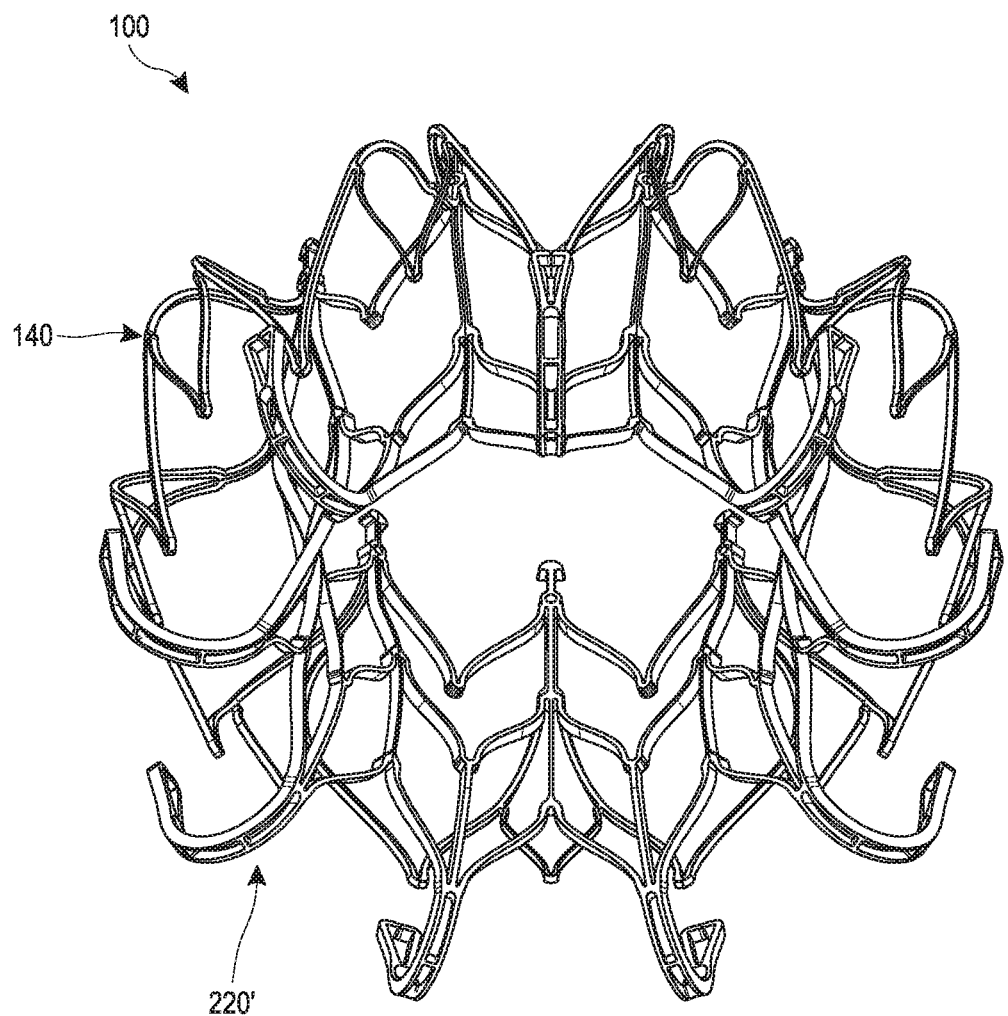
FIGS. 30A-30D illustrates an embodiment of a multi-portion replacement prosthesis.
Figure 30B:
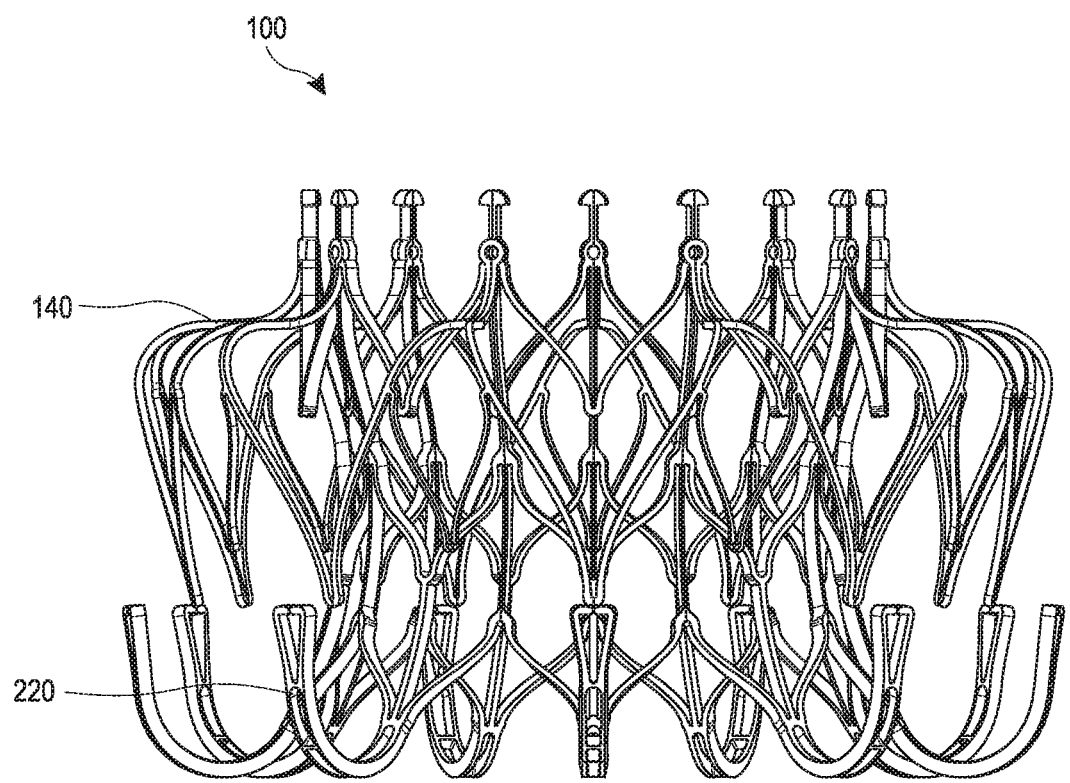
Figure 30C:
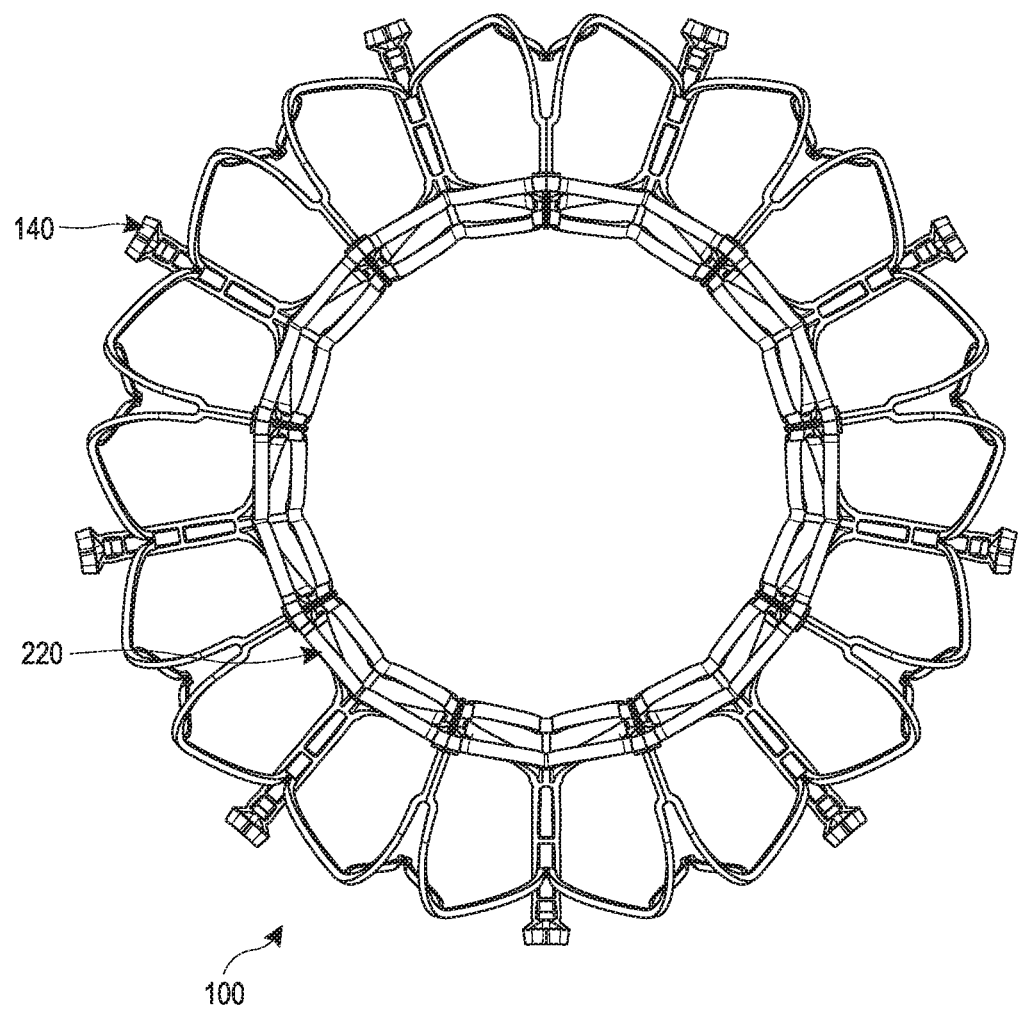
Figure 30D:
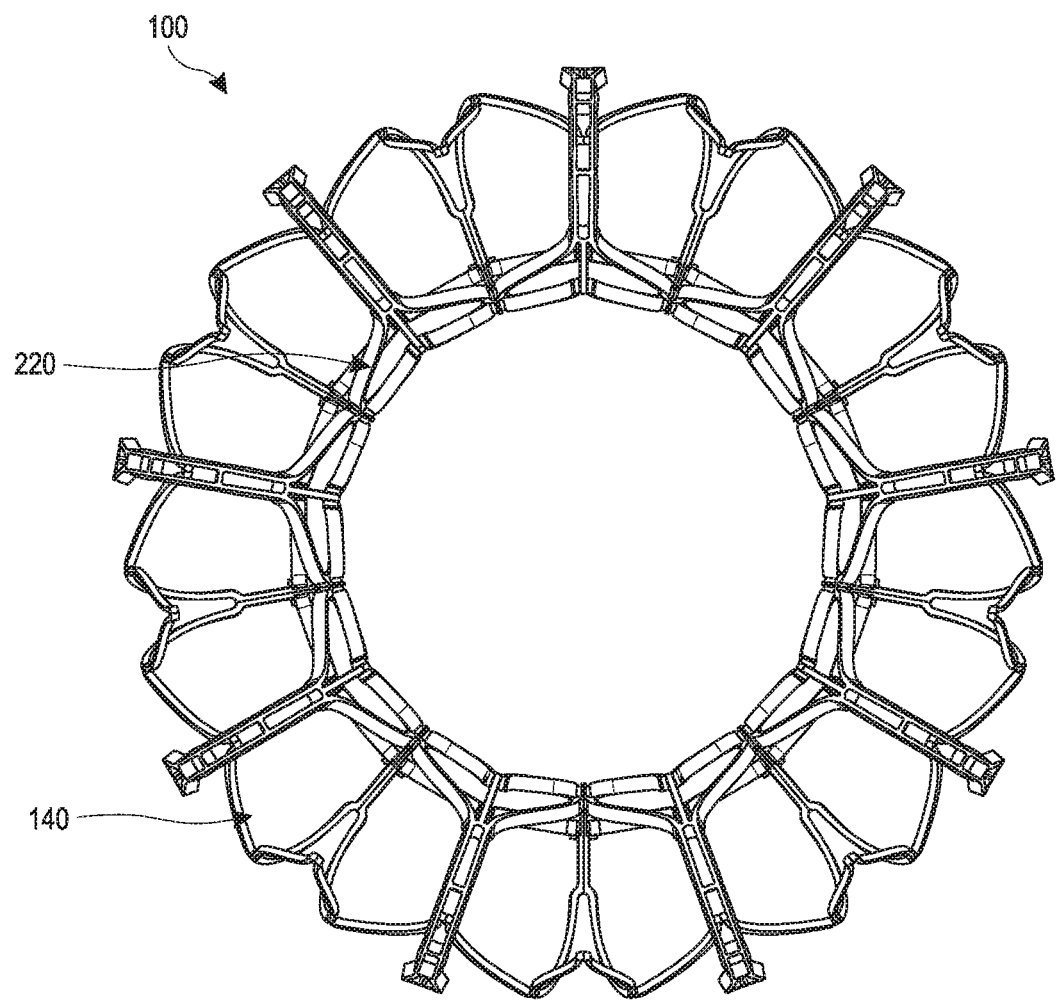

FIG. 29 illustrates an alternate embodiment of a prosthesis 100 which can include any or all of the features described herein. As shown, the outer frame 140 can have a bulbous (or generally bulbous shape). For example, the outer frame 140 can have a shoulder as shown in FIG. 29.

The different iterations of the prosthesis frame disclosed above, such as, but not limited to, the ones shown in FIG. 1, FIG. 9, FIG. 12, FIG. 17A, FIG. 21, FIG. 29, and FIG. 30A, can provide advantageous for the implantation procedure. For example, as discussed below, the prosthesis 100 expands from a compressed configuration to an expanded configuration during delivery. This can be done in or around the mitral annulus. When the outer frame 140, including any of the variations of the outer frame 140 discussed above, is expanded, it can circumferentially press against tissue on the circumference of the mitral annulus. This shape can provide a form of retention to stop the prosthesis 100 from going into the left ventricle in diastole, and generally stabilize the prosthesis 100 in the mitral valve annulus. Thus, in some implementations the prosthesis 100 outer frame 140 may not fully expand, and may be minimally to partially compressed within the mitral annulus. In other implementations, the prosthesis 100 may fully expand, and be retained within the left ventricle by the inner frame anchoring features and in the left atrium by the bulbous shape, for example including the shoulders, of the outer frame 140. In some implementations, after release of the prosthesis 100, it can be moved towards the left ventricle by the heart where it will then "cork" in the mitral annulus.

Valve Body

With reference next to the valve body 160 illustrated in FIG. 10, the valve body 160 can be positioned within the inner frame 120. The valve body 160 can be a replacement heart valve which includes a plurality of valve leaflets 262. The valve leaflets 262 can include a first edge, second edge, and tabs for attaching the valve leaflets 262 together at commissures of the valve body 160. The tabs can be used to secure the valve leaflets 262 to the inner frame 120. The first edge can be an arcuate edge and can be generally fixed in position relative to the frame 120. The second edge can be a freely moving edge which can allow the valve body 160 to open and close.

The plurality of valve leaflets 262 can function in a manner similar to the native mitral valve, or to any other valves in the vascular system as desired. The plurality of valve leaflets 262 can open in a first position and then engage one another to close the valve in a second position. The plurality of valve leaflets 262 can be made to function as a one way valve such that flow in one direction opens the valve and flow in a second direction opposite the first direction closes the valve. For example, the valve body 160 can open allow to blood to flow through the valve body 160 in a direction from an upper end to a lower end. The valve body 160 can close to inhibit blood flow through the valve body 160 in a direction from the lower end to the upper end. In situations where the prosthesis 100 is oriented such that an upper end is a proximal end and a lower end is a distal end, the valve body 160 can be positioned such that the valve body 160 can open to allow blood to flow through the valve body 160 in a proximal-to-distal direction and close to inhibit blood flow in a distal-to-proximal direction. The valve body 160 can be constructed so as to open naturally with the beating of the heart. For example, the valve body 160 can open during diastole and close during systole. The valve body 160 can replace a damaged or diseased native heart valve such as a diseased native mitral valve.

The valve body 160 can include a liner. The liner can be used to assist with fluid flow through and/or around the prosthesis 100, such as through and around the inner frame 120 and the valve leaflets 262. The liner can surround at least a portion of the valve leaflets 262 and be connected to one or more of the valve leaflets 262. For example, the one or more valve leaflets 262 can be attached to the liner along the first edge of the valve leaflets 262.

The liner can be positioned within the interior of the inner frame 120 and can form an inner wall of the prosthesis 100. For example, the liner can be positioned such that the liner is radially inward, relative to the longitudinal axis of the prosthesis 100, from the struts 136a-c of the inner frame 120. In this manner, the fluid pathway towards the valve leaflets 262 can be relatively smooth. It is also contemplated that the liner can at least be partially positioned along an exterior of the inner frame 120 and/or outer frame 140 such that at least a portion of the liner is radially outward, relative to the longitudinal axis of the prosthesis 100, from struts of the inner frame 120 and/or outer frame 140. The liner can be positioned along an upper or inlet side of the inner frame 120. The liner can extend from the first edge of the valve leaflets 262 towards the upper end of the inner frame 120. The liner can also extend below the first edge of the valve leaflet 262 towards the lower end of the inner frame 120. The liner can also be made to move with foreshortening portions of the inner frame 120.

In some embodiments, the liner can extend the entire length of the inner frame 120 or the inner frame body 122. In other embodiments, it can extend along only part of the length of the inner frame body 122 as shown. In some embodiments, the ends of the valve leaflets 262 can coincide with ends of the liner. In addition, one or more of the ends of the inner frame body 122 can coincide with the ends of the liner. An end of the liner can be positioned between the upper end of the inner frame 120 and the valve leaflets 262. The end of the liner can extend above an upper end of the inner frame body 122 and extend along a portion of the locking tabs. In some embodiments, the end of the liner can be positioned at or proximate an uppermost portion of the first or arcuate edge of the valve leaflet 262 below the upper end of the inner frame body 122.

Other shapes and configurations can also be used for the valve body 160. In some embodiments, the liner may extend along the length of the leaflets, but is not connected to them. In the illustrated embodiment, the liner is attached to the inner frame 120 and at least a portion of the leaflets 262, such as the first or arcuate edge, is attached to the liner. Portions of the valve leaflets 262, such as the portions of the first edge and/or tabs, can also be attached to the inner frame 120. The liner and/or the valve leaflets 262 can be attached to the inner frame 120 or to each other using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques.

The liner can be constructed in multiple different ways. The liner can be made a layer of resilient material, such as such as knit polyester (e.g., polyethylene terephthalate (PET), polyvalerolactone (PVL)) or any other biocompatible material such as those which are wholly or substantially fluid impermeable, flexible, stretchable, deformable, and/or resilient. In some embodiments, the liner can be made from a material that is more flexible than the valve leaflet material. The upper and/or lower end of the liner can be straight, curved, or have any other desired configuration. For example, as shown in the illustrated embodiment, the liner can have a straight edge forming the end. In other embodiments, the end can be patterned to generally correspond to the undulations at one end of the inner frame 120. The liner can be formed of one piece or multiple pieces.

In another embodiment of the liner, the end can extend past the inner frame 120 and can be wrapped around it. Thus, the liner can extend from the interior of the inner frame 120 to the exterior of the inner frame 120. The liner can extend completely around the inner frame 120 for ¼, ⅓, ½, or more of the length of the inner frame 120.

Methods of placement and delivery of the prosthesis 100 can be found in U.S. Patent Publication No. 2018/005629, which is hereby incorporated by reference in its entirety.

Additional Valve Prostheses

FIGS. 18A-20 illustrate alternative embodiments of a prosthesis that can used with the disclosed delivery systems 10 and methodology discussed herein. FIGS. 18A-20 illustrates another alternate embodiment of a prosthesis, which is similar to the prosthesis described with respect to FIG. 33-35 of U.S. Pat. Pub. No. 2018/0055629, except that an outer frame anchoring feature is described in this publication. The entirety of U.S. Pat. Pub. No. 2018/0055629, including the description relating to FIGS. 33-35 as well as all other description relating to the prosthesis, delivery system and methods, are hereby incorporated by reference. The embodiments of FIGS. 18A-20 can have similar or the same features to the other prostheses discussed herein. In some embodiments, the prosthesis may be a single frame prosthesis. In some embodiments, the prosthesis may be a dual frame prosthesis. In some embodiments for use as a replacement mitral valve, the prosthesis includes distal or ventricular anchors similar to those described above (see, for example, anchoring feature 1524 described below), but does not include proximal or atrial anchors.

Figure 18A:
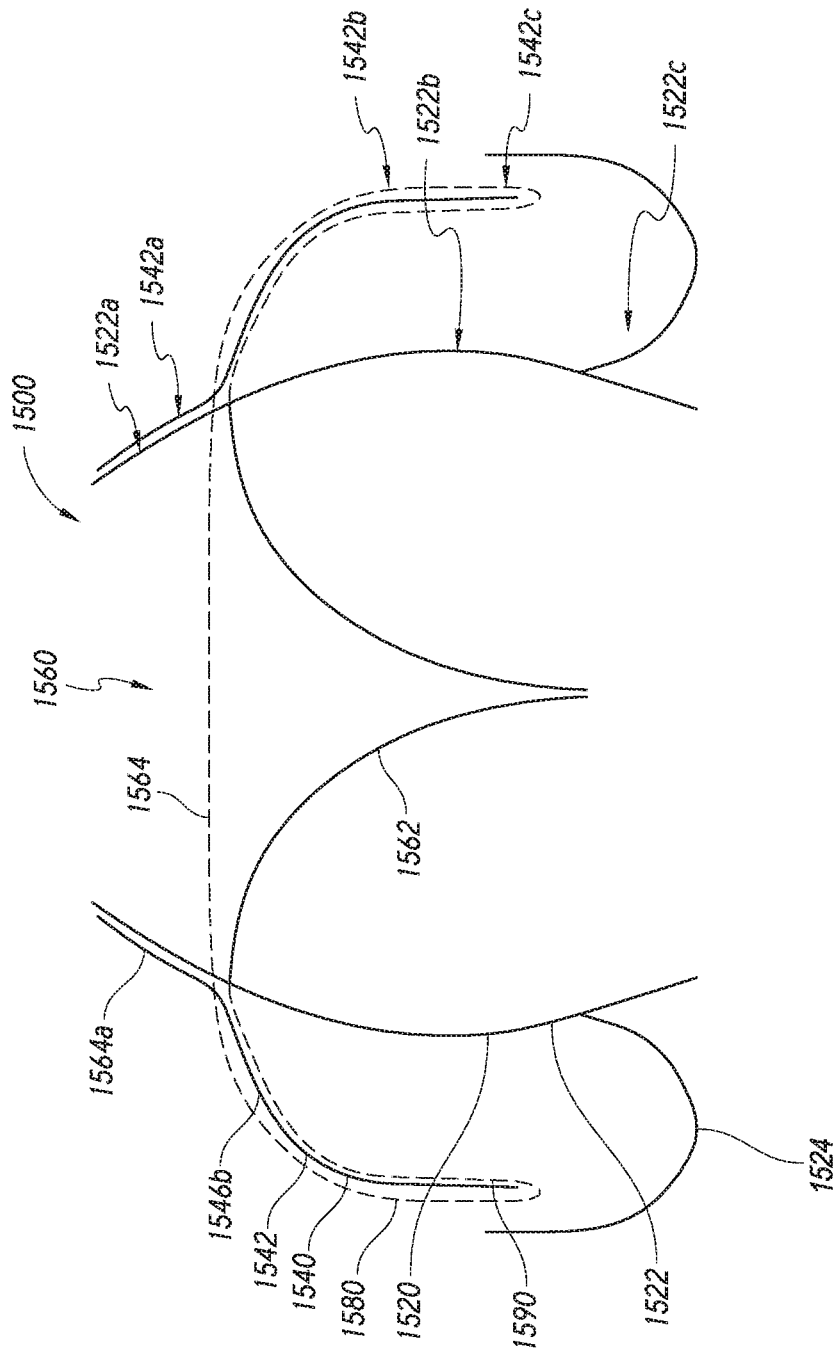
FIGS. 18A-20 illustrate an embodiment of an alternative replacement prosthesis.

With reference next to FIG. 18A, an embodiment of a prosthesis 1500 in an expanded configuration is illustrated. The prosthesis 1500 can include an inner frame 1520, an outer frame 1540, a valve body 1560, and one or more skirts, such as an outer skirt 1580 and an inner skirt 1590.

With reference first to the inner frame 1520, the inner frame 1520 can include an inner frame body 1522 and an inner frame anchoring feature 1524. The inner frame body 1522 can have an upper region 1522a, an intermediate region 1522b, and a lower region 1522c. As shown, the inner frame body 1522 can have a generally bulbous shape such that the diameters of the upper region 1522a and the lower region 1522c are less than the diameter of the intermediate region 1522b. The diameter of the upper region 1522a can be less than the diameter of the lower region 1522c. This can beneficially allow the use of a smaller valve body 1560 within the inner frame 1520 while allowing the inner frame body 1522 to have a larger diameter proximate the connection between the inner frame body 1522 and the inner frame anchoring feature 1524. This larger diameter can reduce the radial distance between the connection and the tip or end of the inner frame anchoring feature 1524. This can beneficially enhance fatigue resistance of the inner frame anchoring feature 1524 by reducing the length of the cantilever.

While the illustrated inner frame body 1522 is bulbous, it is to be understood that the diameters of the upper region 1522a, the intermediate region 1522b, and/or the lower region 1522c can be the same such that the inner frame body 1522 can have more of a constant cross-sectional dimension along one or more regions. Moreover, while the illustrated embodiment includes a lower region 1522a having a greater diameter than the upper region 1522c, it is to be understood that the diameters of the upper and lower regions 1522a, 1522c can be the same or the diameter of the upper region 1522a can be greater than the diameter of the lower region 1522c. Moreover, although the inner frame body 1522 has been described and illustrated as being cylindrical or having circular cross-sections, it is to be understood that all or a portion of the inner frame body 1522 can have a non-circular cross-section such as, but not limited to, a D-shape, an oval or an otherwise ovoid cross-sectional shape.

With reference next to the outer frame 1540 illustrated in FIG. 18A, the outer frame 1540 can be attached to the inner frame 1520 using any suitable fastener and/or other technique. Although the outer frame 1540 is illustrated as a separate component from the inner frame 1520, it is to be understood that the frames 1520, 1540 can be unitarily or monolithically formed.

As shown in the illustrated embodiment, the outer frame 1540 can include an outer frame body 1542. The outer frame body 1542 can have an upper region 1542a, an intermediate region 1542b, and a lower region 1542c. When in an expanded configuration such as a fully expanded configuration, the outer frame body 1542 can have an enlarged shape with the intermediate region 1542b and the lower region 1542c being larger than the upper region 1542a. The enlarged shape of the outer frame body 1542 can advantageously allow the outer frame body 1542 to engage a native valve annulus, native valve leaflets, or other tissue of the body cavity, while spacing the upper end from the heart or vessel wall.

The upper region 1542a of the outer frame body 1542 can include a first section 1546a and a second section 1546b. The first section 1546a can be sized and/or shaped to generally match the size and/or shape of the inner frame 1520. For example, the first section 1546a can have a curvature which matches a curvature of the upper region 1522a of the inner frame body 1522. The second section 1546b can extend radially outwardly away from the inner frame 1520. As shown in the illustrated embodiment, the transition between the first section 1546a and the second section 1546b can incorporate a bend such that the second section 1546b extends radially outwardly at a greater angle relative to the longitudinal axis.

The intermediate region 1542b of the outer frame body 1542 can extend generally downwardly from the outwardly-extending section 1546b of the upper region 1542a. As shown, the intermediate region 1542b can have a generally constant diameter from an upper end to a lower end such that the intermediate region 1542b forms a generally cylindrical shape. The lower region 1542c of the outer frame body 1542 can extend generally downwardly from the lower end of the intermediate region 1542b. As shown, the lower region 1542c of the outer frame body 1542 can have a generally constant diameter from an upper end to a lower end such that the lower region 1542c forms a generally cylindrical shape. As shown, the diameters of the intermediate region 1542b and the lower region 1542c are generally equivalent such that the intermediate region 1542b and the lower region 1542c together form a generally cylindrical shape.

While the intermediate and lower regions 1542b, 1542c have been described as cylindrical, it is to be understood that the diameters of the upper end, the lower end, and/or the portion therebetween can be different. For example, a diameter of the portion between the upper end and the lower end can be larger than the upper end and the lower end such that the intermediate region 1542b and/or lower region 1542c forms a generally bulbous shape. In some embodiments, the diameter of the lower end can be larger than the diameter of the upper end. In other embodiments, the diameter of the upper end can be larger than the diameter of the lower end. Moreover, although the outer frame body 1542 has been described and illustrated as being cylindrical or having circular cross-sections, it is to be understood that all or a portion of the outer frame body 1542 can be have a non-circular cross-section such as, but not limited to, a D-shape, an oval or an otherwise ovoid cross-sectional shape.

The outer frame 1540, such as the outer frame body 1542 can be used to attach or secure the prosthesis 1500 to a native valve, such as a native mitral valve. For example, the intermediate region 1542b of the outer frame body 1542 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1542 can be sized and positioned relative to the inner frame anchoring feature 1524 such that tissue of the body cavity positioned between the outer frame body 1542 and the inner frame anchoring feature 1524, such as native valve leaflets and/or a native valve annulus, can be engaged or pinched to further secure the prosthesis 1500 to the tissue.

With continued reference to the prosthesis 1500 illustrated in FIG. 18A, the valve body 1560 is attached to the inner frame 1520 within an interior of the inner frame body 1522. The valve body 1560 functions as a one-way valve to allow blood flow in a first direction through the valve body 1560 and inhibit blood flow in a second direction through the valve body 1560.

The valve body 1560 can include a plurality of valve leaflets 1562, for example three leaflets 1562, which are joined at commissures. The valve body 1560 can include one or more intermediate components 1564. The intermediate components 1564 can be positioned between a portion of, or the entirety of, the leaflets 1562 and the inner frame 1520 such that at least a portion of the leaflets 1542 are coupled to the frame 1520 via the intermediate component 1564. In this manner, a portion of, or the entirety of, the portion of the valve leaflets 1562 at the commissures and/or an arcuate edge of the valve leaflets 1562 are not directly coupled or attached to the inner frame 1520 and are indirectly coupled or "float" within the inner frame 1520. For example, a portion of, or the entirety of, the portion of the valve leaflets 1562 proximate the commissures and/or the arcuate edge of the valve leaflets 1562 can be spaced radially inward from an inner surface of the inner frame 1520. By using one or more intermediate components 1564, the valve leaflets 1562 can be attached to non-cylindrical frames 1520 and/or frames 1520 having a diameter larger than that of the diameter of the valve leaflets 1562.

With reference next to the outer skirt 1580 illustrated in FIG. 18A, the outer skirt 1580 can be attached to the inner frame 1520 and/or outer frame 1540. As shown, the outer skirt 1580 can be positioned around and secured to a portion of, or the entirety of, the exterior of the outer frame 1540. The skirt 1580 can also be secured to a portion of the valve body 1560 such as, but not limited to, the intermediate components 1564. For example, the skirt 1580 can be attached to an inflow region of the intermediate components 1564. As shown, the outer skirt 1580 can follow the contours of the outer frame 1540; however, it is to be understood that at least a portion of the skirt 1580 can be spaced apart from at least a portion of both the inner frame 1520 and the outer frame 1540.

With reference next to the inner skirt 1590 illustrated in FIG. 18A, the inner skirt 1590 can be attached to the valve body 1560 and the outer skirt 1580. As shown, a first end of the inner skirt 1590 can be coupled to the valve body 1560 along portions of the valve body 1560 which are proximate the inner frame 1520. A second end of the inner skirt 1590 can be attached to the lower region of the outer skirt 1580. In so doing, a smooth surface can be formed under each of the leaflets. This can beneficially enhance hemodynamics by allowing blood to more freely circulate and reducing areas of stagnation. In some embodiments, the inner skirt 1590 can beneficially reduce contact between the outer frame body 1542 and the inner frame body 1522.

Although the prosthesis 1500 has been described as including an inner frame 1520, an outer frame 1540, a valve body 1560, and skirts 1580, 1590, it is to be understood that the prosthesis 1500 need not include all components. For example, in some embodiments, the prosthesis 1500 can include the inner frame 1520, the outer frame 1540, and the valve body 1560 while omitting the skirt 1580. Moreover, although the components of the prosthesis 1500 have been described and illustrated as separate components, it is to be understood that one or more components of the prosthesis 1500 can be integrally or monolithically formed. For example, in some embodiments, the inner frame 1520 and the outer frame 1540 can be integrally or monolithically formed as a single component.

Figure 18B:
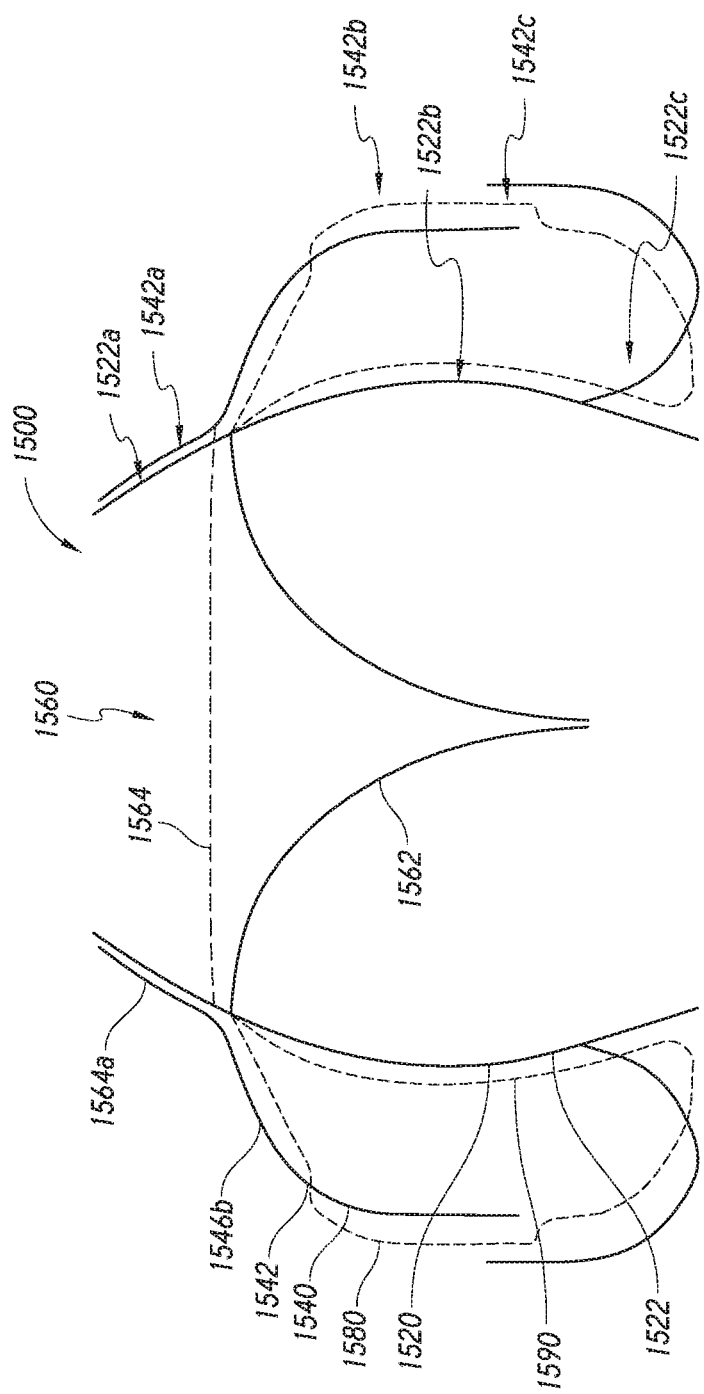

FIG. 18B illustrates an alternate embodiment of FIG. 18A with modifications to the design of the skirts (or cloth) 1580/1590. As shown, the skirts 1580/1590 can contact both the inner frame 1520 and outer frame 1540. The skirts 1580/1590 can start on the inside of the outer 1540, transition to the outside of the outer frame 1540, then attach to the bottom of the outside of the inner frame 1520, then proceed up along the outside of the inner frame 1520. By closing the skirts 1580/1590, this could avoid/reduce clot formation/embolization.

Figure 19:
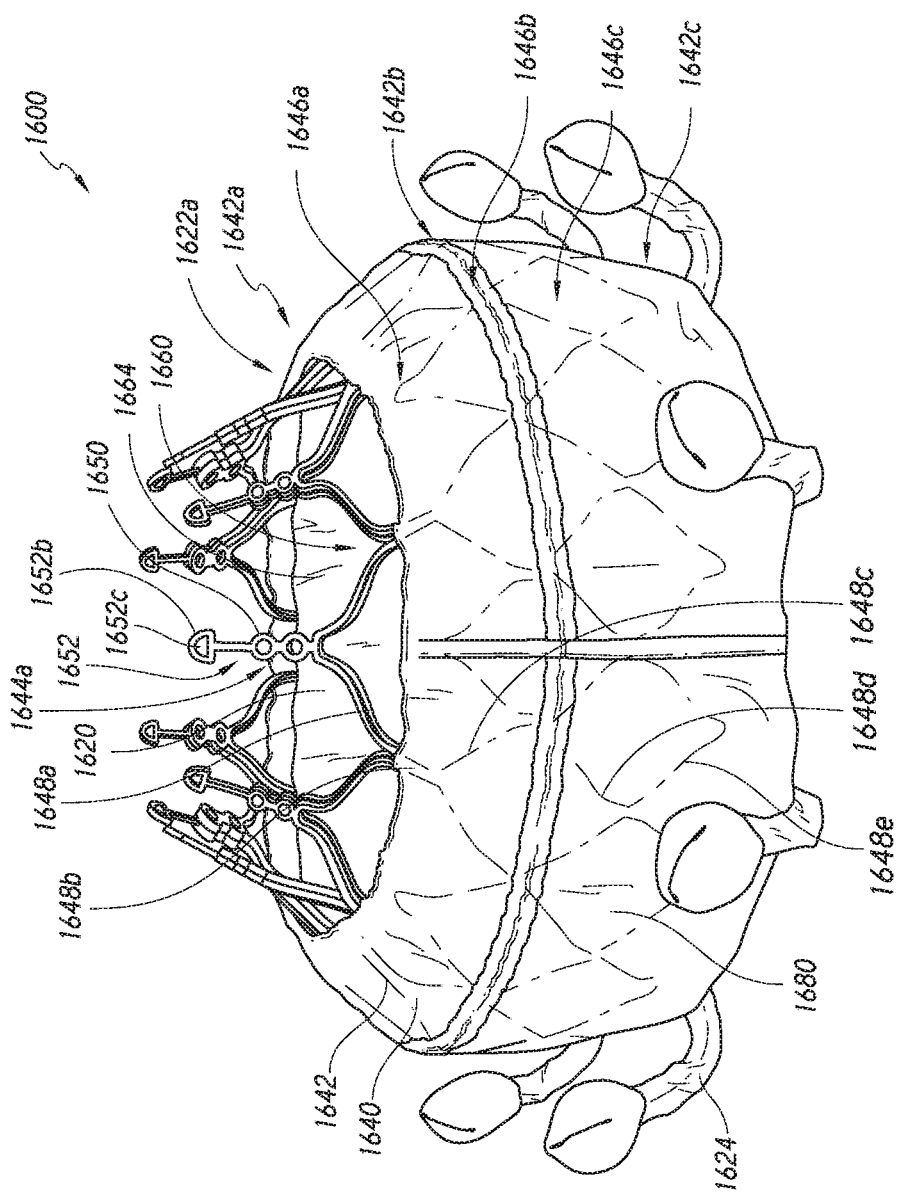
Figure 20:
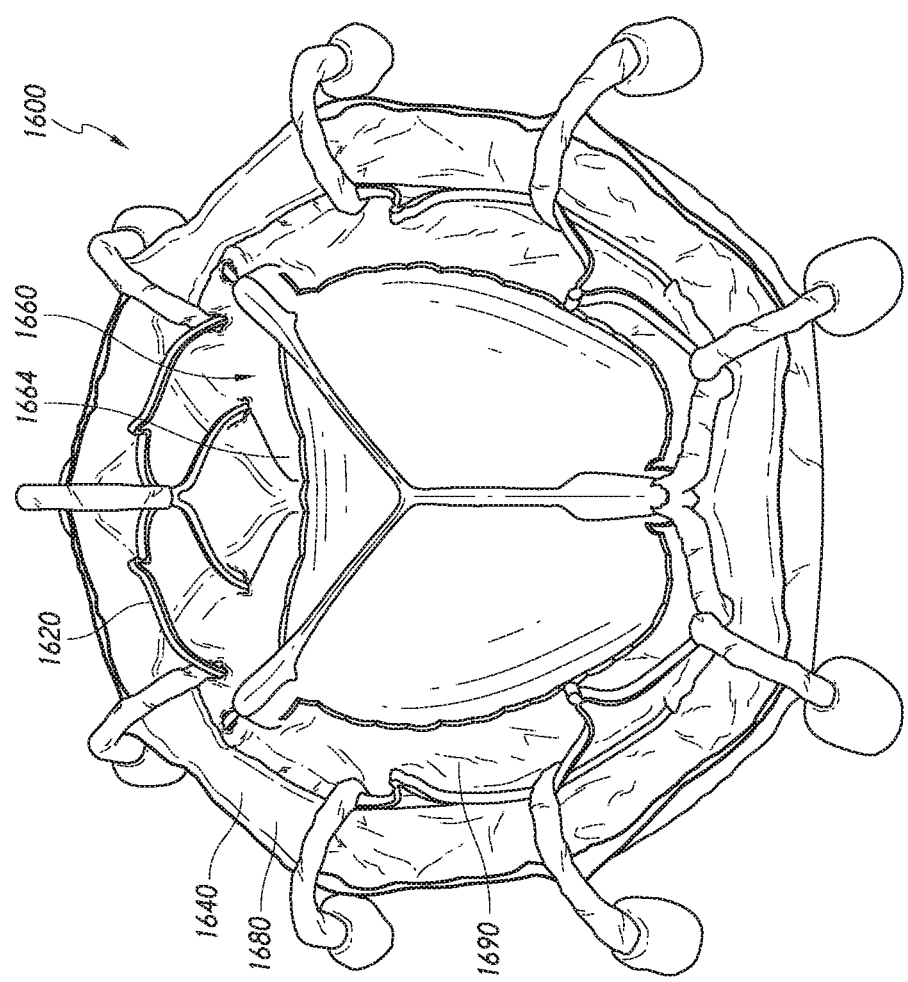

With reference next to FIGS. 19-20, an embodiment of a prosthesis 1600 in an expanded configuration is illustrated. This prosthesis 1600 may be similar in construction to the prosthesis 1500 described above. The prosthesis 1600 can include an inner frame 1620, an outer frame 1640, a valve body 1660, and one or more skirts, such as an outer skirt 1680 and an inner skirt 1690.

With reference first to the outer frame 1640 illustrated in FIGS. 19-20, the outer frame 1640 can be attached to the inner frame 1620 using any known fasteners and/or techniques. Although the outer frame 1640 is illustrated as a separate component from the inner frame 1620, it is to be understood that the frames 1620, 1640 can be unitarily or monolithically formed.

As shown in the illustrated embodiment, the outer frame 1640 can include an outer frame body 1642. The outer frame body 1642 can have an upper region 1642a, an intermediate region 1642b, and a lower region 1642c. At least a portion of the upper region 1642a of the outer frame body 1642 can be sized and/or shaped to generally match the size and/or shape of an upper region 1622a of the inner frame 1620. As shown in the illustrated embodiment, the upper region 1642a of the outer frame body 1642 can include one or more struts which generally match the size and/or shape of struts of the inner frame 1620. This can locally reinforce a portion of the prosthesis 1600 by effectively increasing the wall thickness of the combined struts.

When in an expanded configuration such as in a fully expanded configuration, the outer frame body 1642 can have a shape similar to that of outer frame body 1542 described above in connection with FIG. 18A. As shown, the intermediate region 1642b and the lower region 1642c can have a diameter which is larger than the diameter of the upper region 1642a. The upper region 1642a of the outer frame body 1642 can have a decreasing diameter from a lower end to an upper end such that the upper region 1642a is inclined or curved radially inwards towards the longitudinal axis of the prosthesis 1600. Although the outer frame body 1642 has been described and illustrated as being cylindrical or having circular cross-sections, it is to be understood that all or a portion of the outer frame body 1642 can be have a non-circular cross-section such as, but not limited to, a D-shape, an oval or an otherwise ovoid cross-sectional shape.

With continued reference to the outer frame 1600 illustrated in FIG. 19, the outer frame body 1642 can include a plurality of struts with at least some of the struts forming cells 1646a-c. Any number of configurations of struts can be used, such as rings of undulating struts shown forming ellipses, ovals, rounded polygons, and teardrops, but also chevrons, diamonds, curves, and various other shapes.

The upper row of cells 1646a can have an irregular octagonal shape such as a "heart" shape. This additional space can beneficially allow the outer frame 1640 to retain a smaller profile when crimped. The cell 1646a can be formed via a combination of struts. As shown in the illustrated embodiment, the upper portion of cells 1646a can be formed from a set of circumferentially-expansible struts 1648a having a zig-zag or undulating shape forming a repeating "V" shape. The struts 1648a can extend radially outwardly from an upper end to a lower end. These struts can generally match the size and/or shape of struts of the inner frame 1620.

The middle portion of cells 1646a can be formed from a set of struts 1648b extending downwardly from bottom ends of each of the "V" shapes. The struts 1648b can extend radially outwardly from an upper end to a lower end. The portion of the cells 1646a extending upwardly from the bottom end of struts 1648b may be considered to be a substantially non-foreshortening portion of the outer frame 1640.

The lower portion of cells 1646a can be formed from a set of circumferentially-expansible struts 1648c having a zig-zag or undulating shape forming a repeating "V" shape. As shown in the illustrated embodiment, the struts 1648c can incorporate a curvature such that the lower end of struts 1648c extend more parallel with the longitudinal axis than the upper end of the struts 1648c. One or more of the upper ends or tips of the circumferentially-expansible struts 1648c can be a "free" apex which is not connected to a strut. For example, as shown in the illustrated embodiment, every other upper end or tip of circumferentially-expansible struts 1648b is a free apex. However, it is to be understood that other configurations can be used. For example, every upper apex along the upper end can be connected to a strut.

The middle and/or lower rows of cells 1646b-c can have a different shape from the cells 1646a of the first row. The middle row of cells 1646b and the lower row of cells 1646c can have a diamond or generally diamond shape. The diamond or generally diamond shape can be formed via a combination of struts.

The upper portion of cells 1646b can be formed from the set of circumferentially-expansible struts 1648c such that cells 1646b share struts with cells 1646a. The lower portion of cells 1646b can be formed from a set of circumferentially-expansible struts 1648d. As shown in the illustrated embodiment, one or more of the circumferentially-expansible struts 1648d can extend generally in a downward direction generally parallel to the longitudinal axis of the outer frame 1640.

The upper portion of cells 1646c can be formed from the set of circumferentially-expansible struts 1648d such that cells 1646c share struts with cells 1646b. The lower portion of cells 1646c can be formed from a set of circumferentially-expansible struts 1648e. Circumferentially-expansible struts 1648e can extend generally in a downward direction.

As shown in the illustrated embodiment, there can be a row of nine cells 1646a and a row of eighteen cells 1646b-c. While each of the cells 1646a-c are shown as having the same shape as other cells 1646a-c of the same row, it is to be understood that the shapes of cells 1646a-c within a row can differ. Moreover, it is to be understood that any number of rows of cells can be used and any number of cells may be contained in the rows.

As shown in the illustrated embodiment, the outer frame 1600 can include a set of eyelets 1650. The upper set of eyelets 1650 can extend from an upper region 1642a of the outer frame body 1642. As shown, the upper set of eyelets 1650 can extend from an upper portion of cells 1646a, such as the upper apices of cells 1646a. The upper set of eyelets 1650 can be used to attach the outer frame 1640 to the inner frame 1620. For example, in some embodiments, the inner frame 1620 can include one or more eyelets which correspond to the eyelets 1650. In such embodiments, the inner frame 1620 and outer frame 1640 can be attached together via eyelets 1650 and corresponding eyelets on the inner frame 1620. For example, the inner frame 1620 and outer frame 1640 can be sutured together through said eyelets or attached via other means, such as mechanical fasteners (e.g., screws, rivets, and the like).

As shown, the set of eyelets 1650 can include two eyelets extending in series from each "V" shaped strut. This can reduce the likelihood that the outer frame 1640 twists along an axis of the eyelet. However, it is to be understood that some "V" shaped struts may not include an eyelet. Moreover, it is to be understood that a fewer or greater number of eyelets can extend from a "V" shaped strut.

The outer frame 1640 can include a set of locking tabs 1652 extending from at or proximate an upper end of the upper region 1642a. As shown, the locking tabs 1652 can extend upwardly from the set of eyelets 1650. The outer frame 1640 can include twelve locking tabs 1652, however, it is to be understood that a greater number or lesser number of locking tabs can be used. The locking tabs 1652 can include a longitudinally-extending strut 1652a. At an upper end of the strut 1652a, the locking tab 1652 can include an enlarged head 1652b. As shown, the enlarged head 1652b can have a semi-circular or semi-elliptical shape forming a "mushroom" shape with the strut 1652a. The locking tab 1652 can include an eyelet 1652c which can be positioned through the enlarged head 1652b. It is to be understood that the locking tab 1652 can include an eyelet at other locations, or can include more than a single eyelet.

The locking tab 1652 can be advantageously used with multiple types of delivery systems. For example, the shape of the struts 1652a and the enlarged head 1652b can be used to secure the outer frame 1640 to a "slot" based delivery system, such as the inner retention member 40 described above. The eyelets 1652c and/or eyelets 1650 can be used to secure the outer frame 1640 to a "tether" based delivery system such as those which utilize sutures, wires, or fingers to control delivery of the outer frame 1640 and the prosthesis 1600. This can advantageously facilitate recapture and repositioning of the outer frame 1640 and the prosthesis 1600 in situ.

The outer frame 1640, such as the outer frame body 1642 can be used to attach or secure the prosthesis 1600 to a native valve, such as a native mitral valve. For example, the intermediate region 1642b of the outer frame body 1642 and/or the outer anchoring feature 1644 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1642 can be sized and positioned relative to the inner frame anchoring feature 1624 such that tissue of the body cavity positioned between the outer frame body 1642 and the inner frame anchoring feature 1624, such as native valve leaflets and/or a native valve annulus, can be engaged or pinched to further secure the prosthesis 1600 to the tissue. As shown, the inner frame anchoring feature 1624 includes nine anchors; however, it is to be understood that a fewer or greater number of anchors can be used. In some embodiments, the number of individual anchors can be chosen as a multiple of the number of commissures for the valve body 1660. For example, for a valve body 1660 have three commissures, the inner frame anchoring feature 1624 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. In some embodiments, the number of individual anchors does not correspond to the number of commissures of the valve body 1660.

With continued reference to the prosthesis 1600 illustrated in FIGS. 19-20, the valve body 1660 is attached to the inner frame 1620 within an interior of the inner frame body 1622. The valve body 1660 functions as a one-way valve to allow blood flow in a first direction through the valve body 1660 and inhibit blood flow in a second direction through the valve body 1660.

The valve body 1660 can include a plurality of valve leaflets 1662, for example three leaflets 1662, which are joined at commissures. The valve body 1660 can include one or more intermediate components 1664. The intermediate components 1664 can be positioned between a portion of, or the entirety of, the leaflets 1662 and the inner frame 1620 such that at least a portion of the leaflets 1642 are coupled to the frame 1620 via the intermediate component 1664. In this manner, a portion of, or the entirety of, the portion of the valve leaflets 1662 at the commissures and/or an arcuate edge of the valve leaflets 1662 are not directly coupled or attached to the inner frame 1620 and are indirectly coupled or "float" within the inner frame 1620.

With reference next to the outer skirt 1680 illustrated in FIG. 19, the outer skirt 1680 can be attached to the inner frame 1620 and/or outer frame 1640. As shown, the outer skirt 1680 can be positioned around and secured to a portion of, or the entirety of, the exterior of the outer frame 1640. The inner skirt 1690 can be attached to the valve body 1660 and the outer skirt 1680. As shown in FIG. 40, a first end of the inner skirt 1690 can be coupled to the valve body 1660 along portions of the valve body 1660 which are proximate the inner frame 1620. A second end of the inner skirt 1690 can be attached to the lower region of the outer skirt 1680. In so doing, a smooth surface can be formed along under each of the leaflets. This can beneficially enhance hemodynamics by allowing blood to more freely circulate and reducing areas of stagnation.

Although the prosthesis 1600 has been described as including an inner frame 1620, an outer frame 1640, a valve body 1660, and skirts 1680, 1690, it is to be understood that the prosthesis 1600 need not include all components. For example, in some embodiments, the prosthesis 1600 can include the inner frame 1620, the outer frame 1640, and the valve body 1660 while omitting the skirt 1680. Moreover, although the components of the prosthesis 1600 have been described and illustrated as separate components, it is to be understood that one or more components of the prosthesis 1600 can be integrally or monolithically formed. For example, in some embodiments, the inner frame 1620 and the outer frame 1640 can be integrally or monolithically formed as a single component.

Figure 21:
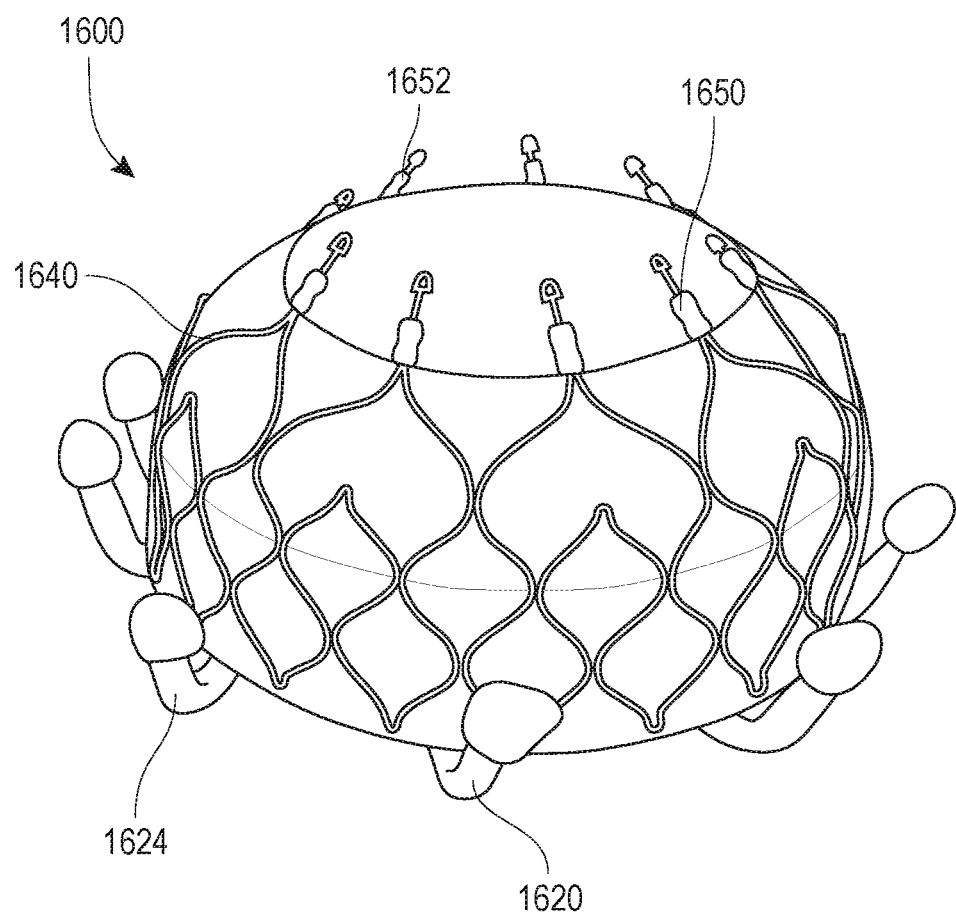
FIG. 21 illustrates an embodiment of a replacement prostheses.

FIG. 21 illustrates an embodiments of the frame of prosthesis 1600 which can have two different sizes. The prostheses 1600 may just be scaled for size, and there are no substantive/functional differences between the two. Prosthesis 100 can also be made of various sizes.

Figure 22:
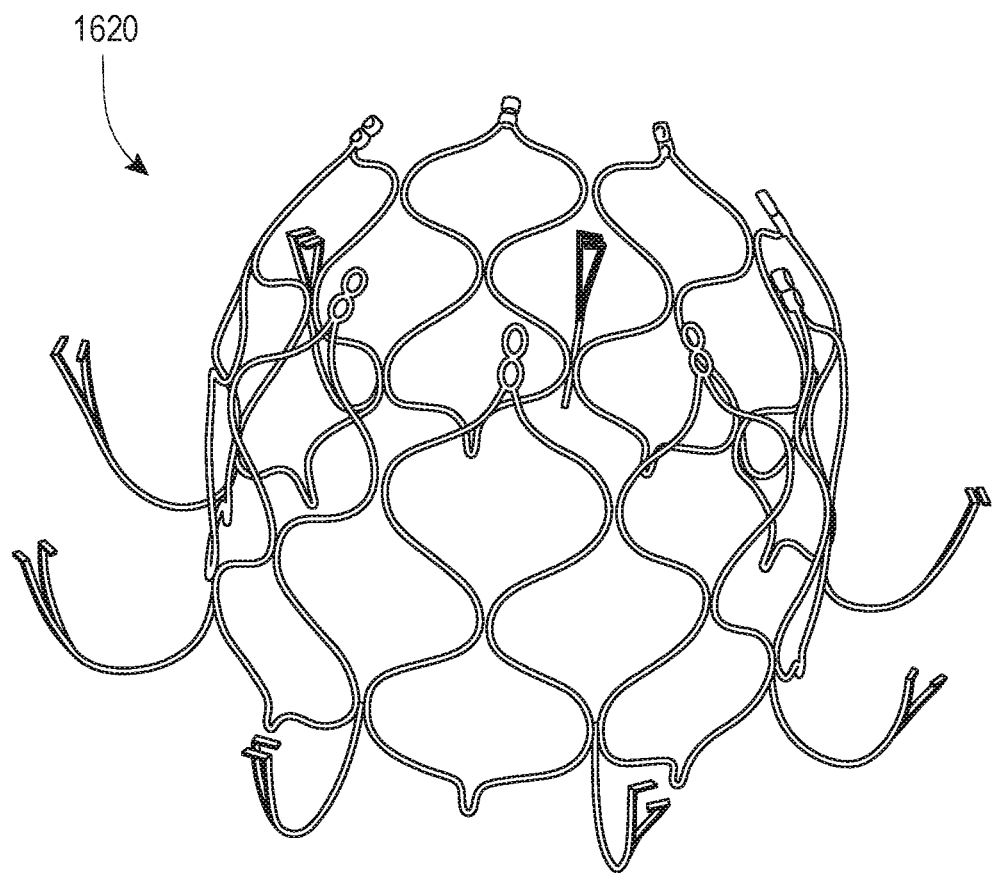
FIG. 22 shows an embodiment of an inner frame of an alternate replacement prosthesis.
Figure 23:
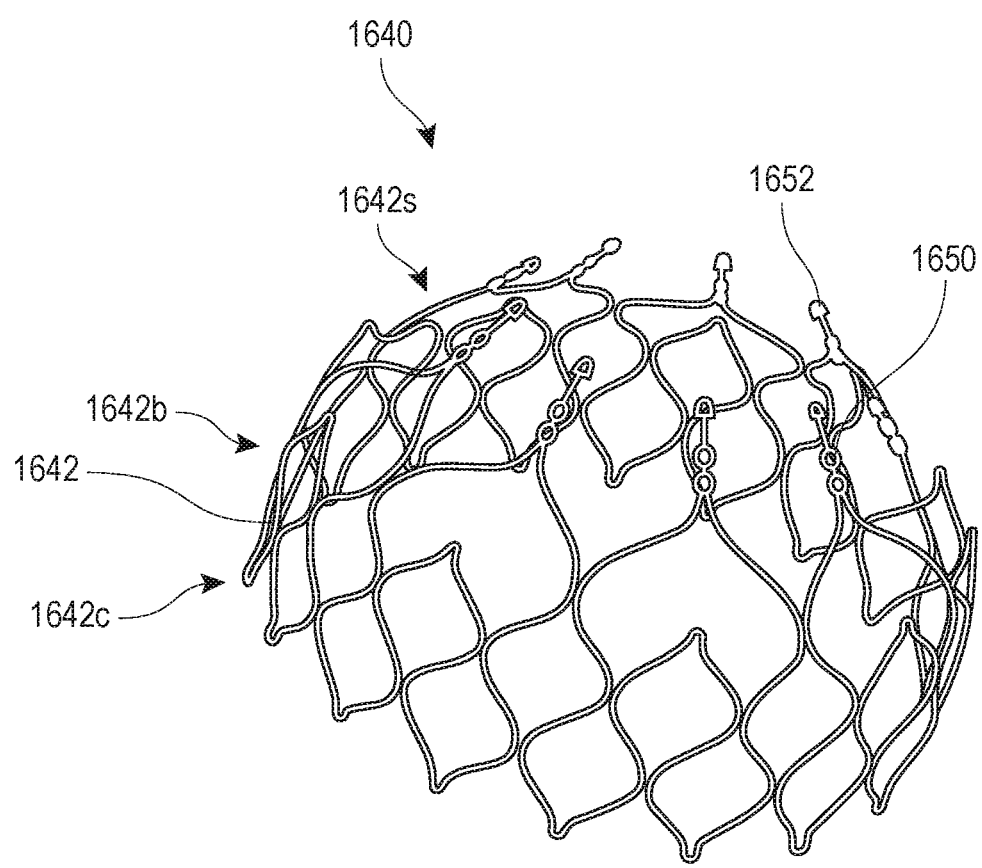
FIG. 23 shows an embodiment of an outer frame of an alternate replacement prosthesis.

FIG. 22 shows the inner frame 1520 of prosthesis 1600 and FIG. 23 shows the outer frame 1540 of prosthesis 1600.

FIG. 24 illustrates a distal end of an inner frame anchoring feature 1624 of prosthesis 1600, though the same structure can be used for any of the prostheses 100 disclosed herein. As shown, the distal tip 1625 of the inner frame anchoring feature 1624 can include two struts 1627 ending with generally L-shaped anchors 1629 that face circumferentially opposite directions. As shown, the L-shaped anchors 1629 are not circumferentially aligned so that each L-shaped anchor 1629 has a free end. For example, a first of the struts 1627 can bend radially inward as compared to a second of the struts 1627. The L-shaped anchors 1629 can be spaced 1, 2, 3, 4, 5, or 6 mm away from each other. In some embodiments, more struts 1627 and more anchors 1629 can be used. The L-shaped anchors 1629 provide for a greater area of attachment of any cushions/sutures, thereby preventing slippage or movement of the cushions.

Anchor Separator

FIGS. 25A-27B illustrate embodiments of an anchor separator that can be used with any of the above-described embodiments of prostheses.

In some loading procedures, the inner frame anchoring features disclosed herein may not load uniformly, but instead cross or spiral as they load. This non-uniform loading can be disadvantageous as it can cause non-uniform straining of the inner frame anchoring feature, which may make the prosthesis more prone to fracturing or cracking. The non-uniform loading can also cause increases in valve loading and/or deployment forces, which may cause further loads on the frame, on soft tissue, or on fabric/suturing components.

Figure 25A:
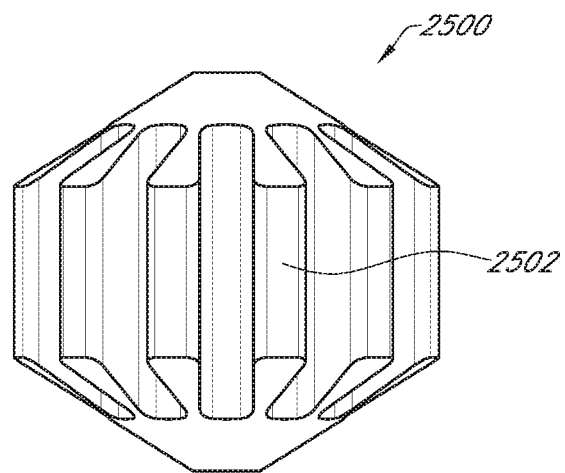
FIGS. 25A-25B illustrate embodiments of an anchor separator.
Figure 25B:
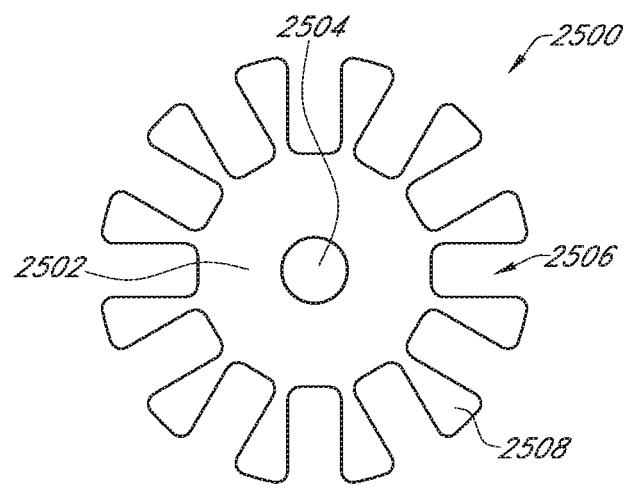

Accordingly, FIGS. 25A-25B illustrate an embodiment of an anchor separator 2500. As shown, the anchor separator 2500 can be a body 2502 having a lumen 2504 extending generally along a longitudinal centerline of the body 2502, and can include a plurality of longitudinally extending groves 2506 formed by a plurality of extensions 2508 on an outer radial surface of the body 2502. The body 2502 can be generally tubular with the extensions 2508 extending radially off of the tubular body 2502.

As shown, the extensions 2508 can be generally triangular shaped having a base of the triangle being the outer radial-most position, though the particular shape is not limiting. Adjacent extensions 2508 form generally rectangular grooves 2506 or slots between them along a longitudinal length of the body 2502 configured to receive the inner frame anchoring features 1624. In some embodiments, the extensions/grooves 2508/2506 can extend fully along a longitudinal length of the body 2502. In some embodiments, the extensions/grooves 2508/2506 can extend 95%, 90%, 85%, 80%, or 75% of a longitudinal length of the body 2502. In some embodiments, the extensions/grooves 2508/2506 can extend greater than 95%, 90%, 85%, 80%, or 75% of a longitudinal length of the body 2502. In some embodiments, the extensions/grooves 2508/2506 can extend less than 95%, 90%, 85%, 80%, or 75% of a longitudinal length of the body 2502.

In some embodiments, the body 2502 can have 3, 4, 5, 6, 7, 8, 9, 10, 11, or 12 grooves 2506. In some embodiments, the body 2502 can have greater than 3, 4, 5, 6, 7, 8, 9, 10, 11, or 12 grooves 2506. In some embodiments, the body can have less than 3, 4, 5, 6, 7, 8, 9, 10, 11, or 12 grooves 2506. In some embodiments, the body 2502 can have the same amount of grooves 2506 as the prosthesis has inner frame anchoring features 1624. In some embodiments, the body 2502 can have fewer grooves 2506 than the replacement valve has inner frame anchoring features 1624. In some embodiments, the body 2502 can have more grooves 2506 than the replacement valve has inner frame anchoring features 1624.

In some embodiments, such as shown in FIGS. 25A-25B, the body 2502 can be tapered radially inwards towards the proximal and distal ends of the body 2502 (e.g., generally along a longitudinal axis). Further, as shown, the extensions 2508 can similarly be radially tapered inwards on the proximal and distal ends. This can reduce or prevent the separator 2500 from catching on the deployed prostheses when the delivery system is retracted through the prosthesis.

Figure 26:
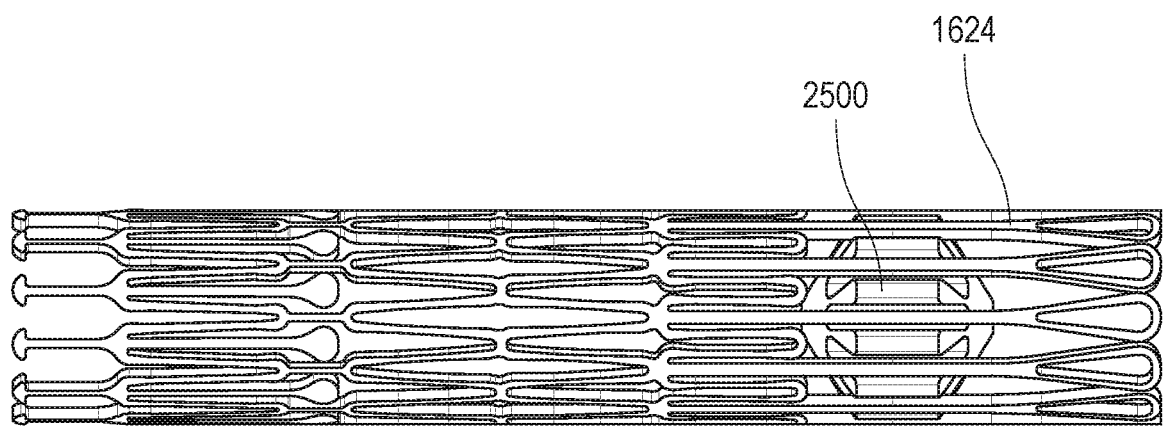
FIG. 26 illustrates an embodiment of an anchor separator within a frame of a replacement prosthesis.
Figure 27A:
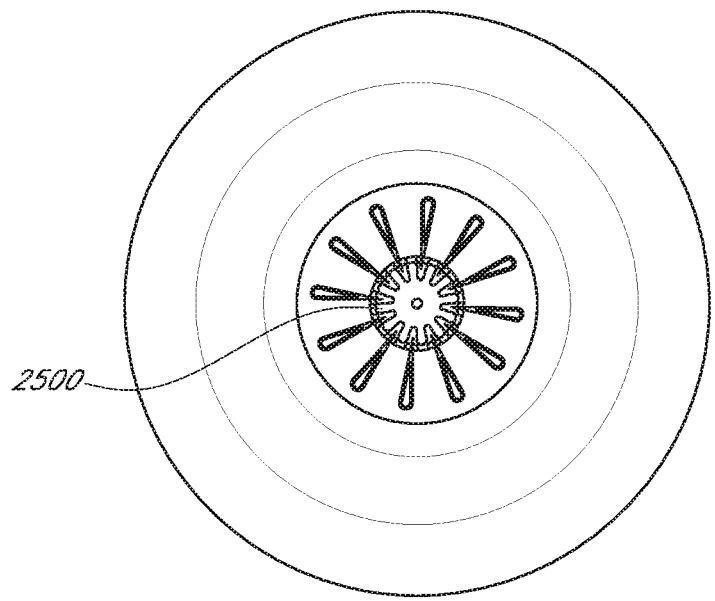
FIGS. 27A-27B show and embodiment of an anchor separator in use with a replacement prosthesis.
Figure 27B:
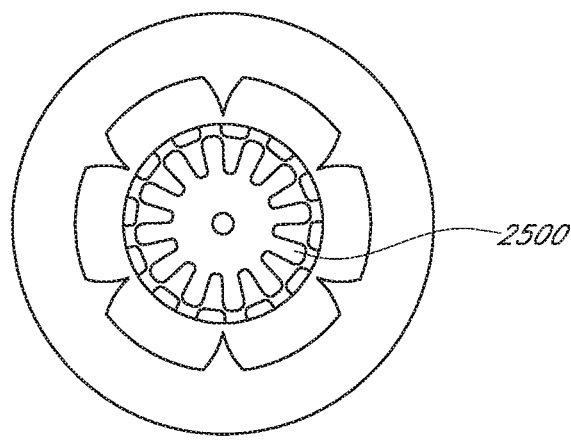

Accordingly, the inner frame anchoring features can be releasably loaded into the grooves 2506 to prevent them from twisting, rotating, moving, or displacing out of plane. The inner frame anchoring features can be retained in the grooves 2506 by a radially outer sheath, and when the sheath is removed the inner frame anchoring features 1624 can release from the grooves 2506. An example prosthesis is shown in FIG. 26 with anchoring features 1624 (but similarly could be used for 124) inserted into the separator 2500. The inner frame anchoring features can be loaded uniformly around a circumference of the separator 2500. FIGS. 27A-27B illustrate the separator 2500 used with a delivery system, such as delivery system 10 disclosed below.

In some embodiment, the separator 2500 can slide along a shaft, such as the nosecone shaft of the delivery system described in US Pat. App. Pub. Nos. 2017/0056169, 2016/0317301, 2017/0056171, 2019/0008640, the entirety of each of which is hereby incorporated by reference. In some embodiments, the separator 2500 can be fixed to the shaft. In some embodiments, the separator 2500 can have an axial/longitudinal degree of freedom along the shaft. In some embodiments, the separator 2500 can have a rotational degree of freedom along the shaft. Preferably, the separator 2500 can be axially fixed but can have free rotation. This can allow the separator 2500 to be adjusted as the prosthesis gets pulled inside the delivery system catheter, thereby aligning all of the inner frame anchoring features circumferentially. In some embodiments, the separator 2500 may not be attached to the delivery system.

Delivery System Suture Attachment

Figure 28A:
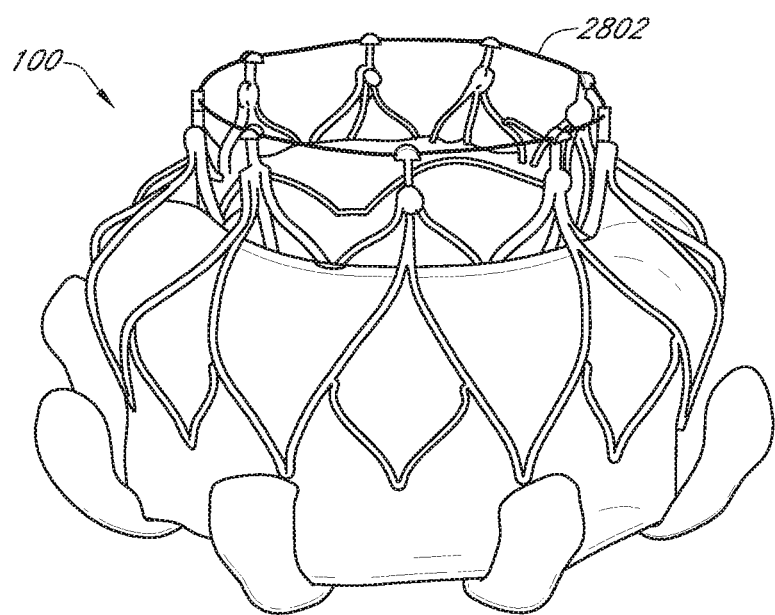
FIGS. 28A-28B show an embodiment of a suturing system for attachment to a delivery system.
Figure 28B:
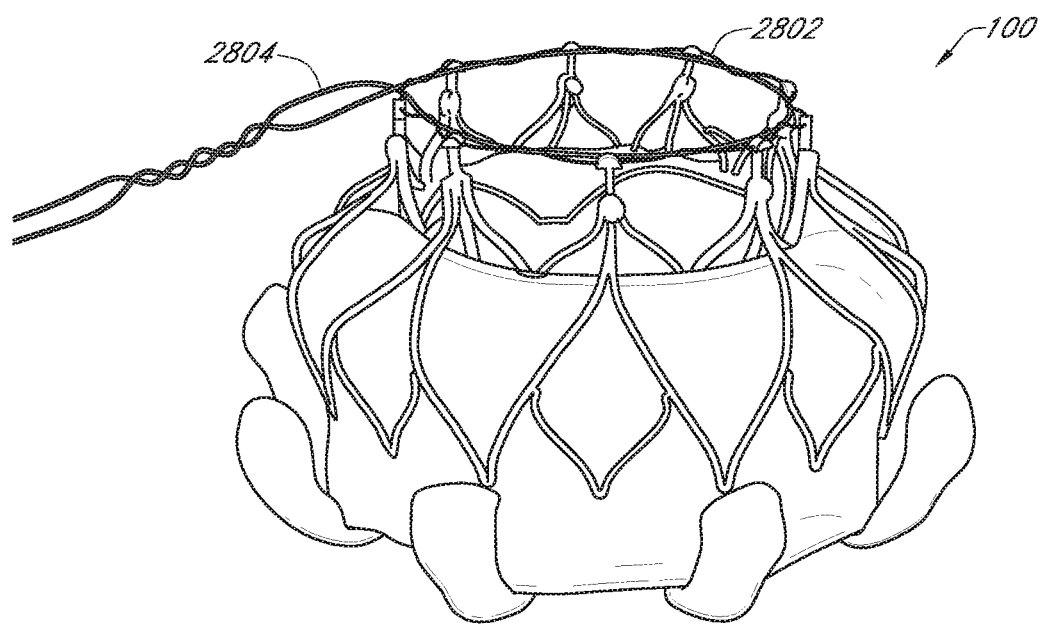

FIGS. 28A-28B illustrate a prosthesis 100, including any discussed above, having a suture 2802 configured to attach to a delivery system, such as the one discussed below. For example, fingers, knobs, or shafts in the delivery system may releasable hold onto the suture 2802. In some embodiments, the delivery system can include an additional suture for connecting to suture 2802, such as shown in FIG. 28B. The additional suture 2804 can wrap around and/or intertwine with suture 2802 to connect the prosthesis 100 to the delivery system.

The suture 2802 can be permanently attached to the prosthesis 100 or can be removed upon delivery. In some embodiments, the suture 2802 can be biodegradable.

As shown, the suture 2802 can generally extend around an outer circumference of the atrial end of the prosthesis 100. In some embodiments, the suture 2802 can extend fully or partially around the circumference. The suture 2802 can be attached to the prosthesis 100 in a number of ways. In some embodiments, the suture 2802 can pass through the eyelets 120 in the outer frame. The suture 2802 can pass through all or some of the eyelets 120. In some embodiments, the suture 2802 can wrap or otherwise attach to the tabs 104 of the inner frame. In some embodiments, the suture 2802 can attach to both the outer frame and the inner frame. In some embodiments, the suture 2802 can be compressed between the two frames. In some embodiments, the suture 2802 can be attached, such as chemically or mechanically, to the prosthesis 100.

Delivery System

Figure 35:
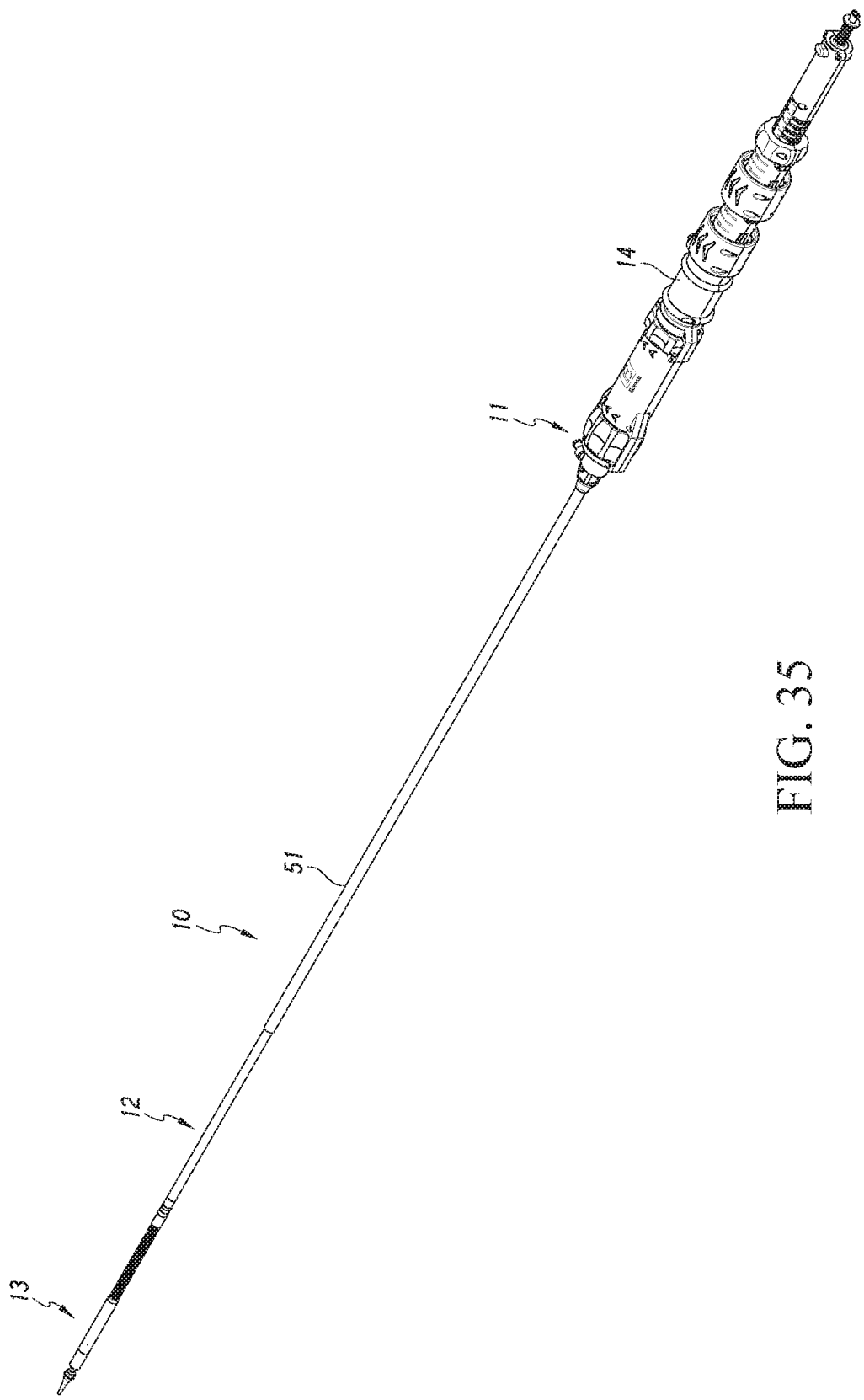
FIG. 35 shows an embodiment of a delivery system for use with any of the prostheses disclosed herein.

FIG. 35 illustrates an embodiment of a delivery device, system, or assembly 10, such as described in U.S. Pat. Pub. No. 2019/0008640, hereby incorporated by reference in its entirety. The delivery system 10 can be used to deploy a prosthesis, such as a replacement heart valve, within the body. In some embodiments, the delivery system 10 can use a dual plane deflection approach to properly delivery the prosthesis. Replacement heart valves can be delivered to a patient's heart mitral valve annulus or other heart valve location in various manners, such as by open surgery, minimally-invasive surgery, and percutaneous or transcatheter delivery through the patient's vasculature. Example transfemoral approaches may be found in U.S. Pat. Pub. No. 2015/0238315, filed Feb. 20, 2015, the entirety of which is hereby incorporated by reference in its entirety. While the delivery system 10 is described in connection with a percutaneous delivery approach, and more specifically a transfemoral delivery approach, it should be understood that features of delivery system 10 can be applied to other delivery system, including delivery systems for a transapical delivery approach.

The delivery system 10 can be used to deploy a prosthesis, such as a replacement heart valve as described elsewhere in this specification, within the body. The delivery system 10 can receive and/or cover portions of the prosthesis such as a first end (e.g., atrial end) and second end (e.g., ventricular end) of the prosthesis 100. For example, the delivery system 10 may be used to deliver an expandable implant or prosthesis 100, where the prosthesis 100 includes the first end and the second end, and wherein the second end is configured to be deployed or expanded before the first end. Discussion of the attachment of the prosthesis 100 to the delivery system 10 can be found in U.S. Publication No. 2015/0328000A1, hereby incorporated by reference in its entirety. Further details and embodiments of a replacement heart valve or prosthesis and its method of implantation are described in U.S. Publication Nos. 2015/0328000 and 2016/0317301 the entirety of each of which is hereby incorporated by reference and made a part of this specification.

The delivery system 10 can be relatively flexible. In some embodiments, the delivery system 10 is particularly suitable for delivering a replacement heart valve to a mitral valve location through a transseptal approach (e.g., between the right atrium and left atrium via a transseptal puncture).

As shown in FIG. 35, the delivery system 10 can include a shaft assembly 12 comprising a proximal end 11 and a distal end 13, wherein a handle 14 is coupled to the proximal end of the assembly 12. The shaft assembly 12 can be used to hold the prosthesis for advancement of the same through the vasculature to a treatment location. The delivery system 10 can further comprise a relatively rigid live-on (or integrated) sheath 51 surrounding the shaft assembly 12 that can prevent unwanted motion of the shaft assembly 12. The live-on sheath 51 can be attached at a proximal end of the shaft assembly 12 proximal to the handle 14, for example at a sheath hub. The shaft assembly 12 can include an implant retention area at its distal end that can be used for this purpose. In some embodiments, the shaft assembly 12 can hold an expandable prosthesis in a compressed state at implant retention area for advancement of the prosthesis 100 within the body. The shaft assembly 12 may then be used to allow controlled expansion of the prosthesis 100 at the treatment location. In some embodiments, the shaft assembly 12 may be used to allow for sequential controlled expansion of the prosthesis 100. In some embodiments, the prosthesis 100 may be rotated in the implant retention area.

As discussed in U.S. Pat. Pub. No. 2019/0008640, the distal end of the delivery system 10 can include one or more subassemblies such as an outer sheath assembly, a mid shaft assembly, a rail assembly, an inner shaft assembly, and a nose cone assembly. In some embodiments, the delivery system 10 may not have all of the assemblies disclosed herein. For example, in some embodiments a full mid shaft assembly may not be incorporated into the delivery system 10.

In particular, embodiments of the disclosed delivery system 10 can utilize a steerable rail in the rail assembly for steering the distal end of the delivery system 10, allowing the implant to be properly located in a patient's body. The steerable rail can be, for example, a rail shaft that extends through the delivery system 10 from the handle 14 generally to the distal end. In some embodiments, the steerable rail has a distal end that ends proximal to the implant retention area. A user can manipulate the bending of the distal end of the rail, thereby bending the rail in a particular direction. In preferred embodiments, the rail has more than one bend along its length, thereby providing multiple directions of bending. As the rail is bent, it presses against the other assemblies to bend them as well, and thus the other assemblies of the delivery system 10 can be configured to steer along with the rail as a cooperating single unit, thus providing for full steerability of the distal end of the delivery system.

Once the rail is steered into a particular location in a patient's body, the prosthesis 100 can be advanced along or relative to the rail through the movement of the other sheaths/shafts relative to the rail and released into the body. For example, the rail can be bent into a desired position within the body, such as to direct the prosthesis 100 towards the native mitral valve. The other assemblies (e.g., the outer sheath assembly, the mid shaft assembly, the inner assembly, and the nose cone assembly) can passively follow the bends of the rail. Further, the other assemblies (e.g., the outer sheath assembly, the mid shaft assembly, the inner assembly, and the nose cone assembly) can be advanced together (e.g., relatively together, sequentially with one actuator, simultaneously, almost simultaneously, at the same time, closely at the same time) relative to the rail while maintaining the prosthesis 100 in the compressed position without releasing or expanding the prosthesis 100 (e.g., within the implant retention area). The other assemblies (e.g., the outer sheath assembly, the mid shaft assembly, the inner assembly, and the nose cone assembly) can be advanced distally or proximally together relative to the rail. In some embodiments, only the outer sheath assembly, mid shaft assembly, and inner assembly are advanced together over the rail. Thus, the nose cone assembly may remain in the same position. The assemblies can be individually, sequentially, or simultaneously, translated relative to the inner assembly in order to release the implant 100 from the implant retention area.

In some embodiments, the outer sheath assembly, the mid shaft assembly, the inner shaft assembly, and the nose cone assembly translate together (e.g., relatively together, sequentially with one actuator, simultaneously, almost simultaneously, at the same time, closely at the same time). This distal translation can occur while the implant 100 remains in a compressed configuration within the implant retention area.

Starting with the outermost assembly, the delivery system 10 can include an outer sheath assembly forming a radially outer covering, or sheath, to surround an implant retention area and prevent the implant from radially expanding. Specifically, the outer sheath assembly can prevent radial expansion of the distal end of the implant from radially expanding. Moving radially inward, the mid shaft assembly can be composed of a mid shaft hypotube with its distal end attached to an outer retention member or outer retention ring for radially retaining a portion of the prosthesis in a compacted configuration, such as a proximal end of the prosthesis 100. The mid shaft assembly can be located within a lumen of the outer sheath assembly. Moving further inwards, the rail assembly can be configured for steerability, as mentioned above and further described below. The rail assembly can be located within a lumen of the mid shaft assembly. Moving further inwards, the inner shaft assembly can be composed of an inner shaft with its distal end attached to inner retention member or inner retention ring (such as a PEEK ring) for axially retaining the prosthesis, for example the proximal end of the prosthesis. The inner shaft assembly can be located within a lumen of the rail assembly.

Further, the most radially-inward assembly is the nose cone assembly which includes the nose cone shaft having its distal end connected to the nose cone. The nose cone can have a tapered tip. The nose cone assembly is preferably located within a lumen of the inner shaft assembly. The nose cone assembly can include a lumen for a guide wire to pass therethrough.

The shaft assembly 12, and more specifically the nose cone assembly, inner assembly, rail assembly, mid shaft assembly, and outer sheath assembly, can be collectively configured to deliver a prosthesis 100 positioned within the implant retention area to a treatment location. One or more of the subassemblies can then be moved to allow the prosthesis 100 to be released at the treatment location. For example, one or more of the subassemblies may be movable with respect to one or more of the other subassemblies. The handle 14 can include various control mechanisms that can be used to control the movement of the various subassemblies as will also be described in more detail below. In this way, the prosthesis 100 can be controllably loaded onto the delivery system 10 and then later deployed within the body. Further, the handle 14 can provide steering to the rail assembly, providing for bending/flexing/steering of the distal end of the delivery system 10.

The inner retention member, the outer retention ring, and the outer sheath assembly can cooperate to hold the prosthesis 100 in a compacted configuration. The inner retention member can engage struts (for example 132a/132b) at the proximal end of the prosthesis 100 in FIG. 2. For example, slots located between radially extending teeth on the inner retention member can receive and engage the struts which may end in mushroom-shaped tabs on the proximal end of the prosthesis 100. The mid shaft assembly can be positioned over the inner retention member so that the first end of the prosthesis 100 is trapped between the inner retention member and the outer retention ring, thereby securely attaching it to the delivery system 10 between the mid shaft assembly and the inner retention member. The outer sheath assembly can be positioned to cover the second end of the prosthesis 100.

The outer retention member may be attached to a distal end of the mid shaft hypotube which can in turn be attached to a proximal tube at a proximal end, which in turn can be attached at a proximal end to the handle 14. The outer retention member can provide further stability to the prosthesis 100 when in the compressed position. The outer retention member can be positioned over the inner retention member so that the proximal end of the prosthesis 100 is trapped therebetween, securely attaching it to the delivery system 10. The outer retention member can encircle a portion of the prosthesis 100, in particular the first end, thus preventing the prosthesis 100 from expanding. Further, the mid shaft assembly can be translated proximally with respect to the inner assembly into the outer sheath assembly, thus exposing a first end of the prosthesis 100 held within the outer retention member. In this way the outer retention member can be used to help secure a prosthesis 100 to or release it from the delivery system 10. The outer retention member can have a cylindrical or elongate tubular shape, and may be referred to as an outer retention ring, though the particular shape is not limiting.

The mid shaft hypotube itself can be made of, for example, high density polyethylene (HDPE), as well as other appropriate materials as described herein. The mid shaft hypotube can be formed of a longitudinally pre-compressed HDPE tube, which can provide certain benefits. For example, the pre-compressed HDPE tube can apply a force distally onto the outer retention member, thus preventing accidental, inadvertent, and/or premature release of the prosthesis 100. Specifically, the distal force by the mid shaft hypotube keeps the distal end of the outer retention member distal to the inner retention member, thus preventing the outer retention member from moving proximal to the inner retention member before it is desired by a user to release the prosthesis 100. This can remain true even when the delivery system 10 is bent/deflected at a sharp angle. Further disclosure for the outer retention member and mid shaft hypotube can be found in U.S. Pat. Pub. No. 2016/0317301, hereby incorporated by reference in its entirety.

In the compressed position, the inner frame anchoring features 124 can be located in a delivered configuration where the inner frame anchoring features 124 point generally distally. The inner frame anchoring features 124 can be restrained in this delivered configuration by the outer sheath assembly. Accordingly, when the outer sheath is withdrawn proximally, the inner frame anchoring features 124 can flip positions (e.g., bend approximately 180 degrees) to a deployed configuration (e.g., pointing generally proximally). In other embodiments, the inner frame anchoring features 124 can be held to point generally proximally in the delivered configuration and compressed against the body of the prosthesis frame.

The delivery system 10 may be provided to users with a prosthesis 100 preinstalled. In other embodiments, the prosthesis 100 can be loaded onto the delivery system shortly before use, such as by a physician or nurse.

Valve Delivery Positioning

Methods of using the delivery system 10 in connection with a replacement mitral valve will now be described. In particular, the delivery system 10 can be used in a method for percutaneous delivery of a replacement mitral valve to treat patients with moderate to severe mitral regurgitation. The below methods are merely examples of the how the delivery system may be used. It will be understood that the delivery systems described herein can be used as part of other methods as well.

Figure 32:
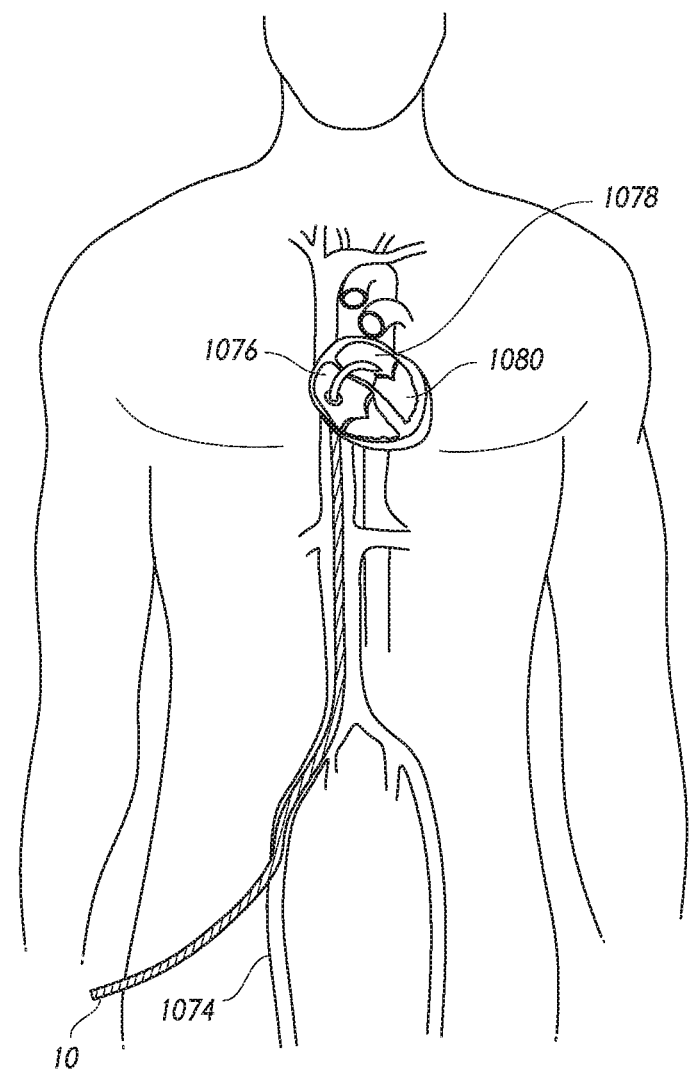
FIG. 32 illustrates a schematic representation of a transseptal delivery approach.

As shown in FIG. 32, in one embodiment the delivery system 10 can be placed in the ipsilateral femoral vein 1074 and advanced toward the right atrium 1076. A transseptal puncture using known techniques can then be performed to obtain access to the left atrium 1078. The delivery system 10 can then be advanced in to the left atrium 1078 and then to the left ventricle 1080. FIG. 32 shows the delivery system 10 extending from the ipsilateral femoral vein 1074 to the left atrium 1078. In embodiments of the disclosure, a guide wire is not necessary to position the delivery system 10 in the proper position, although in other embodiments, one or more guide wires may be used.

Accordingly, it can be advantageous for a user to be able to steer the delivery system 10 through the complex areas of the heart in order to position a replacement mitral valve in line with the native mitral valve. This task can be performed with or without the use of a guide wire with the above disclosed system. The distal end of the delivery system can be advanced into the left atrium 1078. A user can then manipulate the rail assembly to target the distal end of the delivery system 10 to the appropriate area. A user can then continue to pass the bent delivery system 10 through the transseptal puncture and into the left atrium 1078. A user can then further manipulate the delivery system 10 to create an even greater bend in the rail assembly. Further, a user can torque the entire delivery system 10 to further manipulate and control the position of the delivery system 10. In the fully bent configuration, a user can then place the replacement mitral valve in the proper location. This can advantageously allow delivery of a replacement valve to an in-situ implantation site, such as a native mitral valve, via a wider variety of approaches, such as a transseptal approach.

The rail assembly can be particularly advantageous for entering into the native mitral valve. As discussed above, the rail assembly can form two bends, both of which can be located in the left atrium 1078. The bends in the rail assembly can position the prosthesis (such as any of the designs disclosed above) so that it is coaxial with the native mitral valve. Once the prosthesis is coaxial, the outer sheath assembly, mid shaft assembly, inner assembly, and nose cone assembly can together be advanced (e.g., using a depth knob of a handle) distally relative to the rail assembly. These assemblies advance straight off of the rail assembly, thus advancing them coaxial with the native mitral valve until the prosthesis is to be released while maintain the prosthesis in the compressed configuration, as discussed below.

Figure 33:
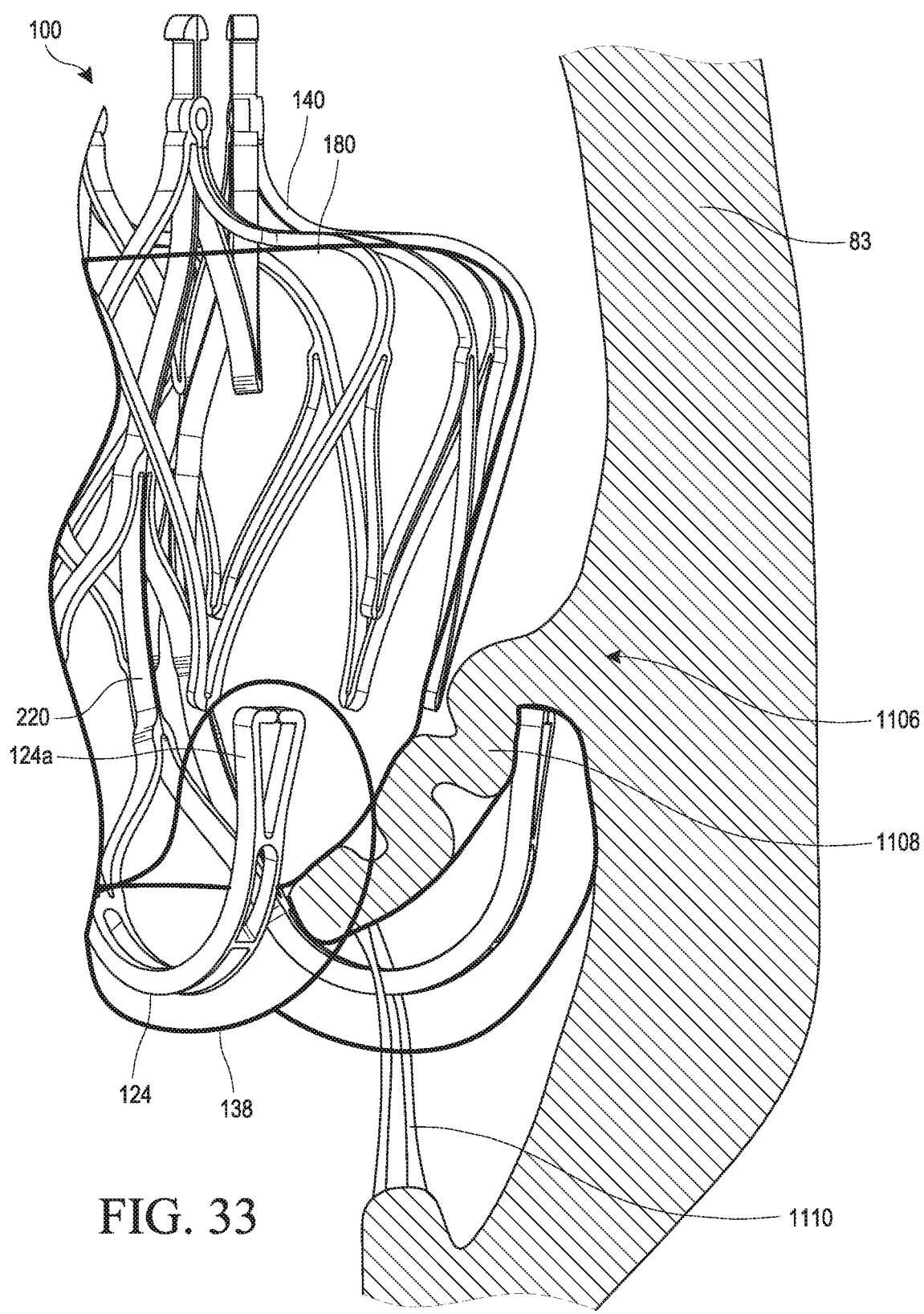
FIG. 33 illustrates a schematic representation of a valve prosthesis positioned within a native mitral valve.

Reference is now made to FIG. 33 which illustrates a schematic representation of a portion of an embodiment of a replacement heart valve 100 positioned within a native mitral valve of a heart 83. Further details regarding how the prosthesis may be positioned at the native mitral valve are described in U.S. Publication No. 2015/0328000A1, the entirety of which is hereby incorporated by reference, including but not limited to FIGS. 13A-15 and paragraphs [0036]-[0045]. A portion of the native mitral valve is shown schematically and represents typical anatomy, including a left atrium positioned above an annulus 1106 and a left ventricle positioned below the annulus 1106. The left atrium and left ventricle communicate with one another through a mitral annulus 1106. Also shown schematically in FIG. 33 is a native mitral leaflet 1108 having chordae tendineae 1110 that connect a downstream end of the mitral leaflet 1108 to the papillary muscle of the left ventricle 1080. The portion of the prosthesis 100 disposed upstream of the annulus 1106 (toward the left atrium) can be referred to as being positioned supra-annularly. The portion generally within the annulus 1106 is referred to as positioned intra-annularly. The portion downstream of the annulus 1106 is referred to as being positioned sub-annularly (toward the left ventricle).

As shown in FIG. 33, the replacement heart valve (e.g., prosthesis 100) can be positioned so that the mitral annulus 1106 is located above the inner frame anchoring features 124. In some situations, the prosthesis 100 can be positioned such that ends or tips of the inner frame anchoring features 124 contact the annulus 1106 as shown, for example, in FIG. 33. In some situations, the prosthesis 100 can be positioned such that ends or tips of the inner frame anchoring features 124 do not contact the annulus 1106. In some situations, the prosthesis 100 can be positioned such that the inner frame anchoring features 124 do not extend around the leaflet 1108.

As illustrated in FIG. 33, the replacement heart valve 70 can be positioned so that the ends or tips of the inner frame anchoring features 124 are on a ventricular side of the mitral annulus 1106. The inner frame anchoring features 124 can be positioned such that the ends or tips of the inner frame anchoring features 124 are on a ventricular side of the native leaflets beyond a location where chordae tendineae 1110 connect to free ends of the native leaflets. The inner frame anchoring features 124 may extend between at least some of the chordae tendineae 1110 and, in some situations such as those shown in FIG. 33, can contact or engage a ventricular side of the annulus 1106. It is also contemplated that in some situations, the inner frame anchoring features 124 may not contact the annulus 1106, though the inner frame anchoring features 124 may still contact the native leaflet 1108. In some situations, the inner frame anchoring features 124 can contact tissue of the left ventricle 104 beyond the annulus 1106 and/or a ventricular side of the leaflets.

During delivery, the inner frame anchoring features 124 (along with the frame) can be moved toward the ventricular side of the annulus 1106, such as by translating the other assemblies proximally with respect to the rail assembly, with the inner frame anchoring features 124 extending between at least some of the chordae tendineae 1110 to provide tension on the chordae tendineae 1110. The degree of tension provided on the chordae tendineae 1110 can differ. For example, little to no tension may be present in the chordae tendineae 1110 where the leaflet 1108 is shorter than or similar in size to the inner frame anchoring features 124. A greater degree of tension may be present in the chordae tendineae 1110 where the leaflet 1108 is longer than the inner frame anchoring features 124 and, as such, takes on a compacted form and is pulled proximally. An even greater degree of tension may be present in the chordae tendineae 1110 where the leaflets 1108 are even longer relative to the inner frame anchoring features 124. The leaflet 1108 can be sufficiently long such that the inner frame anchoring features 124 do not contact the annulus 1106.

Figure 34:
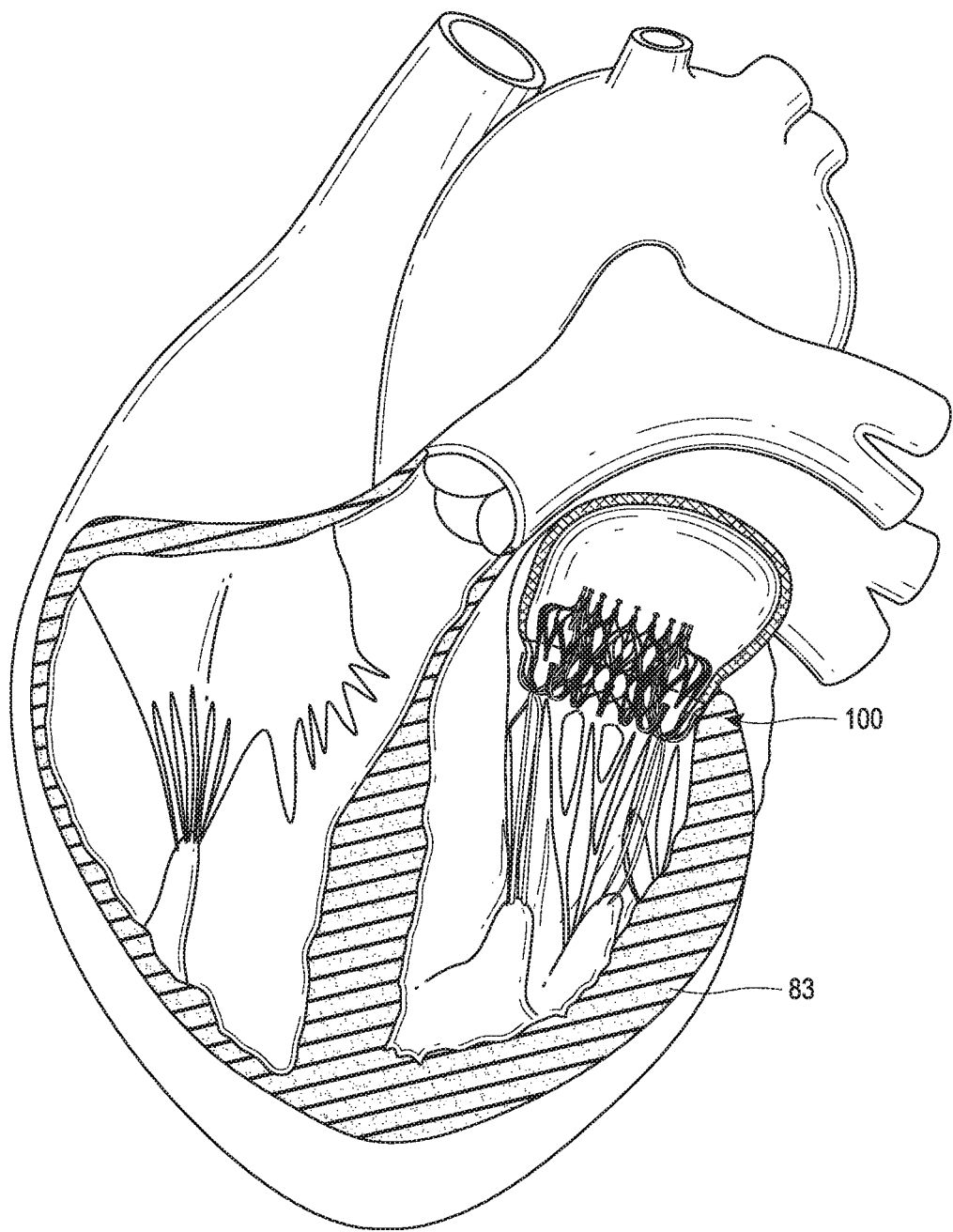
FIG. 34 illustrates a schematic representation of a valve prosthesis positioned within a native mitral valve.

As discussed above, the prosthesis 100 may not include an outer frame anchoring feature. However, some embodiments such as shown in FIG. 12 may include the outer frame anchoring feature 144. The outer frame anchoring feature 144, if present, can be positioned such that the ends or tips of the outer frame anchoring feature 144 are adjacent the atrial side of the annulus 1106 and/or tissue of the left atrium beyond the annulus 1106. In some situations, some or all of the outer frame anchoring feature 144 may only occasionally contact or engage atrial side of the annulus 1106 and/or tissue of the left atrium 1078 beyond the annulus 1106. For example, the outer frame anchoring feature 144 may be spaced from the atrial side of the annulus 1106 and/or tissue of the left atrium beyond the annulus 1106. The outer frame anchoring feature 144 could provide axial stability for the prosthesis 100. It is also contemplated that some or all of the outer frame anchoring feature 144 may contact the atrial side of the annulus 1106 and/or tissue of the left atrium beyond the annulus 1106. FIG. 34 illustrates the prosthesis 100 implanted in the heart 83. Although the illustrated replacement heart valve includes both proximal and distal anchors, it will be appreciated that proximal and distal anchors are not required in all cases. For example, a replacement heart valve with only distal anchors may be capable of securely maintaining the replacement heart valve in the annulus. This is because the largest forces on the replacement heart valve are directed toward the left atrium during systole. As such, the distal anchors are most important for anchoring the replacement heart valve in the annulus and preventing migration.

From the foregoing description, it will be appreciated that an inventive product and approaches for implantable prostheses are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A mitral valve prosthesis configured to transition between a compressed configuration and an expanded configuration, the prosthesis having a proximal end and a distal end, the prosthesis comprising:
   an inner frame comprising:
      a body comprising:
         a plurality of circumferentially extendable struts with respect to a longitudinal axis of the inner frame; and
         a plurality of longitudinally extending struts with respect to the longitudinal axis of the inner frame;
         wherein the plurality of circumferentially extendable struts and the plurality of longitudinally extending struts form two or more rows of cells; and
      a plurality of inner frame anchoring features extending distally from the body;
      wherein the body of the inner frame tapers radially inward from a first larger diameter at a proximal end of the body to a narrowest diameter of an intermediate region of the body and then tapers radially outward from the narrowest diameter of the intermediate region of the body to a second larger diameter at a distal end of the body so as to form a curved hourglass shape when the prosthesis is in the expanded configuration;
   an outer frame connected to the inner frame,
      wherein a longitudinal length of the outer frame overlaps with at least the intermediate region of the body of the inner frame when the prosthesis is in the expanded configuration;
   a valve body connected to a curved interior surface of the inner frame formed by the curved hourglass shape of the body of the inner frame, the valve body comprising a plurality of leaflets arranged to allow blood flow in a first direction and prevent blood flow in a second direction opposite the first direction, wherein the leaflets are adapted to have a longitudinal curvature when the valve body is in an open configuration that follows the curved hourglass shape of the body of the inner frame and conforms to and lies flush against the curved interior surface of the inner frame when the prosthesis is in the expanded configuration, thereby reducing a formation of thrombi between the plurality of leaflets and the curved interior surface of the inner frame; and
   a fabric skirt connected to an inner surface of the outer frame and extending distally beyond a distal end of the outer frame, wherein the fabric skirt is adapted for contacting a mitral valve annulus and forming a seal between the prosthesis and the mitral valve annulus.

2. The mitral valve prosthesis of claim 1, wherein the outer frame comprises a plurality of connected first v-shaped struts extending around a circumference of the outer frame; and a plurality of second v-shaped struts, each of the second v-shaped struts positioned within gaps formed between each of the connected first v-shaped struts and attached to adjacent pairs of the connected first v-shaped struts, wherein the plurality of second v-shaped struts are thinner than the plurality of connected first v-shaped struts.

3. The mitral valve prosthesis of claim 2, wherein the outer frame comprises a plurality of proximally extending struts extending between connections of adjacent connected first v-shaped struts.

4. The mitral valve prosthesis of claim 1, further comprising one or more sutures attached to the outer frame, the inner frame, and the plurality of inner frame anchoring features, the one or more sutures providing tension to the inner frame anchoring features when the prosthesis is in the expanded configuration and not providing tension to the inner frame anchoring features when the prosthesis is in the compressed configuration.

5. The mitral valve prosthesis of claim 1, wherein the plurality of inner frame anchoring features extend radially outwardly and then proximally toward the proximal end of the prosthesis when the prosthesis is in the expanded configuration, wherein each of the plurality of inner frame anchoring features ends with an anchoring tip.

6. The mitral valve prosthesis of claim 5, wherein each anchoring tip at the end of each of the plurality of inner frame anchoring features is located proximal to the distal end of the outer frame and is spaced radially outward of the outer frame when the prosthesis is in the expanded configuration such that native leaflets of the mitral valve are configured to be trapped in a space between at least one of the anchoring tips and the outer frame.

7. The mitral valve prosthesis of claim 1, wherein the distal end of the outer frame ends proximal to a distal end of the two or more rows of cells of the body of the inner frame.

8. The mitral valve prosthesis of claim 1, wherein the inner frame comprises a mushroom-shaped tab at a proximal end of at least one of the plurality of longitudinally extending struts.

9. The mitral valve prosthesis of claim 1, wherein the inner frame comprises a plurality of apertures at or near a proximal end of the inner frame, wherein the outer frame comprises a plurality of apertures at or near a proximal end of the outer frame, and wherein each one of the plurality of apertures of the inner frame generally aligns with a respective one of the plurality of apertures of the outer frame.

10. The mitral valve prosthesis of claim 1, wherein the outer frame comprises a circumferential shoulder spaced from a proximal end of the outer frame and the distal end of the outer frame, the circumferential shoulder being the radially outermost portion of the outer frame.

11. The mitral valve prosthesis of claim 1, wherein the plurality of inner frame anchoring features comprises nine inner frame anchoring features.

12. The mitral valve prosthesis of claim 1, wherein free edges of a distal end of each of the plurality of leaflets are spaced away from the inner frame.

13. The mitral valve prosthesis of claim 1, wherein the fabric skirt is connected to an outer surface of the distal end of the body of the inner frame, and wherein the fabric skirt is held in tension between the outer frame and the inner frame.

14. The mitral valve prosthesis of claim 1, wherein the fabric skirt has sufficient flexibility to conform against a mitral valve annulus.

15. A mitral valve prosthesis configured to transition between a compressed configuration and an expanded configuration, the prosthesis having a proximal end and a distal end, the prosthesis comprising:
an inner frame comprising:
a body comprising:
a plurality of circumferentially extendable struts; and
a plurality of longitudinally extending struts;
wherein the plurality of circumferentially extendable struts and the plurality of longitudinally extending struts form two or more rows of cells; and
a plurality of inner frame anchoring features extending distally from the body;
wherein the body of the inner frame comprises an upper region, an intermediate region, and a lower region, wherein the intermediate region has a narrower diameter than both the upper region and the lower region when the prosthesis is in the expanded configuration so as to form an interior surface that tapers radially inward from the upper region toward the intermediate region and tapers radially outward from the intermediate region to the lower region;
an outer frame connected to the inner frame,
wherein, when the prosthesis is in the expanded configuration, the outer frame comprises a bulbous shape in which a circumferential shoulder of the outer frame is spaced from a proximal end of the outer frame and a distal end of the outer frame, the circumferential shoulder being the radially outermost portion of the outer frame,
wherein at least the intermediate region of the inner frame is positioned radially within a portion of a length of the outer frame when the prosthesis is in the expanded configuration,
wherein, when the prosthesis is in the expanded configuration, the plurality of inner frame anchoring features extend radially outward and then curve proximally toward the proximal end of the prosthesis external to the outer frame and proximal to the distal end of the outer frame such that native leaflets of a mitral valve can be captured in a space formed between the outer frame and the plurality of inner frame anchoring features;
a valve body connected along the interior surface of the inner frame, the valve body comprising a plurality of leaflets arranged to allow blood flow in a first direction and prevent blood flow in a second direction opposite the first direction, wherein the leaflets are adapted to have a longitudinal curvature when the valve body is in an open configuration that conforms to the interior surface of the inner frame when the prosthesis is in the expanded configuration, thereby reducing a formation of thrombi between the plurality of leaflets and the interior surface of the inner frame; and
a fabric skirt connected under tension to an inner surface of the outer frame and an outer surface of a distal end of the inner frame, wherein the fabric skirt extends distally beyond the distal end of the outer frame, and wherein the fabric skirt is adapted for conforming against a mitral valve annulus.

16. A heart valve prosthesis configured to transition between a compressed configuration and an expanded configuration, the prosthesis having a proximal end and a distal end, the prosthesis comprising:
an inner frame comprising:
a body comprising:
a plurality of circumferentially extendable struts; and
a plurality of longitudinally extending struts;
wherein the plurality of circumferentially extendable struts and the plurality of longitudinally extending struts form two or more rows of cells; and
a plurality of inner frame anchoring features extending distally from the body;
wherein the body of the inner frame comprises an upper region, an intermediate region, and a lower region, wherein the body of the inner frame tapers radially inward from a first larger diameter of the upper region to a narrowest diameter of the intermediate region and then tapers radially outward from the narrowest diameter of the intermediate region to a second larger diameter of the lower region so as to form a curved shape when the prosthesis is in the expanded configuration;

an outer frame connected to the inner frame,
wherein the outer frame surrounds at least the intermediate region of the body of the inner frame such that a length of the intermediate region of the body of the inner frame overlaps longitudinally with a length of the outer frame when the prosthesis is in the expanded configuration; and a valve body connected to a curved interior surface of the inner frame formed by the curved shape of the body of the inner frame, the valve body comprising a plurality of leaflets arranged to allow blood flow in a first direction and prevent blood flow in a second direction opposite the first direction, wherein a longitudinal length of the leaflets is adapted to have a final curvature when the valve body is in an open configuration that conforms to and contacts the curved interior surface of the inner frame when the prosthesis is in the expanded configuration.

17. The heart valve prosthesis of claim 16, wherein over 90% of the longitudinal length of the leaflets contacts the curved interior surface of the inner frame when the valve body is in the open configuration.

18. The heart valve prosthesis of claim 16, wherein only free edges at a distal end of the leaflets do not contact the inner frame when the valve body is in the open configuration.

19. The heart valve prosthesis of claim 16, wherein the upper region of the body of the inner frame and an upper region of the outer frame each comprise corresponding eyelets and wherein the inner frame and the outer frame are attached together via the corresponding eyelets of the inner frame and the outer frame.

20. The heart valve prosthesis of claim 16, wherein, when the prosthesis is in the expanded configuration and when the valve body is in the open configuration, an intermediate portion of the longitudinal length of the leaflets contacts a waist of the intermediate region of the valve body having the narrowest diameter.

* * * * *